(12) United States Patent
Gugumus

(10) Patent No.: US 6,368,520 B1
(45) Date of Patent: *Apr. 9, 2002

(54) SYNERGISTIC STABILIZER MIXTURE

(75) Inventor: François Gugumus, Allschwil (CH)

(73) Assignee: Ciba Specialty Chemicals Corporation, Tarrytown, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/103,443

(22) Filed: Jun. 24, 1998

Related U.S. Application Data

(62) Division of application No. 08/628,439, filed on Apr. 5, 1996, now Pat. No. 5,980,783.

(30) Foreign Application Priority Data

Apr. 11, 1995 (CH) .................................. 1069/95

(51) Int. Cl.⁷ ...................... C09K 15/30; C09K 15/22; C08J 3/20; C08K 5/3435; C08K 5/3492
(52) U.S. Cl. ...................... 252/401; 252/403; 252/405; 524/99; 524/100; 524/101; 524/102
(58) Field of Search .............................. 252/401, 403, 252/405; 524/100, 99, 101, 102

(56) References Cited

U.S. PATENT DOCUMENTS 3,640,928 A    2/1972 Murayama et al. ........... 260/23

(List continued on next page.)

FOREIGN PATENT DOCUMENTS

DE            262439          11/1988

(List continued on next page.)

OTHER PUBLICATIONS

Derw. Abst. 89–122983/17 of DD 262,439.

(List continued on next page.)

*Primary Examiner*—Shean C. Wu
(74) *Attorney, Agent, or Firm*—Luther A. R. Hall; David R. Crichton

(57) ABSTRACT

Stabilizer mixture comprising, for example, a compound of the formula

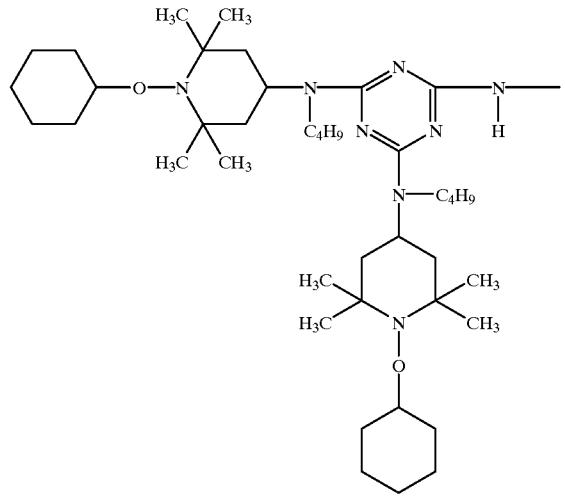

and, for example, a compound of the formula

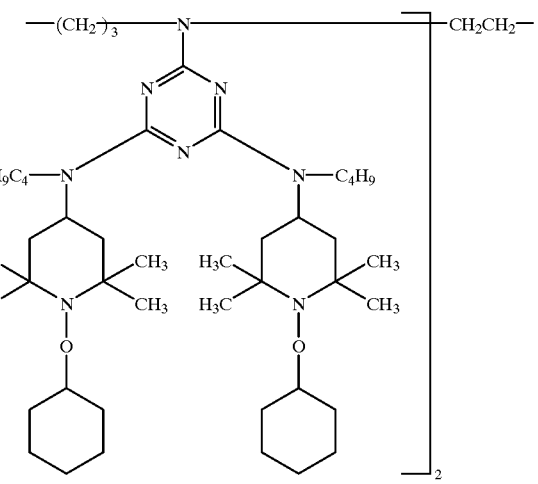

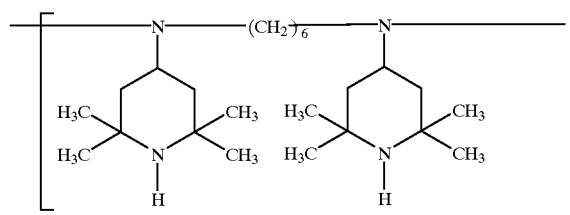

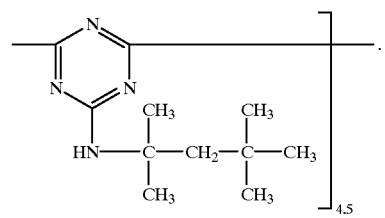

10 Claims, No Drawings

U.S. PATENT DOCUMENTS

| | | | |
|---|---|---|---|
| 3,925,376 A | 12/1975 | Chalmers et al. | 260/248 |
| 4,086,204 A | 4/1978 | Cassandrini et al. | 260/45.8 |
| 4,108,829 A | 8/1978 | Cassandrini et al. | 260/45.8 |
| 4,110,334 A | 8/1978 | Mayer et al. | 260/293.66 |
| 4,233,412 A | 11/1980 | Rody et al. | 525/167 |
| 4,331,586 A | 5/1982 | Hardy | 525/186 |
| 4,340,534 A | 7/1982 | Wiezer et al. | 524/99 |
| 4,356,307 A | 10/1982 | Kelkenberg et al. | 546/200 |
| 4,408,051 A | 10/1983 | Hinsken et al. | 546/19 |
| 4,477,615 A | 10/1984 | Raspanti et al. | 524/100 |
| 4,529,760 A | 7/1985 | Leistner et al. | 524/102 |
| 4,689,416 A | 8/1987 | Ertl et al. | 546/19 |
| 4,691,015 A | 9/1987 | Behrens et al. | 544/198 |
| 4,692,486 A | 9/1987 | Gugumus | 524/100 |
| 4,857,595 A | 8/1989 | Kazmierzak et al. | 525/142 |
| 4,863,981 A | 9/1989 | Gugumus | 524/97 |
| 4,957,953 A | 9/1990 | Kikkawa et al. | 524/99 |
| 5,021,485 A | 6/1991 | Gugumus | 524/100 |
| 5,051,458 A | 9/1991 | Castanzi et al. | 524/99 |
| 5,096,950 A | 3/1992 | Galbo et al. | 524/99 |
| 5,118,736 A | 6/1992 | Ravichandran | 524/100 |
| 5,182,390 A | 1/1993 | Sagawa et al. | 544/222 |
| 5,204,473 A | 4/1993 | Winter et al. | 546/188 |
| 5,447,576 A * | 9/1995 | Willis | 136/259 |
| 5,658,973 A | 8/1997 | Raspanti | 524/99 |
| 5,719,217 A | 2/1998 | Gugmus | 524/100 |
| 5,919,399 A * | 7/1999 | Gugmus | 252/403 |
| 5,965,641 A * | 10/1999 | Gugumus | 524/100 |
| 5,977,221 A * | 11/1999 | Gugumus | 524/100 |
| 6,015,849 A * | 1/2000 | Gugumus | 524/100 |
| 6,020,406 A * | 2/2000 | Gugumus | 524/95 |

FOREIGN PATENT DOCUMENTS

| | | |
|---|---|---|
| EP | 0309401 | 3/1989 |
| EP | 0449685 | 3/1991 |
| EP | 0632092 | 7/1994 |
| GB | 2267499 | 12/1993 |
| WO | 9212201 | 7/1992 |
| WO | 9412544 | 6/1994 |
| WO | 9422946 | 10/1994 |

OTHER PUBLICATIONS

Material Safety Data Sheet CAS No. 136 504–96–6 Research Discl. 34 549 (Jan. 1993).

Derw. Abst. 94–177274/22.

* cited by examiner

SYNERGISTIC STABILIZER MIXTURE

This application is a divisional of prior application Ser. No. 08/628,439 filed Apr. 5, 1996 U.S. Pat. No. 5,980,783.

The present invention relates to a stabilizer system comprising two specific polyalkylpiperidine derivatives, some of which are novel, to the use of this stabilizer system for stabilizing organic material, and to the organic material protected against thermal, oxidative or light-induced degradation by means of the stabilizer system mentioned.

Polyalkylpiperidine derivatives are described for example in WO-A-94/112 544, U.S. Pat. No. 4,110,334 and U.S. Pat. No. 5,204,473.

U.S. Pat. No. 4,692,486, U.S. Pat. No. 4,863,981, U.S. Pat. No. 4,957,953, WO-A-92/12 201, WO-A-94/22 946, EP-A-449 685, EP-A-632 092, GB-A-2 267 499 and Research Disclosure 34 549 (January 1993) describe some stabilizer mixtures which comprise two polyalkylpiperidine derivatives.

The present invention relates to a stabilizer mixture comprising a component I-a), I-b), I-c), I-d), I-e), I-f), I-g), I-h), I-i), I-j), I-k) or I-l) and a component II-a), II-b), II-c), II-d), II-e), II-f), II-g), II-h), II-i), II-j), II-k), II-l) or II-m), where component I-a) is at least one compound of the formula I-1

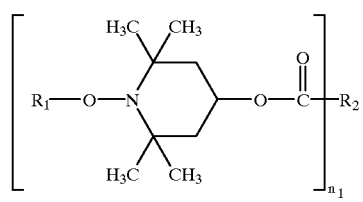

(I-1)

in which $R_1$ is hydrogen, $C_1$–$C_{18}$alkyl, $C_5$–$C_{12}$cycloalkyl or $C_1$–$C_4$alkyl-substituted $C_5$–$C_{12}$cycloalkyl, $n_1$ is 1, 2 or 4, if $n_1$ is 1, $R_2$ is $C_1$–$C_{25}$alkyl, if $n_1$ is 2, $R_2$ is $C_1$–$C_{14}$alkylene and if $n_1$ is 4, $R_2$ is $C_4$–$C_{10}$alkanetetrayl, with the provisos that, (1) in a stabilizer mixture comprising component I-a) and component II-b) or I-m), if $n_1$=2, $R_1$ is other than $C_1$–$C_{18}$alkyl and (2) in a stabilizer mixture comprising component I-a) and component II-d), if $n_1$=2 and $R_1$=$C_1$–$C_{18}$alkyl, the group —$N(A_{14})A_{15}$ is a 5- to 10-membered heterocyclic ring;

component I-b) is at least one compound of the formula II-1

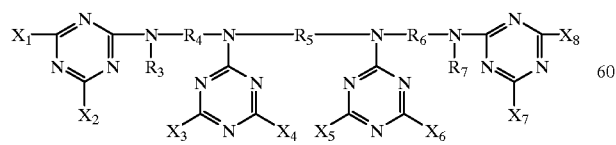

(II-1)

in which $R_3$ and $R_7$ independently of one another are hydrogen or $C_1$–$C_{12}$alkyl, $R_4$, $R_5$ and $R_6$ independently of one another are $C_2$–$C_{10}$alkylene and $X_1$, $X_2$, $X_3$, $X_4$, $X_5$, $X_6$, $X_7$ and $X_8$ independently of one another are a group of the formula III-1

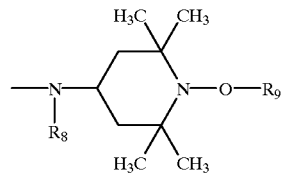

(III-1)

in which $R_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or is a group of the formula IV-1

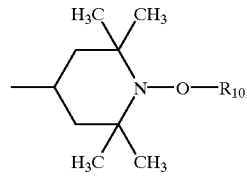

(IV-1)

and $R_9$ and $R_{10}$ independently of one another are as defined for $R_1$;

component I-c) is at least one compound of the formula V-1

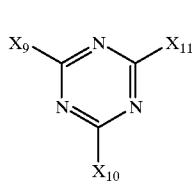

(V-1)

in which $X_9$, $X_{10}$ and $X_{11}$ independently of one another are a group of the formula III-1;

component I-d) is at least one compound of the formula VI-1

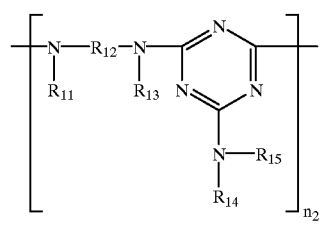

(VI-1)

in which $R_{11}$, $R_{13}$, $R_{14}$ and $R_{15}$ independently of one another are hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or are a group of the formula IV-1, $R_{12}$ is $C_2$–$C_{18}$alkylene, $C_5$–$C_7$cycloalkylene or $C_1$–$C_4$alkylenedi($C_5$–$C_7$cycloalkylene), or the radicals $R_{11}$, $R_{12}$ and $R_{13}$, together with the nitrogen atoms to which they are attached, form a 5- to 10-membered heterocyclic ring, or $R_{14}$ and $R_{15}$, together with the nitrogen atom to which they are attached, form a 5- to 10-membered heterocyclic ring, $n_2$ is a number from 2 to 50 and at least one of the radicals $R_{11}$, $R_{13}$, $R_{14}$ and $R_{15}$ is a group of the formula IV-1;

component I-e) is at least one compound of the formula VII-1

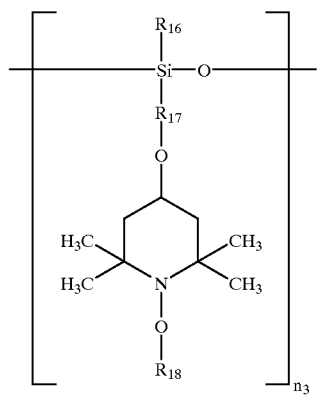

(VII-1)

in which $R_{16}$ is $C_1$–$C_{10}$alkyl, $C_5$–$C_{12}$cycloalkyl, $C_1$–$C_4$alkyl-substituted $C_5$–$C_{12}$cycloalkyl, phenyl or $C_1$–$C_{10}$alkyl-substituted phenyl, $R_{17}$ is $C_3$–$C_{10}$alkylene, $R_{18}$ is as defined for $R_1$ and $n_3$ is a number from 1 to 50;

component I-f) is a product obtainable by a) reacting a product, obtained by reaction of a polyamine of the formula VIII-1-a with cyanuric chloride, with a compound of the formula VIII-1-b

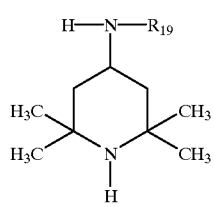

(VIII-1-b)

in which $n_4'$, $n_4''$ and $n_4'''$ independently of one another are a number from 2 to 12 and $R_{19}$ is hydrogen, $C_1$–$C_{12}$alkyl, $C_5$–$C_{12}$cycloalkyl, phenyl or $C_7$–$C_9$phenylalkyl, and b) further reacting the 2,2,6,6-tetramethylpiperid-4-yl groups present in the molecule to give groups of the formula VIII-1-c

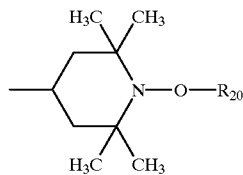

(VIII-1-c)

in which $R_{20}$ is as defined for $R_1$;

component I-g) is at least one compound of the formula IX-1

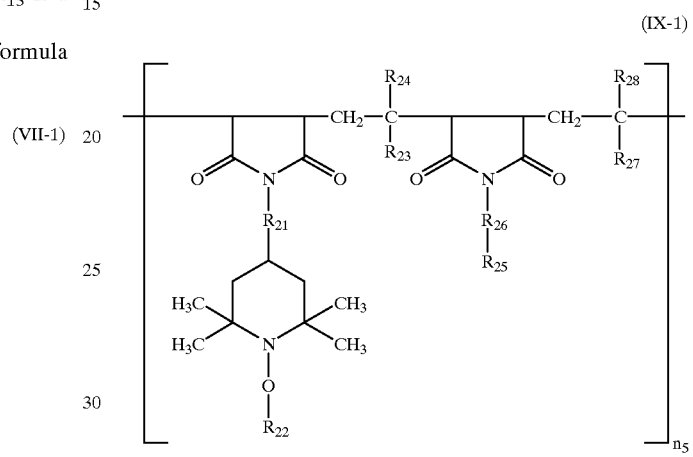

(IX-1)

in which $R_{21}$ and $R_{26}$ independently of one another are a direct bond or a group —$N(Y_1)$—CO—$Y_2$—CO—N$(Y_3)$—, $Y_1$ and $Y_3$ independently of one another are hydrogen, $C_1$–$C_8$alkyl, $C_5$–$C_{12}$cycloalkyl, phenyl, $C_7$–$C_9$phenylalkyl or a group of the formula IV-1, $Y_2$ is a direct bond or $C_1$–$C_4$alkylene, $R_{22}$ is as defined for $R_1$, $R_{23}$, $R_{24}$, $R_{27}$ and $R_{28}$ independently of one another are hydrogen, $C_1$–$C_{30}$alkyl, $C_5$–$C_{12}$cycloalkyl or phenyl, $R_{25}$ is hydrogen, $C_1$–$C_{30}$alkyl, $C_5$–$C_{12}$cycloalkyl, phenyl, $C_7$–$C_9$phenylalkyl or a group of the formula IV-1 and $n_5$ is a number from 1 to 50;

component I-h) is at least one compound of the formula X-1

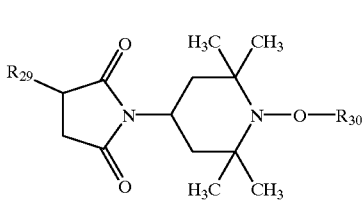

(X-1)

in which $R_{29}$ is $C_1$–$C_{24}$alkyl and $R_{30}$ is as defined for $R_1$;

component I-i) is at least one compound of the formula XI-1

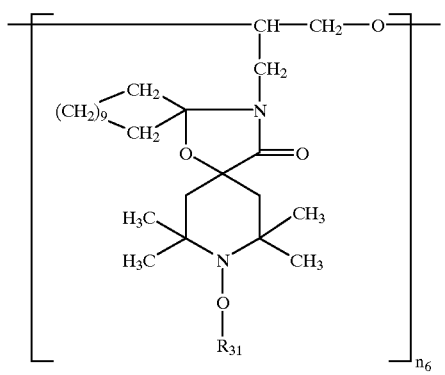

(XI-1)

in which
$R_{31}$ is as defined for $R_1$ and
$n_6$ is a number from 2 to 50;

component I-j) is at least one compound of the formula XII-1

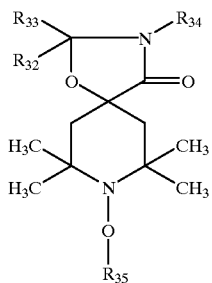

(XII-1)

in which
$R_{32}$ and $R_{33}$ together form $C_2$–$C_{14}$alkylene,
$R_{34}$ is hydrogen or a group —$Z_1$—COO—$Z_2$,
$Z_1$ is $C_2$–$C_{14}$alkylene and
$Z_2$ is $C_1$–$C_{24}$alkyl and
$R_{35}$ is as defined for $R_1$;

component I-k) is at least one compound of the formula XIII-1 in which $R_{36}$, $R_{37}$, $R_{38}$, $R_{39}$ and $R_{40}$ independently of one another are a direct bond or $C_1$–$C_{10}$alkylene,
$R_{41}$ is as defined for $R_1$ and
$n_7$ is a number from 1 to 50;

component I-l) is at least one compound of the formula XIV-1

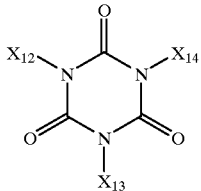

(XIV-1)

in which
$X_{12}$, $X_{13}$ and $X_{14}$ independently of one another are a group of the formula XV-1

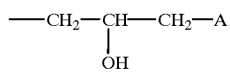

(XV-1)

in which A is a group of the formula III-1;

component II-a) is at least one compound of the formula I-2

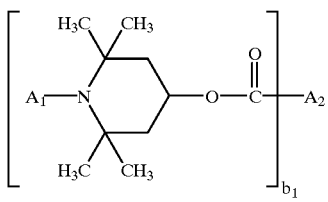

(I-2)

in which
$A_1$ is hydrogen, $C_1$–$C_8$alkyl, O, —$CH_2CN$, $C_3$–$C_6$alkenyl, $C_7$–$C_9$phenylalkyl or $C_7$–$C_9$phenylalkyl which is substituted on the phenyl radical by $C_1$–$C_4$alkyl,
$b_1$ is 1, 2 or 4,

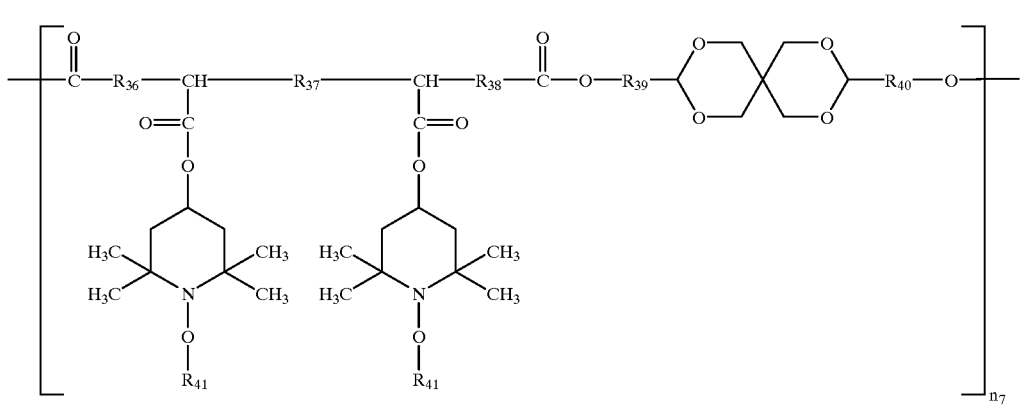

(XIII-1)

if $b_1$ is 1, $A_2$ is $C_1$–$C_{25}$alkyl,
if $b_1$ is 2, $A_2$ is $C_1$–$C_{14}$alkylene and
if $b_1$ is 4, $A_2$ is $C_4$–$C_{10}$alkanetetrayl;

component II-b) is at least one compound of the formula II-2

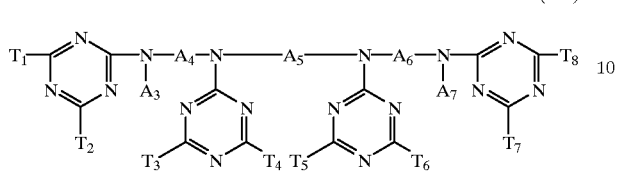

(II-2)

in which
$A_3$ and $A_7$ independently of one another are hydrogen or $C_1$–$C_{12}$alkyl,
$A_4$, $A_5$ and $A_6$ independently of one another are $C_2$–$C_{10}$alkylene and
$T_1$, $T_2$, $T_3$, $T_4$, $T_5$, $T_6$, $T_7$ and $T_8$ independently of one another are a group of the formula III-2

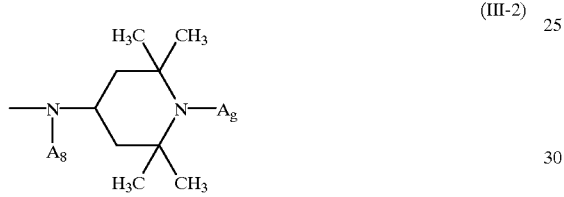

(III-2)

in which $A_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or is a group of the formula IV-2

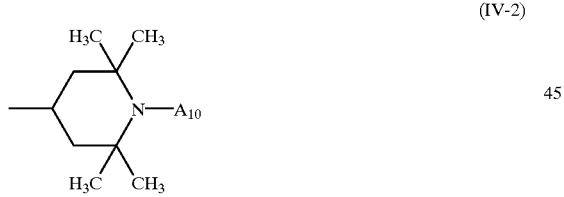

(IV-2)

and $A_9$ and $A_{10}$ independently of one another are as defined for $A_1$;

component II-c) is at least one compound of the formula V-2

(V-2)

in which
$T_9$, $T_{10}$ and $T_{11}$ independently of one another are a group of the formula III-2;

component II-d) is at least one compound of the formula VI-2

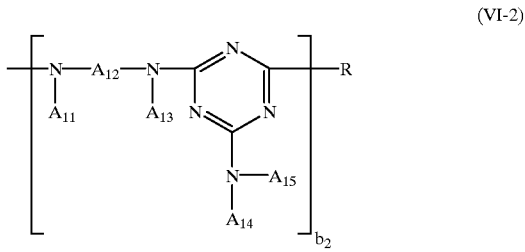

(VI-2)

in which
$A_{11}$, $A_{13}$, $A_{14}$ and $A_{15}$ independently of one another are hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or are a group of the formula IV-2,
$A_{12}$ is $C_2$–$C_{18}$alkylene, $C_5$–$C_7$cycloalkylene or $C_1$–$C_4$alkylenedi($C_5$–$C_7$cycloalkylene), or the radicals $A_{11}$, $A_{12}$ and $A_{13}$, together with the nitrogen atoms to which they are attached, form a 5- to 10-membered heterocyclic ring, or
$A_{14}$ and $A_{15}$, together with the nitrogen atom to which they are attached, form a 5- to 10-membered heterocyclic ring,
$b_2$ is a number from 2 to 50 and
at least one of the radicals $A_{11}$, $A_{13}$, $A_{14}$ and $A_{15}$ is a group of the formula IV-2;

component II-e) is at least one compound of the formula VII-2

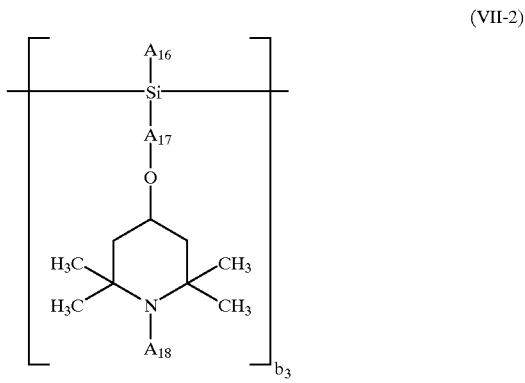

(VII-2)

in which
$A_{16}$ is $C_1$–$C_{10}$alkyl, $C_5$–$C_{12}$cycloalkyl, $C_1$–$C_4$alkyl-substituted $C_5$–$C_{12}$cycloalkyl, phenyl or $C_1$–$C_{10}$alkyl-substituted phenyl,
$A_{17}$ is $C_3$–$C_{10}$alkylene,
$A_{18}$ is as defined for $A_1$ and
$b_3$ is a number from 1 to 50;

component II-f) is a product obtainable by reacting a product, obtained by reaction of a polyamine of the formula VIII-2-a with cyanuric chloride, with a compound of the formula VIII-2-b

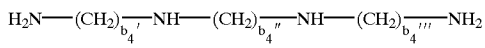
(VIII-2-a)

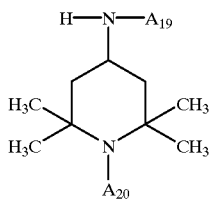
(VIII-2-b)

in which $b_4'$, $b_4''$ and $b_4'''$ independently of one another are a number from 2 to 12, $A_{19}$ is hydrogen, $C_1$–$C_{12}$alkyl, $C_5$–$C_{12}$cycloalkyl, phenyl or $C_7$–$C_9$phenylalkyl and $A_{20}$ is as defined for $A_1$;

component II-g) is at least one compound of the formula IX-2

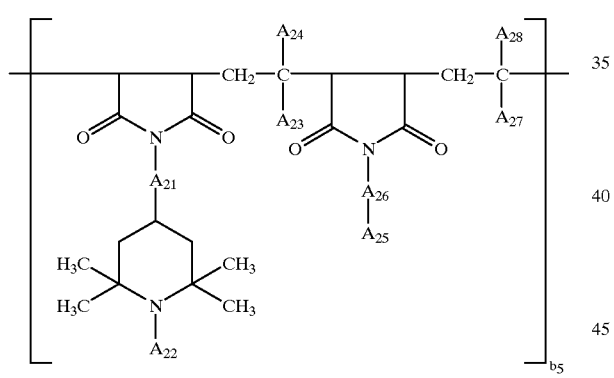
(IX-2)

in which $A_{21}$ and $A_{26}$ independently of one another are a direct bond or a group —N($E_1$)—CO—$E_2$—CO—N($E_3$)—, $E_1$ and $E_3$ independently of one another are hydrogen, $C_1$–$C_8$alkyl, $C_5$–$C_{12}$cycloalkyl, phenyl, $C_7$–$C_9$phenylalkyl or a group of the formula IV-2, $E_2$ is a direct bond or $C_1$–$C_4$alkylene, $A_{22}$ is as defined for $A_1$, $A_{23}$, $A_{24}$, $A_{27}$ and $A_{28}$ independently of one another are hydrogen, $C_1$–$C_{30}$alkyl, $C_5$–$C_{12}$cycloalkyl or phenyl, $A_{25}$ is hydrogen, $C_1$–$C_{30}$alkyl, $C_5$–$C_{12}$cycloalkyl, phenyl, $C_7$–$C_9$phenylalkyl or a group of the formula IV-2 and $b_5$ is a number from 1 to 50;

component II-h) is at least one compound of the formula X-2

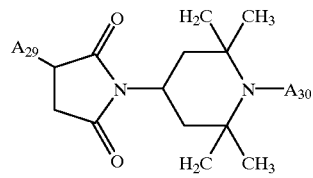
(X-2)

in which $A_{29}$ is $C_1$–$C_{24}$alkyl and $A_{30}$ is as defined for $A_1$;

component II-i) is at least one compound of the formula XI-2

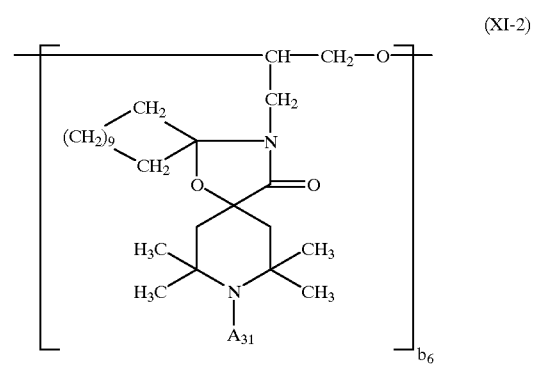
(XI-2)

in which $A_{31}$ is as defined for $A_1$ and $b_6$ is a number from 2 to 50;

component II-j) is at least one compound of the formula XII-2

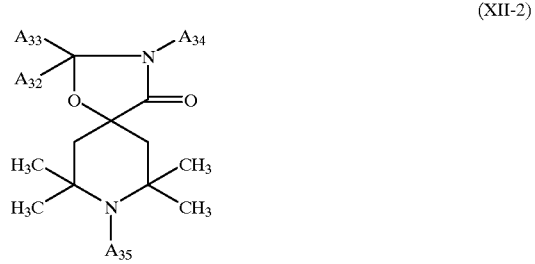
(XII-2)

in which $A_{32}$ and $A_{33}$ together form $C_2$–$C_{14}$alkylene, $A_{34}$ is hydrogen or a group —$G_1$—COO—$G_2$, $G_1$ is $C_2$–$C_{14}$alkylene and $G_2$ is $C_1$–$C_{24}$alkyl and $A_{35}$ is as defined for $A_1$;

component II-k) is at least one compound of the formula XIII-2

(XIII-2)

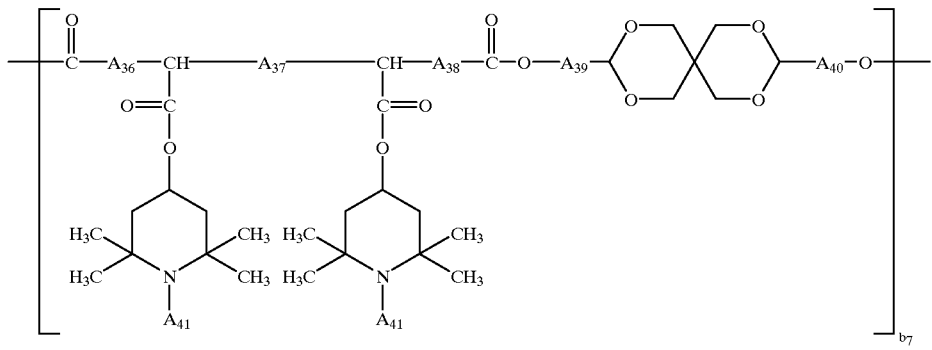

in which $A_{36}$, $A_{37}$, $A_{38}$, $A_{39}$ and $A_{40}$ independently of one another are a direct bond or $C_1$–$C_{10}$alkylene, $A_{41}$ is as defined for $A_1$ and
$b_7$ is a number from 1 to 50;
component II-1) is at least one compound of the formula XIV-2

(XIV-2)

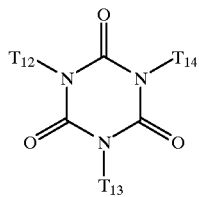

in which
$T_{12}$, $T_{13}$ and $T_{14}$ independently of one another are a group of the formula XV-2

(XV-2)

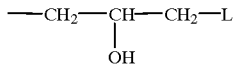

in which L is a group of the formula III-2;
component II-m) is at least one compound of the formula XVI-2

(XVI-2)

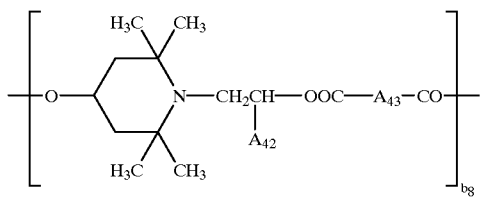

in which $A_{42}$ is hydrogen or methyl,
$A_{43}$ is a direct bond or $C_1$–$C_{10}$alkylene and
$b_8$ is a number from 2 to 50.

Examples of alkyl having up to 30 carbon atoms are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetra-methylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl, docosyl and triacontyl. One of the preferred definitions of $A_1$, $A_9$, $A_{10}$, $A_{18}$, $A_{20}$, $A_{22}$, $A_{30}$, $A_{31}$, $A_{35}$ and $A_{41}$ is $C_1$–$C_4$alkyl, especially methyl. One of the preferred definitions of $R_{23}$, $R_{27}$, $A_{23}$ and $A_{27}$ is $C_1$–$C_{25}$alkyl, especially $C_{15}$–$C_{25}$alkyl, for example hexadecyl and $C_{18}$–$C_{22}$alkyl. One of the preferred definitions of $R_{25}$ and $A_{25}$ is $C_1$–$C_{25}$alkyl, especially octadecyl. One of the preferred definitions of $R_9$, $R_{19}$, $A_8$ and $A_{19}$ is $C_1$–$C_4$alkyl, especially n-butyl.

Examples of $C_5$–$C_{12}$cycloalkyl are cyclopentyl, cyclohexyl, cycloheptyl, cyclooctyl and cyclododecyl. $C_5$–$C_8$Cycloalkyl, especially cyclohexyl, is preferred.

In a stabilizer mixture comprising component I-a) and component II-b) or II-m), $R_1$ is preferably $C_1$–$C_8$cycloalkyl, especially cyclohexyl.

$C_1$–$C_4$Alkyl-substituted $C_5$–$C_{12}$cycloalkyl is for example methylcyclohexyl or dimethylcyclohexyl.

—OH— and/or $C_1$–$C_{10}$alkyl-substituted phenyl is for example methylphenyl, dimethylphenyl, trimethylphenyl, tert-butylphenyl or 3,5-di-tert-butyl-4-hydroxyphenyl.

Examples of $C_7$–$C_9$phenylalkyl are benzyl and phenylethyl.

$C_7$–$C_9$Phenylalkyl which is substituted on the phenyl radical by —OH and/or by alkyl having up to 10 carbon atoms is for example methylbenzyl, dimethylbenzyl, trimethylbenzyl, tert-butylbenzyl or 3,5-di-tert-butyl-4-hydroxybenzyl.

Examples of $C_3$–$C_6$alkenyl are allyl, 2-methallyl, butenyl, pentenyl and hexenyl. Allyl is preferred. The carbon atom in position 1 is preferably saturated.

Examples of alkylene having up to 18 carbon atoms are methylene, ethylene, propylene, trimethylene, tetramethylene, pentamethylene, 2,2-dimethyltrimethylene, hexamethylene, trimethylhexamethylene, octamethylene and decamethylene. $R_{12}$ and $A_{12}$ are preferably hexamethylene, $A_{43}$ is preferably ethylene, $R_{36}$, $R_{38}$, $A_{36}$ and $A_{38}$ are preferably methylene, $R_{39}$ and $A_{39}$ are preferably 2,2-dimethylethylene and $R_{40}$ and $A_{40}$ are preferably 1,1-dimethylethylene.

An example of $C_4$–$C_{10}$alkanetetrayl is 1,2,3,4-butanetetrayl.

An example of $C_5$–$C_7$cycloalkylene is cyclohexylene.

An example of $C_1$–$C_4$alkylenedi($C_5$–$C_7$cycloalkylene) is methylenedicyclohexylene.

Where the radicals $R_{11}$, $R_{12}$, $R_{13}$ or $A_{11}$, $A_{12}$ and $A_{13}$, together with the nitrogen atoms to which they are attached, form a 5- to 10-membered heterocyclic ring, this ring is for example

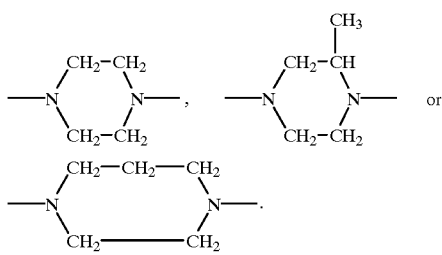

A 6-membered heterocyclic ring is preferred.

Where the radicals $R_{14}$ and $R_{15}$ or $A_{14}$ and $A_{15}$, together with the nitrogen atom to which they are attached, form a 5- to 10-membered heterocyclic ring, this ring is for example 1-pyrrolidyl, piperidino, morpholino, 1-piperazinyl, 4-methyl1-piperazinyl, 1-hexahydroazepinyl, 5,5,7-trimethyl1-homopiperazinyl or 4,5,5,7-tetramethyl-1-homopiperazinyl. Morpholino is particularly preferred.

One of the preferred definitions of $R_{23}$, $R_{27}$, $A_{23}$ and $A_{27}$ is phenyl.

$Y_2$, $E_2$, $R_{37}$ and $A_{37}$ are preferably a direct bond.

One of the preferred definitions of $Y_1$, $Y_3$, $E_1$, $E_3$, $A_1$, $A_9$, $A_{10}$, $A_{18}$, $A_{20}$, $A_{22}$, $A_{30}$, $A_{31}A_{35}$, $A_{41}$ and $A_{42}$ is hydrogen.

$n_2$ and $b_2$ are preferably 2–25.

$n_3$ and $b_3$ are preferably 1–25, especially 2–20 or 2–10.

$n_4'$, $n_4''$, $n_4'''$, $b_4'$, $b_4''$ and $b_4'''$ are preferably 2–4.

$n_5$ and $b_5$ are preferably 1–25, especially 1–20 or 1–10.

$n_6$ and $b_6$ are preferably 2–25, especially 2–20 or 2–10.

$n_7$ and $b_7$ are preferably 1–25, especially 1–20 or 2–10.

$b_8$ is preferably 2–25, especially 2–20 or 2–10.

In a stabilizer mixture comprising component I-a) and component II-b) or II-m), $R_1$ is preferably other than $C_1$–$C_{18}$alkyl, especially other than hydrogen and $C_1$–$C_{18}$alkyl.

In a stabilizer mixture comprising component I-a) and component II-d), if $R_1$=$C_1$–$C_{18}$alkyl, the group —N($A_{14}$)$A_{15}$ is preferably morpholino.

In a stabilizer mixture comprising component I-a) and component II-d), the group —N($A_{14}$)$A_{15}$ is in particular morpholino.

The compounds described as components II-a) to II-m) are essentially known (in some cases commercially available) and can be prepared by known processes as described, for example, in U.S. Pat. No. 3,640,928, U.S. Pat. No. 4,108,829, U.S. Pat. No. 3,925,376, U.S. Pat. No. 4,086,204, U.S. Pat. No. 4,331,586, U.S. Pat. No. 5,051,458, U.S. Pat. No. 4,477,615 and Chemical Abstracts—CAS No. 136 504-96-6, U.S. Pat. No. 4,857,595, DD-A-262 439 (Derwent 89-122 983/17, Chemical Abstracts 111:58 964u), WO-A-94/12 544 (Derwent 94–177 274/22), U.S. Pat. No. 4,356,307, U.S. Pat. No. 4,340,534, U.S. Pat. No. 4,408,051, U.S. Pat. No. 4,689,416, U.S. Pat. No. 4,110,334, U.S. 4,529,760, U.S. Pat. No. 5,182,390 (Chemical Abstracts—CAS No. 144 923-25-1) and U.S. Pat. No. 4,233,412.

Component II-f) can be prepared analogously to known processes, for example by reacting a polyamine of formula VIII-2-a with cyanuric chloride in a molar ratio of from 1:2 to 1:4 in the presence of anhydrous lithium carbonate, sodium carbonate or potassium carbonate in an organic solvent such as 1,2-dichloroethane, toluene, xylene, benzene, dioxane or tert-amyl alcohol at a temperature of from −20° C. to +10° C., preferably from −10° C. to +10° C., in particular from 0° C. to +10° C., for from 2 to 8 hours, followed by reaction of the resultant product with a 2,2,6,6-tetramethyl-4-piperidylamine of the formula VIII-2-b. The molar ratio of 2,2,6,6-tetramethyl-4-piperidylamine to polyamine of the formula VIII-2-a employed is for example from 4:1 to 8:1. The quantity of 2,2,6,6-tetramethyl-4-piperidylamine can be added in one portion or in more than one portion at intervals of a few hours.

The ratio of polyamine of the formula VIII-2-a to cyanuric chloride to 2,2,6,6-tetramethyl-4-piperidylamine of the formula VIII-2-b is preferably from 1:3:5 to 1:3:6.

The following example indicates one way of preparing the preferred component II-f).

EXAMPLE 23.6 g (0.128 mol) of cyanuric chloride, 7.43 g (0.0426 mol) of N,N'-bis[3-aminopropyl]ethylenediamine and 18 g (0.13 mol) of anhydrous potassium carbonate are reacted at 5° C. for 3 hours with stirring in 250 ml of 1,2-dichloroethane. The mixture is warmed at room temperature for a further 4 hours. 27.2 g (0.128 mol) of N-(2,2,6,6-tetramethyl-4-piperidyl)butylamine are added and the resultant mixture is warmed at 60° C. for 2 hours. A further 18 g (0.13 mol) of anhydrous potassium carbonate are added and the mixture is warmed at 60° C. for a further 6 hours. The solvent is removed by distillation under a slight vacuum (200 mbar) and replaced by xylene. 18.2 g (0.085 mol) of N-(2,2,6,6-tetramethyl-4-piperidyl)butylamine and 5.2 g (0.13 mol) of ground sodium hydroxide are added, the mixture is heated at reflux for 2 hours and, for a further 12 hours, the water formed during the reaction is removed by azeotropic distillation. The mixture is filtered. The solution is washed with water and dried over $Na_2SO_4$. The solvent is evaporated and the residue is dried at 120–130° C. in vacuo (0.1 mbar). Component II-f) is obtained as a colourless resin.

In general, component II-f) can for example be represented by a compound of the formula VIII-2-1, VIII-2-2 or VIII-2-3. It can also be in the form of a mixture of these three compounds.

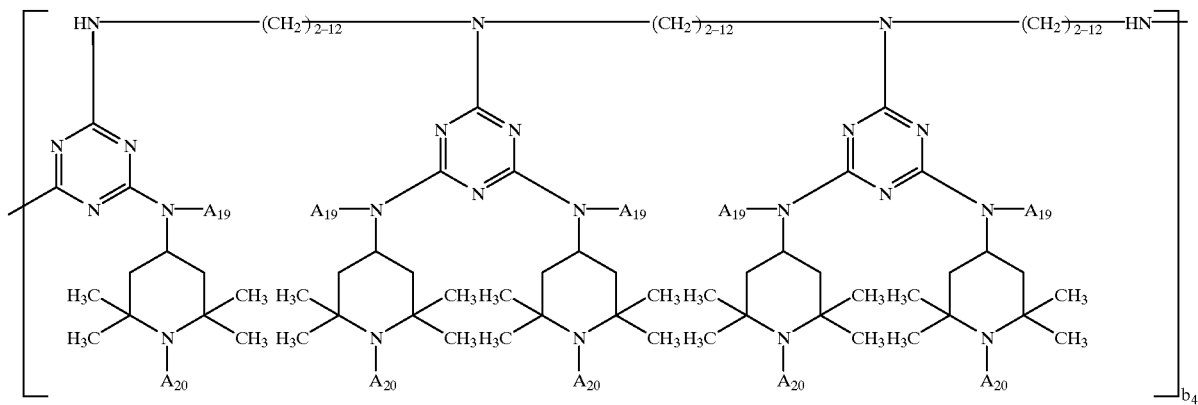
(VIII-2-1)
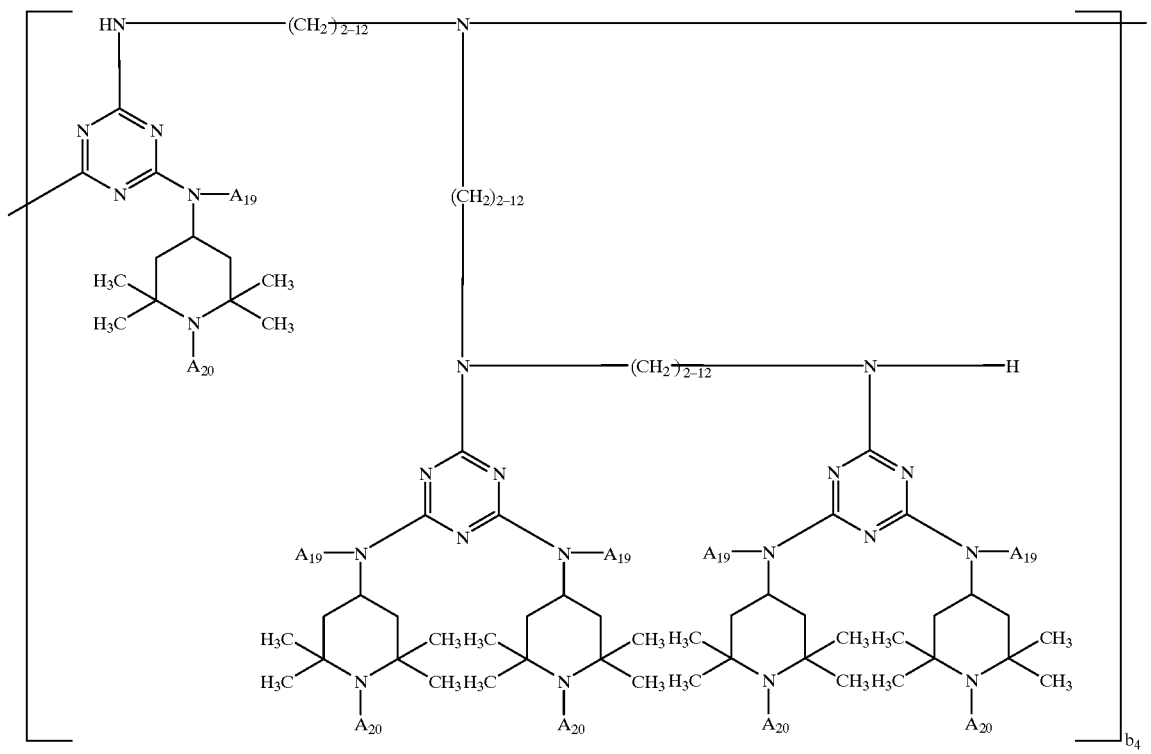
(VIII-2-2)

(VIII-2–3)
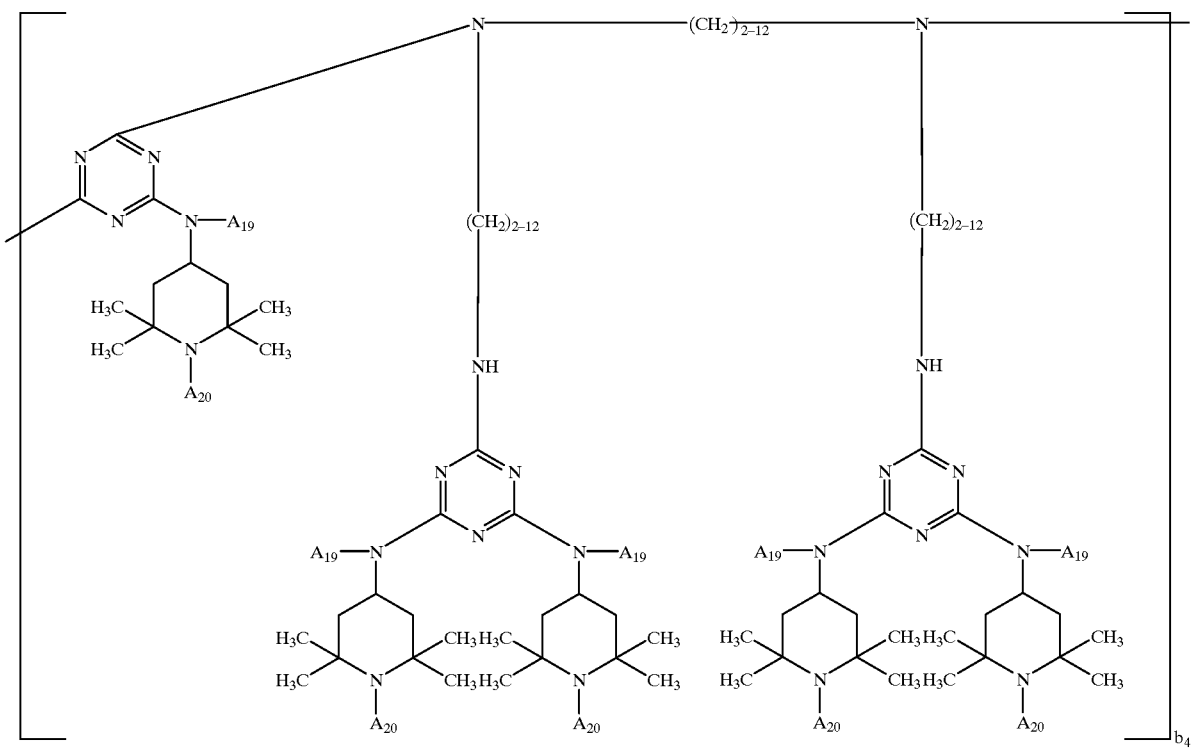
A preferred definition of the formula VIII-2-1 is
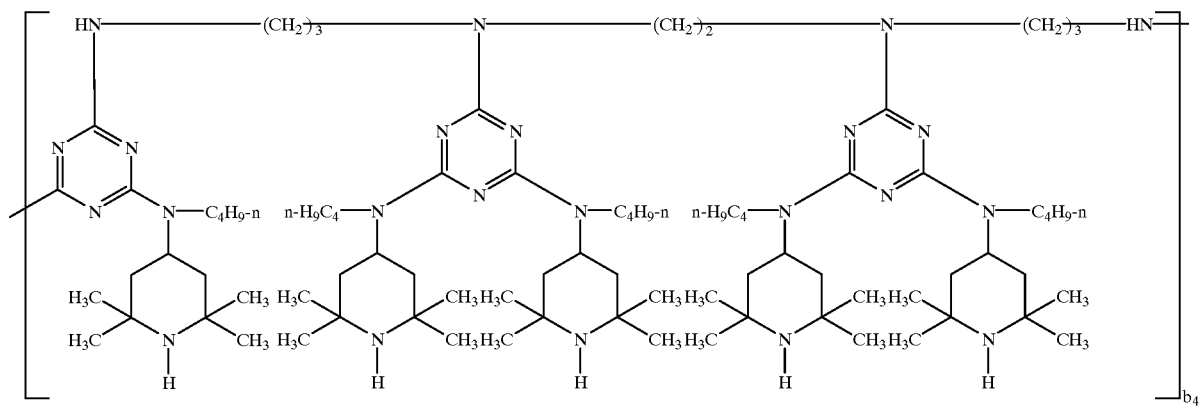

A preferred definition of the formula VIII-2-2 is
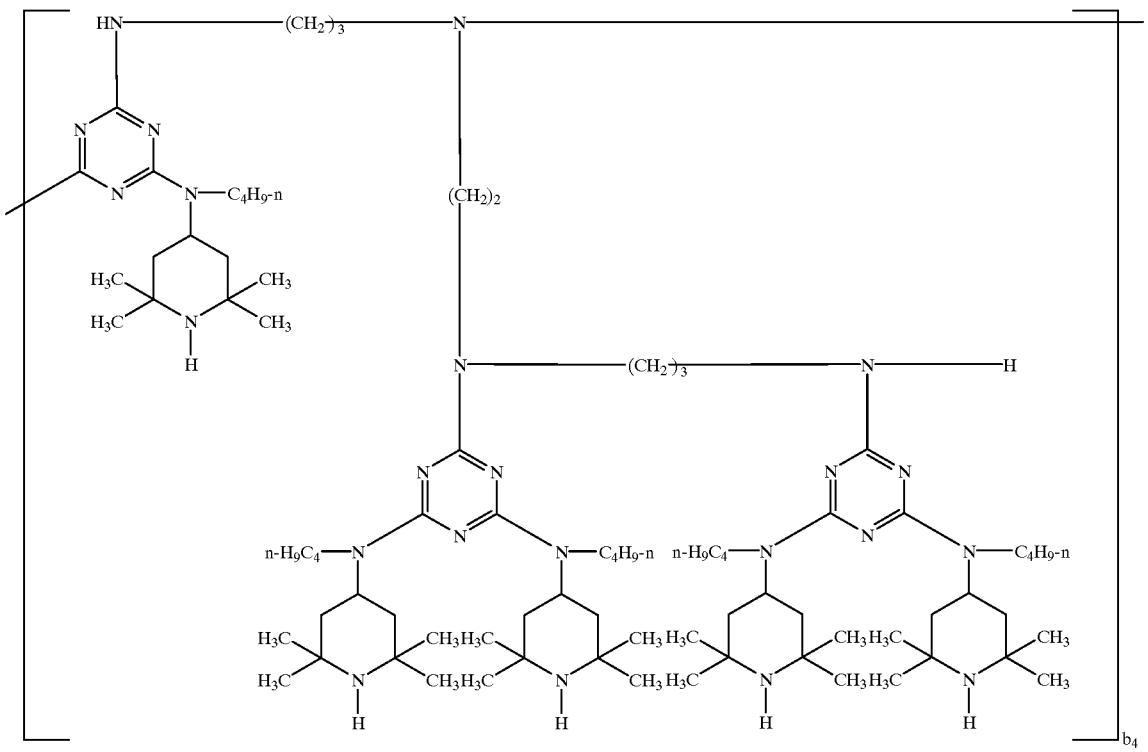
A preferred definition of the formula VIII-2-3 is
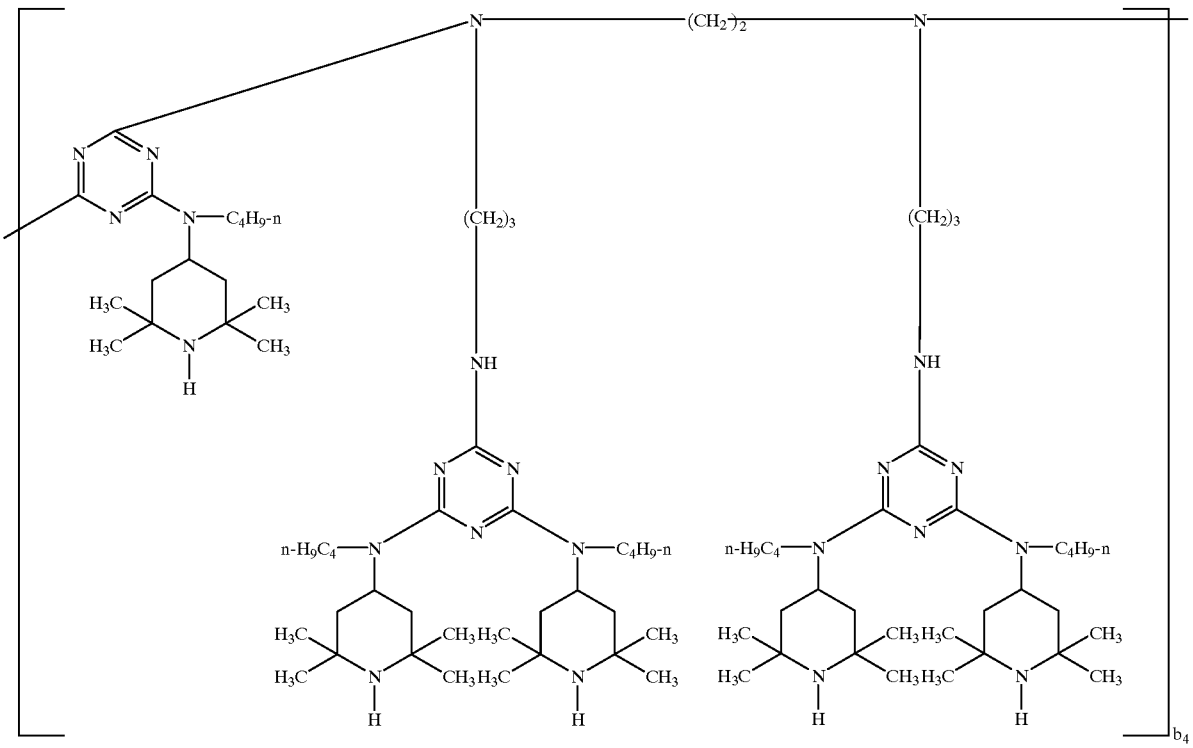

In the above formulae VIII-2-1, VIII-2-2 and VIII-2-3, $b_4$ is preferably from 1 to 20.

The compounds described as components I-a) to I-l) can be prepared from the compounds described as components II-a) to II-l)—the nitrogen atom in the 2,2,6,6-tetramethylpiperid-4-yl group being unsubstituted—in analogy to known processes, for example as disclosed in U.S. Pat. No. 5,204,473, by oxidizing the corresponding 2,2,6,6-tetramethylpiperidine derivative with an appropriate peroxy compound, such as hydrogen peroxide or tert-butyl hydroperoxide, in the presence of a metal carbonyl or metal oxide catalyst, followed by reduction of the resulting oxyl intermediate to the desired N-hydroxyl derivative, preferably by catalytic hydrogenation.

After this, the O-alkyl derivatives can be synthesized in various ways. For example, the N-hydroxy derivative can be alkylated with sodium hydride and halogenated hydrocarbons, such as ethyl iodide. N-Methoxy variants can be prepared by thermolysis of a chlorobenzene solution of the nitroxyl radical and of di-tert-butyl peroxide. The product is formed by a coupling reaction between the nitroxyl radical and the methyl radical which is produced from the β-cleavage of a tert-butoxy radical.

Other N-alkoxy variants can be synthesized by coupling of nitroxyl radicals with hydrocarbon radicals, which are formed during the thermal decomposition of di-tert-butyl peroxide in the presence of hydrocarbon solvents, such as cyclohexane, toluene and ethylbenzene.

Although these procedures have been described with reference to N-alkoxy substituents, it will be understood that they can be employed equally to all $OR_1$ groups.

For example, 1-cycloalkyloxy-2,2,6,6-tetramethylpiperid-4-yl derivatives can be prepared by reacting the corresponding 2,2,6,6-tetramethylpiperid-4-yl derivative with tert-butyl hydroperoxide in the presence of $MoO_3$ and a cycloalkane.

In general, component I-f) can for example also be represented by a compound of the formula VIII-2-1, VIII-2-2 or VIII-2-3 in which the radicals $A_{20}$ are a group —$OR_{20}$. It can also be in the form of a mixture of these three compounds.

The product described as component I-f) is, for example, also obtainable by reacting a product, obtained by reaction of a polyamine of the formula VIII-1-a with cyanuric chloride, with a compound of the formula VIII-1-b $$H_2N-(CH_2)_{\overline{n_4'}}-NH-(CH_2)_{\overline{n_4''}}-NH-(CH_2)_{\overline{n_4'''}}-NH_2 \quad \text{(VIII-1-a)}$$

(VIII-1-b)

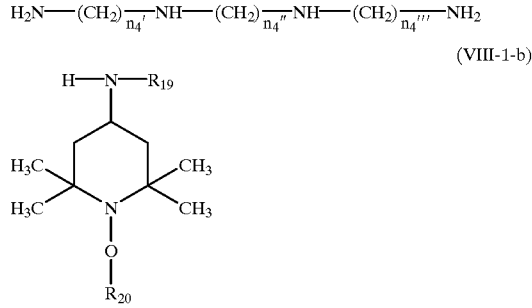

in which $n_4'$, $n_4''$ and $n_4'''$ independently of one another are a number from 2 to 12, $R_{19}$ is hydrogen, $C_1$–$C_{12}$alkyl, $C_5$–$C_{12}$cycloalkyl, phenyl or $C_7$–$C_9$phenylalkyl and $R_{20}$ is as defined for $R_1$.

The reaction can take place, for example, in analogy to the preparation process described in U.S. Pat. No. 4,477,615.

With particular preference, component I-a) is ®TINUVIN 123, component II-a) is ®MARK LA 52 or ®MARK LA 57, component II-b) is ®CHIMASSORB 119, component II-d) is ®CHIMASSORB 944, ®CYASORB UV 3346 or ®DASTIB 1082, component II-e) is ®UVASIL 299 or ®UVASIL 125, component II-f) is ®UVASORB HA 88, component II-g) is ®UVINUL 5050 H, ®LICHTSCHUTZSTOFF UV 31 or ®LUCHEM HA-B 18, component II-i) is ®HOSTAVIN N 30, component II-k) is ®MARK LA 63 or ®MARK LA 68 and component II-m) is ®TINUVIN 622.

Other products which can be employed, for example, are as component II-a) ®Tinuvin 770 or ®DASTIB 845, as component II-h) ®LICHTSCHUTZMITTEL S 95 and as component II-j) ®HOSTAVIN N 20 or ®SANDUVOR 3050.

As component I-f) it is preferred to employ ®UVASORB HA 88, in which the 2,2,6,6-tetramethylpiperidin-4-yl radicals are replaced by a group of the formula VIII-1-c.

If the radical $A_{31}$ in the compound of the formula XI-2 is hydrogen, this compound can be in the form of a mixture with a compound of the formula XI-2*

(XI-2*)

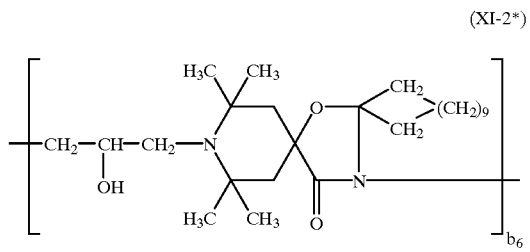

and can also be employed as such a mixture, as component II-i), in the stabilizer system of the invention. The ratio of XI-2: XI-2* is for example from 20:1 to 1:20 or from 1:10 to 10:1.

The definitions of the terminal groups which saturate the free valences in the compounds of the formulae VI-1, VI-2, VII-1, VII-2, VIII-2-1, VIII-2-2, VIII-2-3, IX-1, XI-2, XI-1, XI-2, XI-2*, XIII-1, XIII-2 and XVI-2 depend on the processes used for their preparation. The terminal groups can also be modified after the preparation of the compounds.

If the compounds of the formula VI-1 are prepared by reacting a compound of the formula

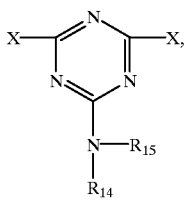

in which X is for example halogen, especially chlorine, and $R_{14}$ and $R_{15}$ are as defined above, with a compound of the formula

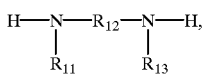

in which $R_{11}$, $R_{12}$ and $R_{13}$ are as defined above, then the terminal group bonded to the diamino radical is hydrogen or

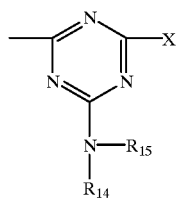

and the terminal group bonded to the triazine radical is X or

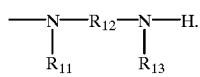

If X is a halogen, it is advantageous to replace it, for example, by —OH or an amino group when the reaction is complete. Examples of amino groups which may be mentioned are pyrrolidin-1-yl, morpholino, —NH$_2$, —N(C$_1$–C$_8$alkyl)$_2$ and —NR(C$_1$–C$_8$alkyl), in which R is hydrogen or a group of the formula IV-1.

The comments made above regarding the compounds of the formula VI-1 can be applied correspondingly to the compounds of the formula VI-2, the radicals $R_{11}$, $R_{12}$, $R_{13}$, $R_{14}$ and $R_{15}$ corresponding to the respective radicals $A_{11}$, $A_{12}$, $A_{13}$, $A_{14}$ and $A_{15}$ and the group IV-1 corresponding to the group IV-2.

In the compounds of the formula VII-1 or VII-2 the terminal group bonded to the silicon atom can for example be $(R_{16})_3$Si—O— or $(A_{16})_3$Si—O— and the terminal group bonded to the oxygen can for example be —Si$(R_{16})_3$ or —Si$(A_{16})_3$.

The compounds of the formulae VII-1 and VII-2 can also be in the form of cyclic compounds if $n_3$ or $b_3$ is a number from 3 to 10; in other words, the free valences represented in the structural formulae in that case form a direct bond.

In the compounds of the formulae VIII-2-1, VIII-2-2 and VIII-2-3 the terminal group bonded to the triazine radical is for example Cl or a group

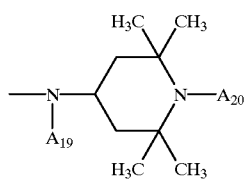

and the terminal group bonded to the amino radical is for example hydrogen or a group

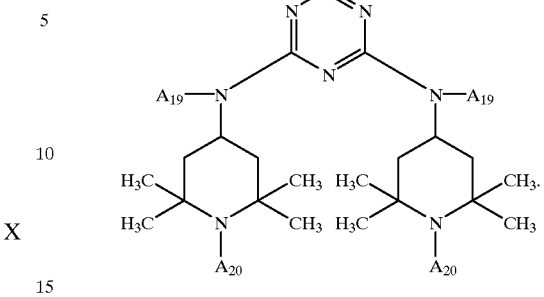

In the compounds of the formula IX-1, the terminal group bonded to the 2,5-dioxopyrrolidine ring is for example hydrogen and the terminal group bonded to the radical —C($R_{27}$)($R_{28}$)— is for example

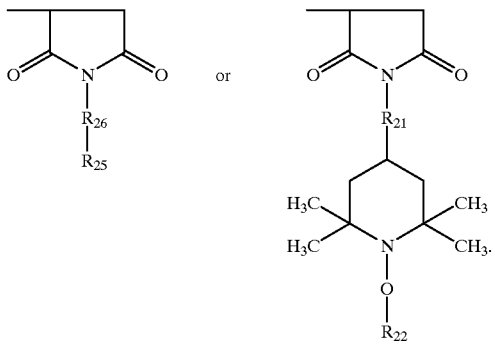

In the compounds of the formula IX-2 the terminal group bonded to the 2,5-dioxopyrrolidine ring is for example hydrogen and the terminal group bonded to the radical —C($A_{27}$)($A_{28}$)— is for example

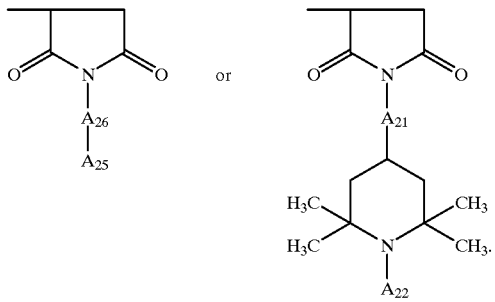

In the compounds of the formula XI-1 and XI-2 the terminal group bonded to the dimethylene radical can for example be —OH and the terminal group bonded to the oxygen can for example be hydrogen. The terminal groups can also be polyether radicals.

In the compounds of the formula XI-2*, the terminal group bonded to the nitrogen can for example be hydrogen and the terminal group bonded to the 2-hydroxypropylene radical can for example be a group

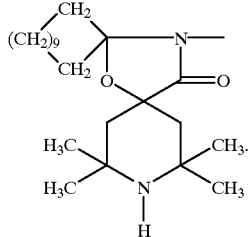

In the compounds of the formula XIII-1, the terminal group bonded to the carbonyl radical is for example

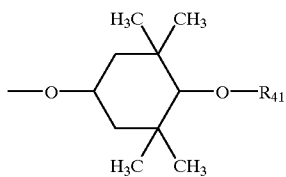

and the terminal group bonded to the oxygen radical is for example

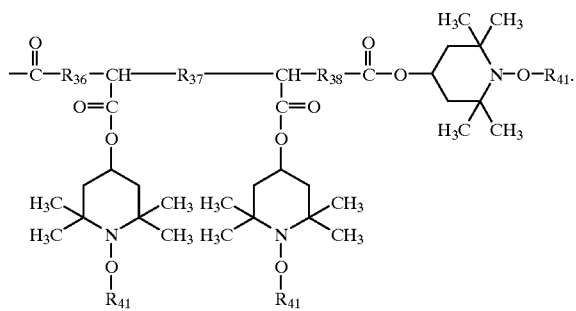

In the compounds of the formula XIII-2 the terminal group bonded to the carbonyl radical is for example

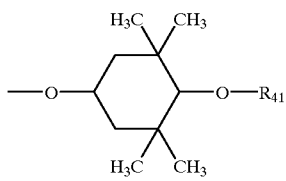

and the terminal group bonded to the oxygen radical is for example

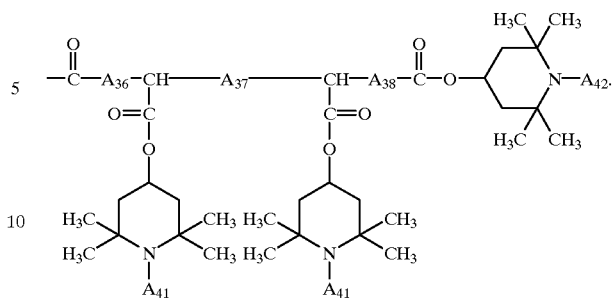

Where the preparation of the compounds of the formula XVI-2 takes place, for example, by reacting a compound of the formula

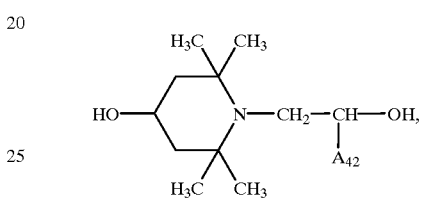

in which $A_{42}$ is as defined above, with a dicarboxylic diester of the formula Q—OOC—$A_{43}$—COO—Q, in which Q is for example methyl, ethyl or propyl and $A_{43}$ is as defined above, the terminal group bonded to the 2,2,6,6-tetramethyl-4-oxypiperid-1-yl radical is hydrogen or —CO—$A_{43}$—COO—Q and the terminal group bonded to the diacyl radical is —O—Q or

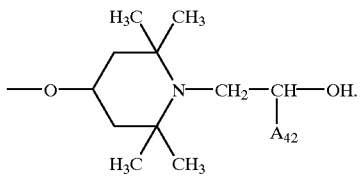

A preferred stabilizer mixture is one in which $R_1$, $R_9$, $R_{10}$, $R_{18}$, $R_{20}$, $R_{22}$, $R_{30}$, $R_{31}$, $R_{35}$ and $R_{41}$ independently of one another are $C_1$–$C_{12}$alkyl, $C_5$–$C_8$cycloalkyl or methyl-substituted $C_5$–$C_8$cycloalkyl.

Preference is likewise given to a stabilizer mixture in which $R_1$, $R_9$, $R_{10}$, $R_{18}$, $R_{20}$, $R_{22}$, $R_{30}$, $R_{31}$, $R_{35}$ and $R_{41}$ independently of one another are methyl, octyl or cyclohexyl.

Also of interest is a stabilizer mixture in which $A_1$, $A_9$, $A_{10}$, $A_{18}$, $A_{20}$, $A_{22}$, $A_{30}$, $A_{31}$, $A_{35}$ and $A_{41}$ independently of one another are hydrogen or methyl.

A preferred embodiment corresponds also to a stabilizer mixture comprising a component I-a), I-b), I-c), I-d), I-e), I-f), I-g), I-h), I-i), I-j), I-k) or I-l) and a component II-a), II-b), II-d), II-e), II-f), II-g), II-i), II-k) or II-m).

The following stabilizer mixtures may be mentioned as examples:

1. stabilizer mixture comprising a component I-a) and a component II-b), II-d) or II-m),
2. stabilizer mixture comprising a component I-b) and a component II-b), II-d) or II-m) and
3. stabilizer mixture comprising a component I-c) and a component II-b), II-d) or II-m).

Also preferred is a stabilizer mixture
in which $n_1$ is 1, 2 or 4,
if $n_1$ is 1, $R_2$ is $C_{10}$–$C_{20}$alkyl,
if $n_1$ is 2, $R_2$ is $C_6$–$C_{10}$alkylene and
if $n_1$ is 4, $R_2$ is butanetetrayl;
$R_3$ and $R_7$ independently of one another are hydrogen or $C_1$–$C_4$alkyl,
$R_4$, $R_5$ and $R_6$ independently of one another are $C_2$–$C_6$alkylene,
$R_8$ is hydrogen, $C_1$–$C_6$alkyl, $C_5$–$C_8$cycloalkyl, methyl-substituted $C_5$–$C_8$cycloalkyl, phenyl, $C_7$–$C_9$phenylalkyl or a group of the formula IV-1;
$R_{11}$, $R_{13}$, $R_{14}$ and $R_{15}$ independently of one another are hydrogen, $C_1$–$C_8$alkyl, $C_5$–$C_8$cycloalkyl, methyl-substituted $C_5$–$C_8$cycloalkyl, phenyl, $C_7$–$C_9$phenylalkyl or a group of the formula IV-1, or
the radicals $R_{14}$ and $R_{15}$, together with the nitrogen atom to which they are attached, form a 6-membered heterocyclic ring,
$R_{12}$ is $C_2$–$C_{10}$alkylene and
$n_2$ is a number from 2 to 25;
$R_{16}$ is $C_1$–$C_4$alkyl, $C_5$–$C_8$cycloalkyl or phenyl,
$n_4'$, $n_4''$ and $n_4'''$ independently of one another are a number from 2 to 4 and
$R_{19}$ is $C_1$–$C_4$alkyl;
$R_{21}$ and $R_{26}$ independently of one another are a direct bond or a group —N($Y_1$)—CO—$Y_2$—CO—N($Y_3$)—,
$Y_1$ and $Y_3$ independently of one another are hydrogen or $C_1$–$C_4$alkyl,
$Y_2$ is a direct bond,
$R_{23}$ and $R_{27}$ are $C_1$–$C_{25}$alkyl or phenyl,
$R_{24}$ and $R_{28}$ are hydrogen or $C_1$–$C_4$alkyl,
$R_{25}$ is $C_1$–$C_{25}$alkyl or a group of the formula IV-1 and
$n_5$ is a number from 1 to 25;
$R_{29}$ is $C_8$–$C_{15}$alkyl;
$n_6$ is a number from 2 to 25;
$R_{32}$ and $R_{33}$ together form $C_8$–$C_{14}$alkylene,
$R_{34}$ is hydrogen or a group —$Z_1$—COO—$Z_2$,
$Z_1$ is $C_2$–$C_6$alkylene and
$Z_2$ is $C_8$–$C_{15}$alkyl;
$R_{36}$, $R_{38}$, $R_{39}$ and $R_{40}$ independently of one another are $C_1$–$C_4$alkylene,
$R_{37}$ is a direct bond and
$n_7$ is a number from 1 to 25.

Particular preference is given to a stabilizer mixture in which component I-a) is at least one compound of the formula I-1-a-1, I-1-a-2 or I-1-a-3

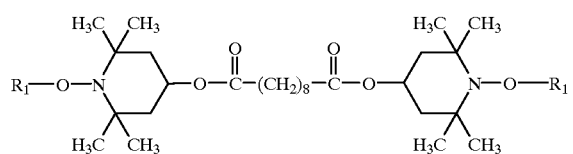
(I-1-a-1)

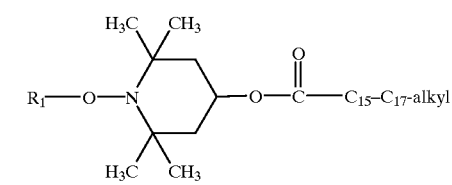
(I-1-a-2)

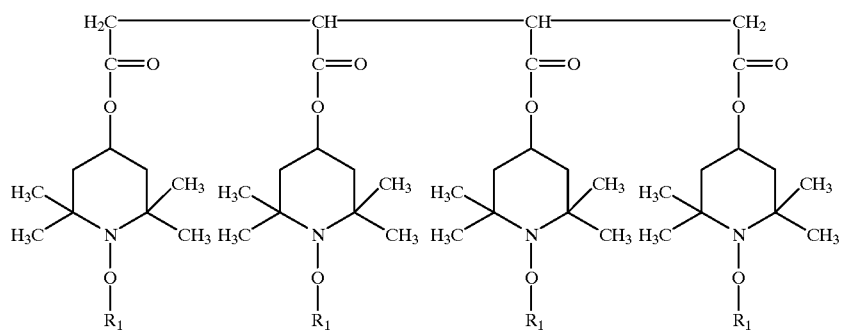
(I-1-a-3)

$R_{17}$ is $C_3$–$C_6$alkylene and
$n_3$ is a number from 1 to 25;

in which $R_1$ is methyl, octyl or cyclohexyl;
component I-b) is at least one compound of the formula II-1-b (II-1-b)
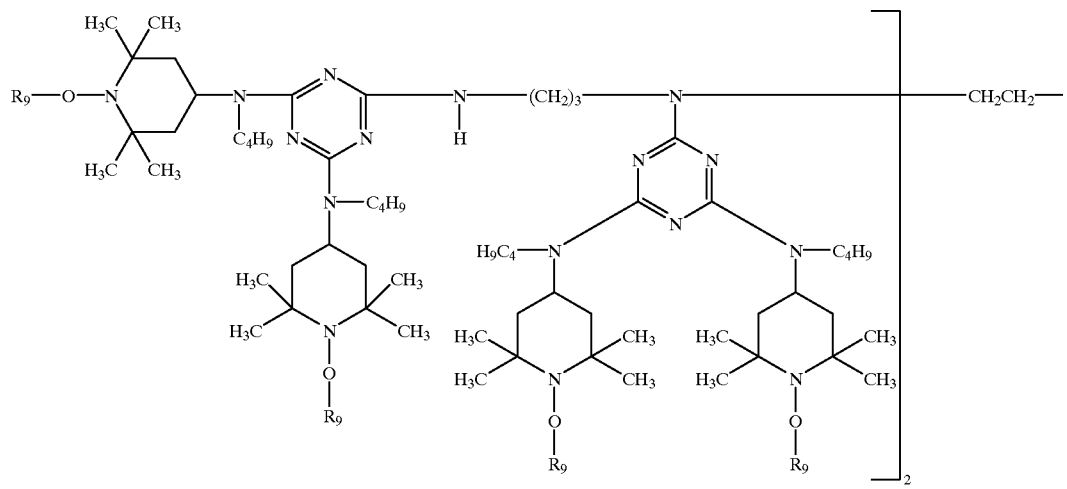
in which $R_9$ is as defined for $R_1$;
component I-c) is at least one compound of the formula V-1-c
(V-1-c)
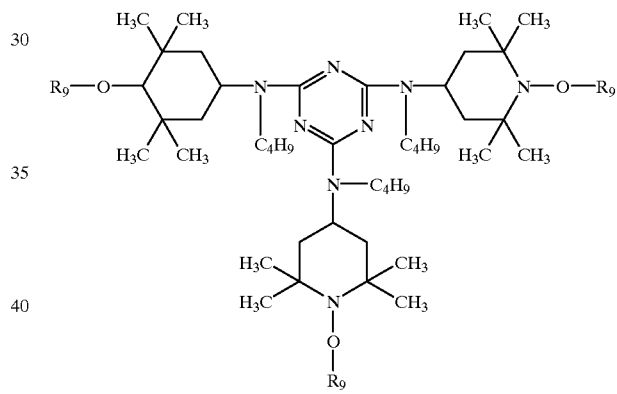
in which $R_9$ is as defined above;
component I-d) is at least one compound of the formula VI-1-d-1, VI-1-d-2 or VI-1-d-3
(VI-1-d-1)
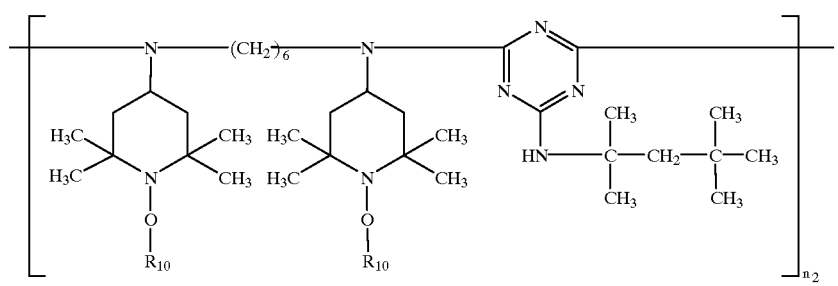

-continued

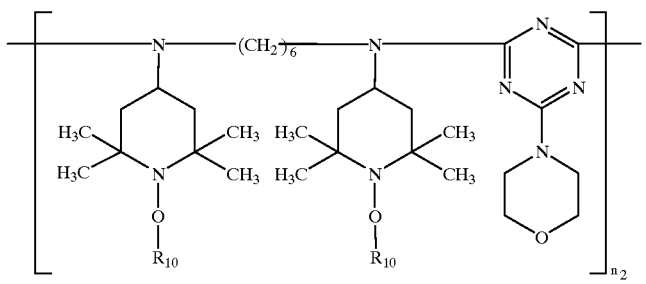
(VI-1-d-2)

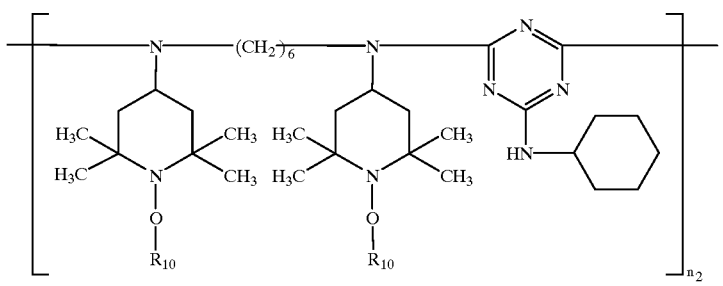
(VI-1-d-3)

in which $R_{10}$ is as defined for $R_1$ and $n_2$ is a number from 2 to 25;

component I-e) is at least one compound of the formula VII-1-e

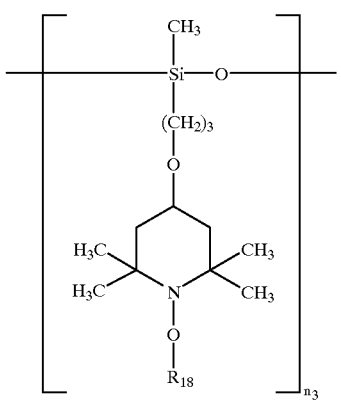
(VII-1-e)

in which $R_{18}$ is as defined for $R_1$ and $n_3$ is a number from 1 to 25;

component I-f) is a product obtainable by a) reacting a product, obtained by reaction of a polyamine of the formula

with cyanuric chloride, with a compound of the formula

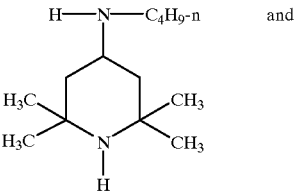
and b) further reacting the 2,2,6,6-tetramethylpiperid-4-yl groups which are present in the molecule to give groups of the formula VIII-1-c;

component 1-g) is at least one compound of the formula IX-1-g-1, IX-1-g-2 or IX-1-g-3

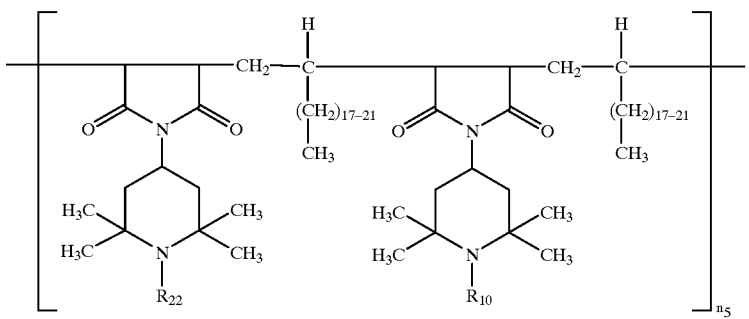
(IX-1-g-1)
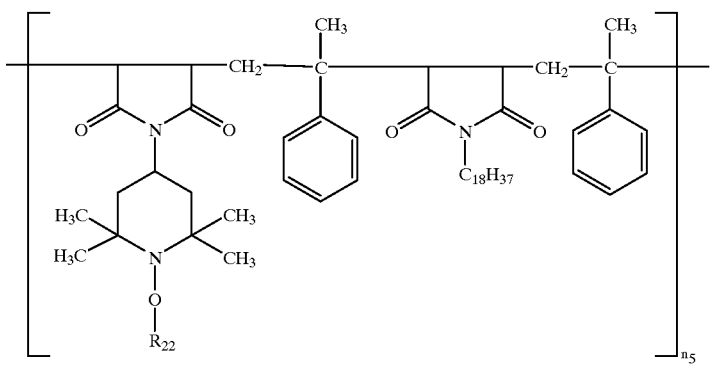
(IX-1-g-2)
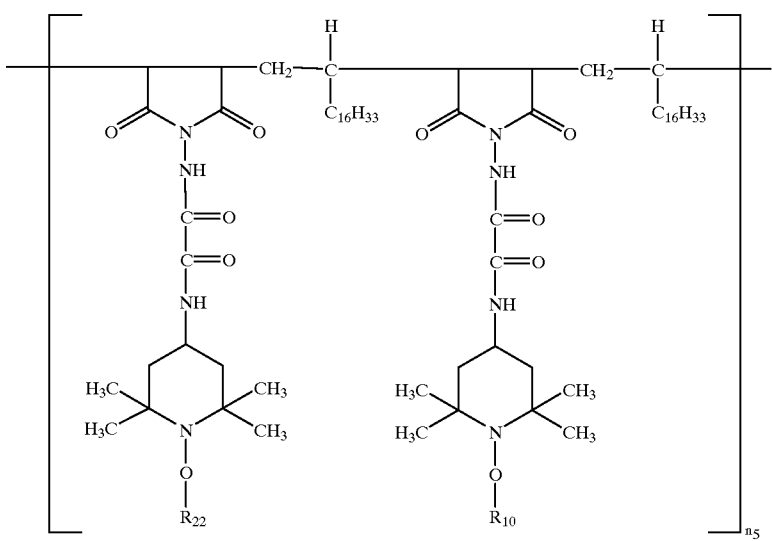
(IX-1-g-3)

in which $R_{10}$ and $R_{22}$ are as defined for $R_1$ and $n_5$ is a number from 1 to 25;

component 1-h) is at least one compound of the formula X-1-h

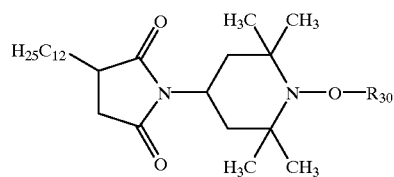

(X-1-h)

in which $R_{30}$ is as defined for $R_1$;

component I-i) is at least one compound of the formula (XI-1) in which $R_{31}$ is as defined for $R_1$ and $n_6$ is a number from 2 to 25;

component I-j) is at least one compound of the formula XII-1-j-1 or XII-1-j-2

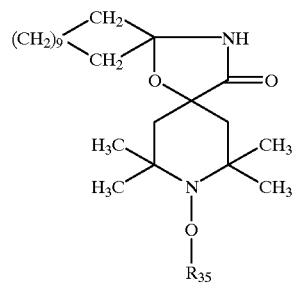

(XII-1-j-1)

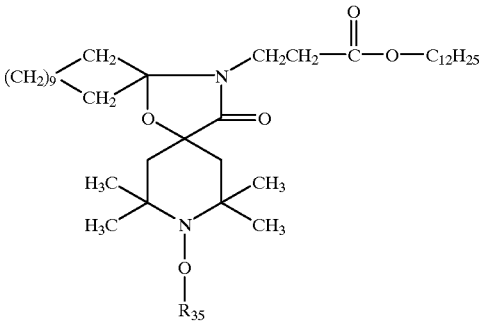

(XII-1-j-2)

in which $R_{35}$ is as defined for $R_1$;

component I-k) is at least one compound of the formula XIII-1-k

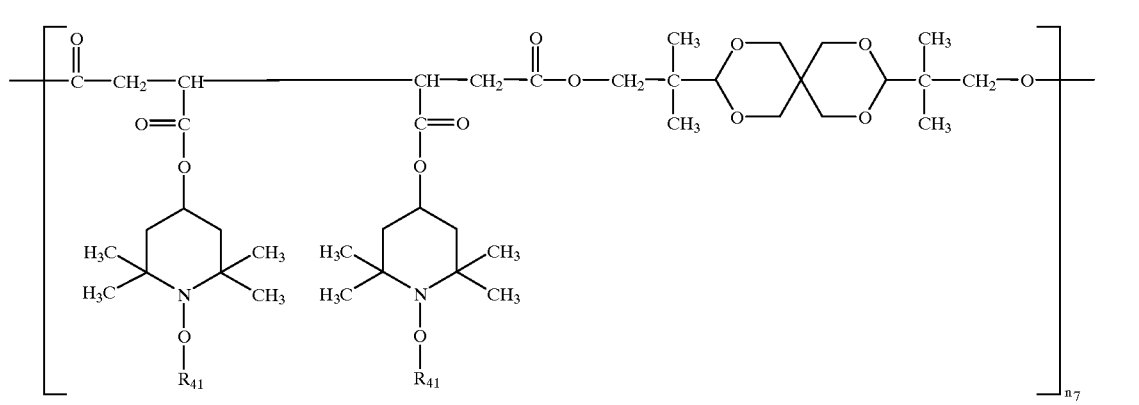

(XIII-1-k)

in which $R_{41}$ is as defined for $R_1$ and $n_7$ is a number from 1 to 25;

component I-k) is at least one compound of the formula XIV-1-l

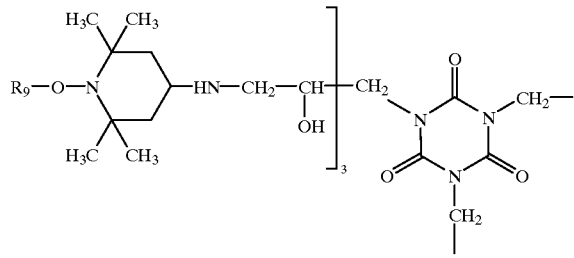

(XIV-1-l)

in which $R_9$ is as defined for $R_1$.

Preference is furthermore given to a stabilizer mixture in which $b_1$ is 1, 2 or 4, if $b_1$ is 1, $A_2$ is $C_{10}$–$C_{20}$alkyl, if $b_1$ is 2, $A_2$ is $C_6$–$C_{10}$alkylene and if $b_1$ is 4, $A_2$ is butanetetrayl;

$A_3$ and $A_7$ independently of one another are hydrogen or $C_1$–$C_4$alkyl, $A_4$, $A_5$ and $A_6$ independently of one another are $C_2$–$C_6$alkylene, $A_8$ is hydrogen, $C_1$–$C_6$alkyl, $C_5$–$C_8$cycloalkyl, methyl-substituted $C_5$–$C_8$cycloalkyl, phenyl, $C_7$–$C_9$phenylalkyl or a group of the formula IV-2;

$A_{11}$, $A_{13}$, $A_{14}$ and $A_{15}$ independently of one another are hydrogen, $C_1$–$C_8$alkyl, $C_5$–$C_8$cycloalkyl, methyl-substituted $C_5$–$C_8$cycloalkyl, phenyl, $C_7$–$C_9$phenylalkyl or a group of the formula IV-2, or the radicals $A_{14}$ and $A_{15}$, together with the nitrogen atom to which they are attached, form a 6-membered heterocyclic ring, $A_{12}$ is $C_2$–$C_{10}$alkylene and $b_2$ is a number from 2 to 25;

$A_{16}$ is $C_1$–$C_4$alkyl, $C_5$–$C_8$cycloalkyl or phenyl, $A_{17}$ is $C_3$–$C_6$alkylene and $b_3$ is a number from 1 to 25;

$b_4'$, $b_4''$ and $b_4'''$ independently of one another are a number from 2 to 4 and $A_{19}$ is $C_1$–$C_4$alkyl;

$A_{21}$ and $A_{26}$ independently of one another are a direct bond or a group —N($E_1$)—CO—$E_2$—CO—N($E_3$)—, $E_1$ and $E_3$ independently of one another are hydrogen or $C_1$–$C_4$alkyl, $E_2$ is a direct bond, $A_{23}$ and $A_{27}$ are $C_1$–$C_{25}$alkyl or phenyl, $A_{24}$ and $A_{28}$ are hydrogen or $C_1$–$C_4$alkyl, $A_{25}$ is $C_1$–$C_{25}$alkyl or a group of the formula IV-2 and $b_5$ is a number from 1 to 25;

$A_{29}$ is $C_8$–$C_{15}$alkyl;

$b_6$ is a number from 2 to 25;

$A_{32}$ and $A_{33}$ together form $C_8$–$C_{14}$alkylene, $A_{34}$ is hydrogen or a group —$G_1$—COO—$G_2$, $G_1$ is $C_2$–$C_6$alkylene and $G_2$ is $C_8$–$C_{15}$alkyl;

$A_{36}$, $A_{38}$, $A_{39}$ and $A_{40}$ independently of one another are $C_1$–$C_4$alkylene, $A_{37}$ is a direct bond and $b_7$ is a number from 1 to 25.

Particular preference is given to a stabilizer mixture in which component II-a) is at least one compound of the formula I-2-a-3

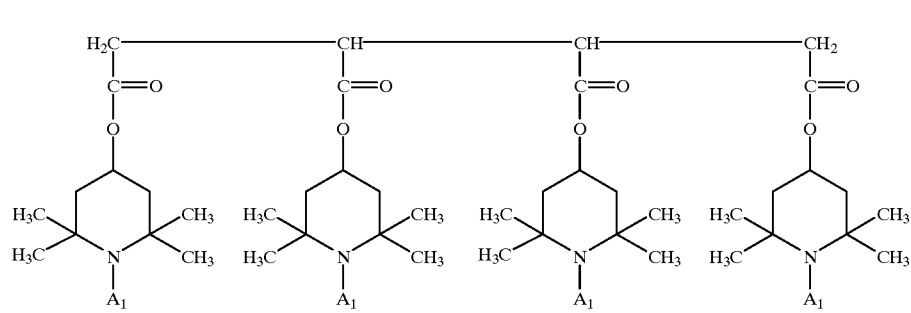

(I-2-a-3)

in which $A_1$ is hydrogen or methyl;

component II-b) is at least one compound of the formula II-2-b

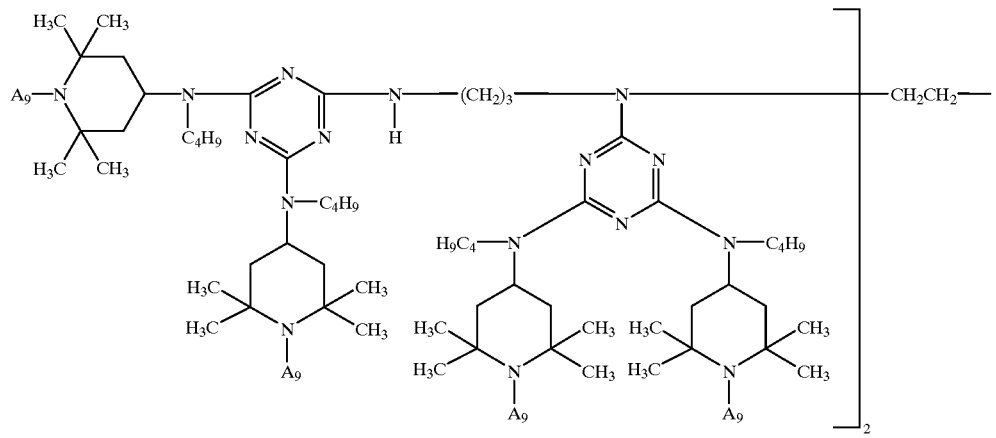

(II-2-b)

in which $A_9$ is as defined for $A_1$;

component II-d) is at least one compound of the formula VI-2-d-1, VI-2-d-2 or VI-2-d-3

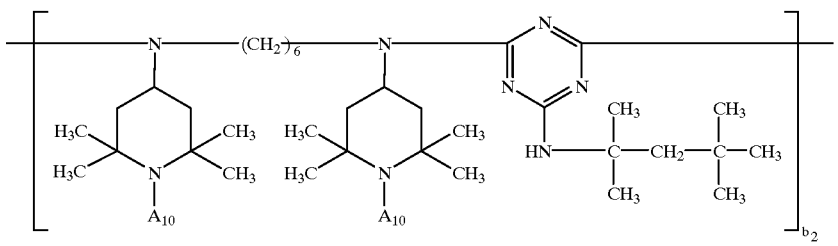
(VI-2-d-1)

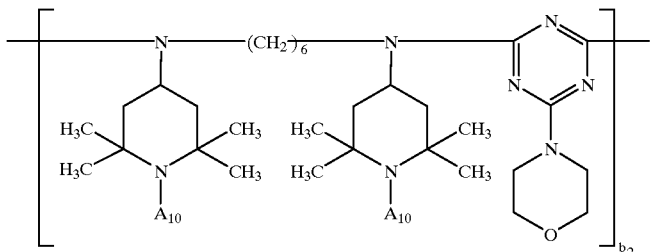
(VI-2-d-2)

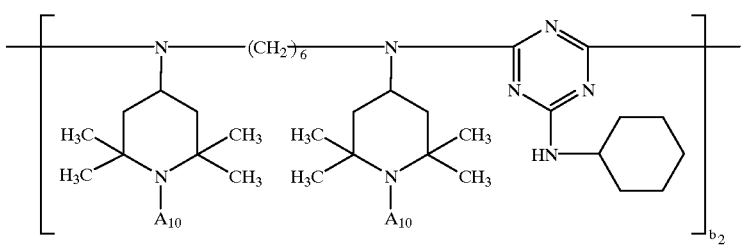
(VI-2-d-3)

in which $A_{10}$ is as defined for $A_1$ and $b_2$ is a number from 2 to 25;

component II-e) is at least one compound of the formula VI-2-e

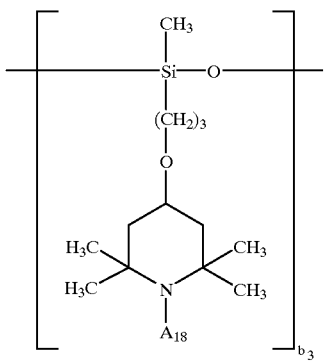
(VI-2-e)

in which $A_{18}$ is as defined for $A_1$ and $b_3$ is a number from 1 to 25;

component II-f) is a product obtainable by reacting a product, obtained by reaction of a polyamine of the formula

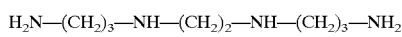
$H_2N\!-\!(CH_2)_3\!-\!NH\!-\!(CH_2)_2\!-\!NH\!-\!(CH_2)_3\!-\!NH_2$ with cyanuric chloride, with a compound of the formula

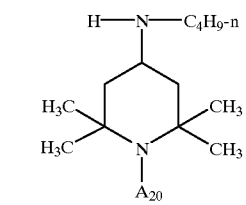

in which $A_{20}$ is as defined for $A_1$;

component II-g) is at least one compound of the formula IX-2-g-1, IX-2-g-2 or IX-2-g-3

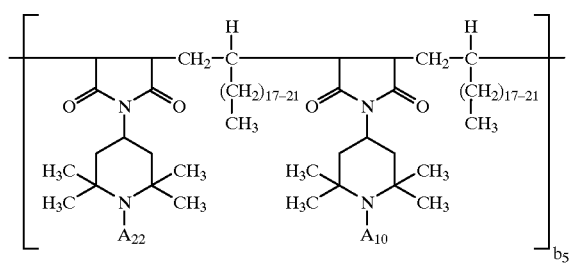
(IX-2-g-1)

-continued

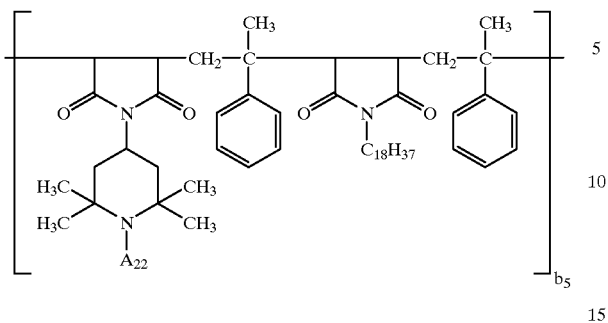

(IX-2-g-2)

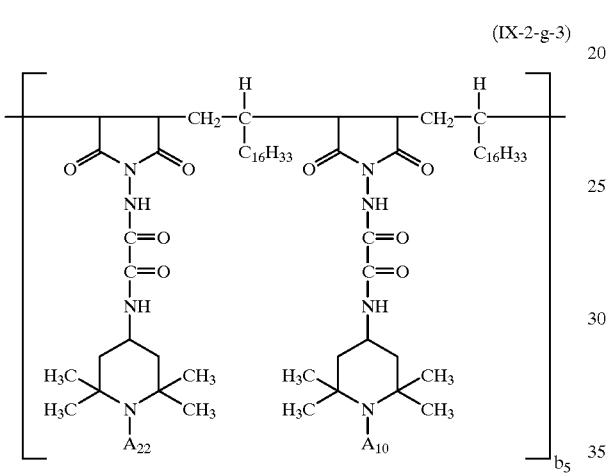

(IX-2-g-3)

in which $A_{10}$ and $A_{22}$ are as defined for $A_1$ and $b_5$ is a number from 1 to 25;

component II-i) is at least one compound of the formula XI-2 in which $A_{31}$ is as defined for $A_1$ and $b_6$ is a number from 2 to 25;

component II-k) is at least one compound of the formula XIII-2-k

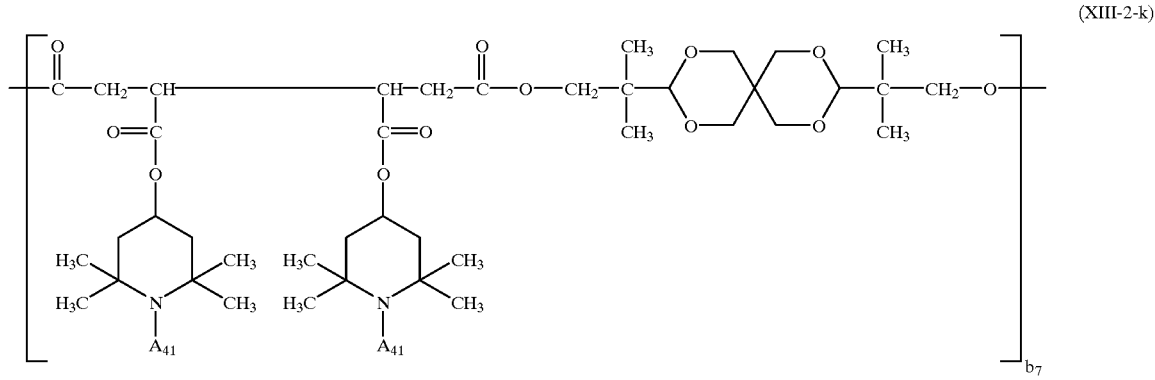

in which $A_{41}$ is as defined for $A_1$ and $b_7$ is a number from 1 to 25;

component II-m) is at least one compound of the formula XVI-2-m

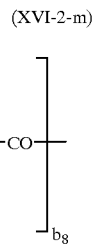

(XVI-2-m)

in which $b_8$ is a number from 2 to 25.

Particular interest attaches to the following stabilizer systems:

a) stabilizer mixture comprising at least one compound of the formula I-1-a-1 in which $R_1$ is cyclohexyl, and at least one compound of the formula XVI-2-m, b) stabilizer mixture comprising at least one compound of the formula I-1-a-1 in which $R_1$ is cyclohexyl, and at least one compound of the formula VI-2-d-1 in which $A_{10}$ is hydrogen, c) stabilizer mixture comprising at least one compound of the formula I-1-a-1 in which $R_1$ is cyclohexyl, and at least one compound of the formula II-2-b in which $A_9$ is methyl, d) stabilizer mixture comprising at least one compound of the formula II-1-b in which $R_9$ is cyclohexyl, and at least one compound of the formula XVI-2-m, e) stabilizer mixture comprising at least one compound of the formula II-1-b in which $R_9$ is cyclohexyl, and at least one compound of the formula VI-2-d-1 in which $A_{10}$ is hydrogen, f) stabilizer mixture comprising at least one compound of the formula II-1-b in which $R_9$ is cyclohexyl, and at least one compound of the formula II-2-b in which $A_9$ is methyl, g) stabilizer mixture comprising at least one compound of the formula V-1-c in which $R_9$ is cyclohexyl, and at least one compound of the formula XVI-2-m, h) stabilizer mixture comprising at least one compound of the formula V-1-c in which $R_9$ is cyclohexyl, and at least one compound of the formula VI-2-d-1 in which $A_{10}$ is hydrogen, i) stabilizer mixture comprising at least one compound of the formula V-1-c in which $R_9$ is cyclohexyl, and at least one compound of the formula II-2-b in which $A_9$ is methyl, j) stabilizer mixture comprising at least one compound of the formula V-1-c in which $R_9$ is methyl, and at least one compound of the formula XVI-2-m, k) stabilizer mixture comprising at least one compound of the formula V-1-c in which $R_9$ is methyl, and at least one compound of the formula VI-2-d-1 in which $A_{10}$ is hydrogen, l) stabilizer mixture comprising at least one compound of the formula V-1-c in which $R_9$ is methyl, and at least one compound of the formula II-2-b in which $A_9$ is methyl, m) stabilizer mixture comprising at least one compound of the formula I-1-a-1 in which $R_1$ is octyl, and at least one compound of the formula VI-2-d-2 in which $A_{10}$ is hydrogen, n) stabilizer mixture comprising at least one compound of the formula I-1-a-1 in which $R_1$ is octyl, and a product obtainable by reacting a product, obtained by reaction of a polyamine of the formula

with cyanuric chloride, with a compound of the formula

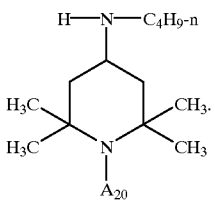

In the abovementioned stabilizer systems, the two components are particularly preferably in a weight ratio of from 1:4 to 1:1.

The novel stabilizer mixture is suitable for stabilizing organic materials against thermal, oxidative or light-induced degradation. Examples of such materials are the following:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(x-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or a-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from a,o-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.

The invention therefore additionally relates to a composition comprising an organic material which is sensitive to oxidative, thermal or light-induced degradation and a novel stabilizer mixture.

The organic material is preferably a synthetic polymer, in particular from one of the above groups. Polyolefins are preferred and polyethylene, polypropylene and copolymers thereof are particularly preferred.

The components of the novel stabilizer system can be added to the material to be stabilized either individually or mixed with one another. In this context, component I-a), I-b), I-c), I-d), I-e), I-f), I-g), I-h), I-i), I-j), I-k) or I-l) can be employed in a quantity of from 0.01 to 2.5%, preferably from 0.05 to 0.5%, and component II-a), II-b), II-c), II-d), II-e), II-f), II-g), II-h), II-i), II-j), II-k), II-l) or II-m) can be employed in a quantity of from 0.01 to 4.99%, preferably from 0.05 to 1.5%, with the proviso that the total quantity of component I-a), I-b), I-c), I-d), I-e), I-f), I-g), I-h), I-i), I-j), I-k) or I-l) and component II-a), II-b), II-c), II-d), II-e), II-f), II-g), II-h), II-i), II-j), II-k), II-l) or II-m) is from 0.02 to 5%, based on the overall weight of the material to be stabilized.

The total quantity of component I-a), I-b), I-c), I-d), I-e), I-f), I-g), I-h), I-i), I-j), I-k) or I-l) and component II-a), II-b), II-c), II-d), II-e), II-f), II-g), II-h), II-i), II-j), II-k), II-l) or II-m) is preferably from 0.05 to 3%, in particular from 0.05 to 2% or from 0.05 to 1%, based on the overall weight of the material to be stabilized.

The weight ratio of component I-a), I-b), I-c), I-d), I-e), I-f), I-g), I-h), I-i), I-j), I-k) or I-l) to component II-a), II-b), II-c), II-d), II-e), II-f), II-g), II-h), II-i), II-j), II-k), II-l) or II-m) is preferably from 20:1 to 1:20, in particular from 10:1 to 1:10, for example from 1:5 to 5:1 or from 1:4 to 1:1.

The novel stabilizer mixture or the individual components can be incorporated into the organic material by known methods, for example before or during shaping or by applying the dissolved or dispersed compounds to the organic material, if desired with subsequent evaporation of the solvent. The individual components of the novel stabilizer mixture can be added to the materials to be stabilized in the form of a powder, as granules or as a masterbatch, which contains these components in, for example, a concentration of from 2.5 to 25% by weight.

If desired, before incorporation, the components of the novel stabilizer system can be mixed with one another in a melt (melt blending).

The novel stabilizer system or its components can be added before or during polymerization or prior to crosslinking.

The materials stabilized in this way can be employed in a wide variety of forms, for example as films, fibres, tapes, moulding compositions or profiles or as binders for coatings, adhesives or putties.

The stabilized organic materials of the invention can additionally comprise various conventional additives, for example:

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butylhydroxyphenyl) adipate.
1.4. Tocopherols, for example α-tocopherol, β-tocopherol, γ-tocopherol, δ-tocopherol and mixtures thereof (Vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dim-ethyl-4-hydroxyphenyl) disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmer-captobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy2-methylphenyl) pentane.
1.7. O—, N— and S-benzyl compounds, for example 3,5,3',5'-tetra-tert-butyl-4,4'-dihydroxy-dibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.
1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis-[4-(1, 1,3,3-tetramethylbutyl)phenyl]-2,2-bis(3,5-di-tert-butyl-4-hydroxybenzyl)malonate.
1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-tri-azine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzyl-phosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxy-phenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylene-diamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-di-aminodiphenylmethane, 4,4'-diaminodiphenylmethane, N,N,N',N'-tetramethyl-4,4'-di-aminodiphenylmethane, 1,2-bis[(2-methylphenyl)amino]ethane, 1,2-bis(phenylamino)propane, (o-tolyl)biguanide, Bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-

2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyl-oxycarbonylethyl)phenyl) benzotriazole, 2-(3'-tert-butyl-5'-[2-(2-ethylhexyloxy)carbonyl-ethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxy-phenyl]-2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxy-benzoate.

2.4. Acrylates, for example ethyl (α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl4-piperidyl)sebacate, bis(2,2,6,6-tetramethyl-4-piperidyl)succinate, bis(1,2,2,6,6-pentamethyl4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dion, bis(1-octyloxy-2,2,6,6-tetramethylpiperidyl)sebacate, bis(1-octyloxy-2,2,6,6-tetramethylpiperidyl)succinate, the condensate of N,N'-bis-(2,2,6,6-tetra-methyl-4-piperidyl) hexamethylenediamine and 4-morpholino-2,6-dichloro-1,3,5-triazine,the condensate of 2-chloro-4,6-bis(4-n-butylamino-2,2,6,6-tetramethylpiperidyl)-1,3,5-tri-azine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cyclo-undecyl-1-oxa-3,8-diaza-4-oxospiro [4,5]decane und epichlorohydrin.

2.7. Oxamides, for example 4,4'-dioctyloxyoxanilide, 2,2'-diethoxyoxanilide, 2,2'-dioc-tyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethox-anilide and its mixture with 2-ethoxy-2'-ethyl-5,4'-di-tert-butoxanilide and mixtures of ortho- and para-methoxy-disubstituted oxanilides and mixtures of o- and p-ethoxy-disub-stituted oxanilides.

2.8. 2-(2-Hydroxyphenyl)-1,3,5-triazines, for example 2,4,6-tris(2-hydroxy-4-octyloxy-phenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyl-oxy-2-hydroxypropoxy)-2-hydroxy-phenyl]4,6-bis(2,4-dimethylphenyl)-1,3,5-triazine, 2-[2-hydroxy-4-(2-hydroxy-3-dodecyloxy-propoxy)phenyl]4,6-bis(2,4-dimethylphenyl)-1,3,5-triazine, 2-(2-hydroxy-4-hexyloxy)phenyl4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tride-cyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-hepta-decyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A4 316 622, DE-A-4 316 876, EP-A-0 589 839 or EP-A-0 591 102 or 3-[4-(2-acet-oxyethoxy)phenyl]-5,7-di-tert-butyl-benzofuran-2-one, 5,7-di-tert-butyl-3-[4-(2-stearoyl-oxyethoxy)phenyl]benzofuran-2-one, 3,3'-bis[5,7-di-tert-butyl-3-(4-[2-hydroxyethoxy]-phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The weight ratio of novel stabilizer mixture to the conventional additives can for example be from 1:0.5 to 1:5.

The invention furthermore relates to the use of the novel stabilizer mixture for stabilizing organic material against oxidative, thermal or light-induced degradation.

The organic materials stabilized by means of the novel stabilizer system are distinguished not only by significantly improved light stability but also, in some cases, by improved thermal stability.

The compounds of the formulae IX-1-g-1, XI-1, XII-1, XIII-1 and XIV-1 and the product defined as component I-f) are novel and are likewise a subject of the present invention.

The present invention also relates to:

1) Compounds of the formula D

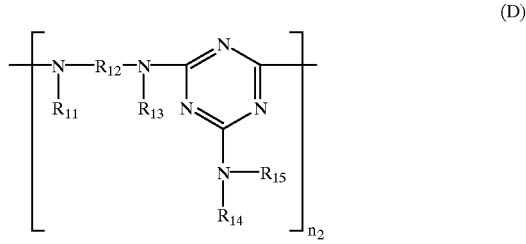

(D)

in which $R_{11}$ and $R_{13}$ independently of one another are hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenytalkyl which is substituted on the phenyl radical by —OH and/or $C_1$–$C_{10}$alkyl, or are a group of the formula IV-1

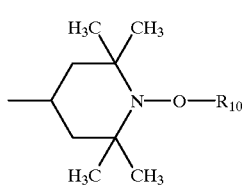
(IV-1)

in which $R_{10}$ is hydrogen, $C_1-C_{18}$alkyl, $C_5-C_{12}$cycloalkyl or $C_1-C_4$alkyl-substituted $C_5-C_{12}$cycloalkyl, $R_{12}$ is $C_2-C_{18}$alkylene, $C_5-C_7$cycloalkylene or $C_1-C_4$alkylenedi($C_5-C_7$cycloalkylene), or the radicals $R_{11}$, $R_{12}$ and $R_{13}$, together with the nitrogen atoms to which they are attached, form a 5- to 10-membered heterocyclic ring, the radicals $R_{14}$ and $R_{15}$, together with the nitrogen atom to which they are attached, form a 5- to 10-membered heterocyclic ring or a group —NH($C_5-C_{12}$cycloalkyl), $n_2$ is a number from 2 to 50 and at least one of the radicals $R_{11}$ and $R_{13}$ is a group of the formula IV-1.

$R_{11}$ and $R_{13}$ are preferably a group of the formula IV-1.

$R_{12}$ is preferably $C_2-C_{10}$alkylene, especially hexamethylene.

The radicals $R_{14}$ and $R_{15}$, together with the nitrogen atom to which they are attached, preferably form morpholino or a group —NH(cyclohexyl).

2) Compounds of the formula G-1

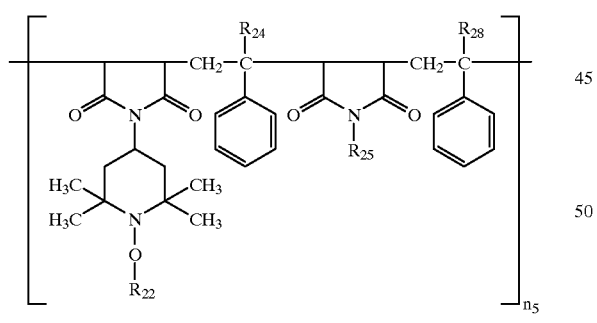
(G-1)

in which
$R_{22}$ is hydrogen, $C_1-C_{18}$alkyl, $C_5-C_{12}$cycloalkyl or $C_1-C_4$alkyl-substituted $C_5-C_{12}$cycloalkyl, $R_{24}$ and $R_{28}$ independently of one another are hydrogen, $C_1-C_{30}$alkyl, $C_5-C_{12}$cycloalkyl or phenyl, $R_{25}$ is hydrogen, $C_1-C_{30}$alkyl, $C_5-C_{12}$cycloalkyl, phenyl, $C_7-C_9$phenylalkyl or a group of the formula IV-1

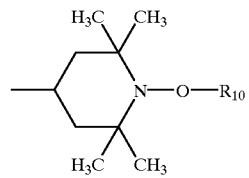
(IV-1)

in which $R_{10}$ is as defined for $R_{22}$ and
$n_5$ is a number from 1 to 50.

$R_{24}$ and $R_{28}$ are preferably $C_1-C_4$alkyl, especially methyl.

$R_{25}$ is preferably $C_1-C_{25}$alkyl.

3) Compounds of the formula G-2

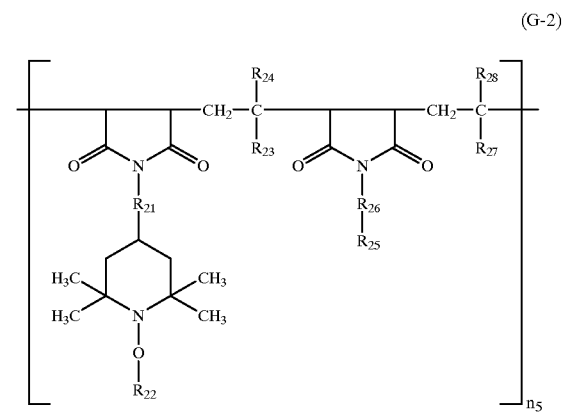
(G-2)

in which
$R_{21}$ and $R_{26}$ are a group —N($Y_1$)—CO—$Y_2$—CO—N($Y_3$)—, $Y_1$ and $Y_3$ independently of one another are hydrogen, $C_1-C_8$alkyl, $C_5-C_{12}$cycloalkyl, phenyl, $C_7-C_9$phenylalkyl or a group of the formula IV-1

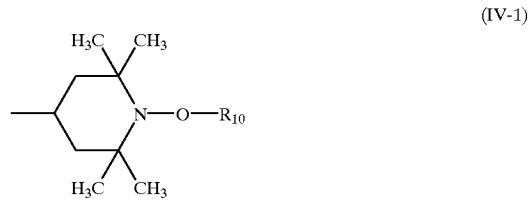
(IV-1)

in which $R_{10}$ is hydrogen, $C_1-C_{18}$alkyl, $C_5-C_{12}$cycloalkyl or $C_1-C_4$alkyl-substituted $C_5-C_{12}$cycloalkyl, $Y_2$ is a direct bond or $C_1-C_4$alkylene, $R_{22}$ is as defined for $R_{10}$, $R_{23}$, $R_{24}$, $R_{27}$ and $R_{28}$ independently of one another are hydrogen, $C_1-C_{30}$alkyl, $C_5-C_{12}$cycloalkyl or phenyl, $R_{25}$ is hydrogen, $C_1-C_{30}$alkyl, $C_5-C_{12}$cycloalkyl, phenyl, $C_7-C_9$phenylalkyl or a group of the formula IV-1 and $n_5$ is a number from 1 to 50.

$Y_1$ and $Y_3$ are preferably hydrogen.

$R_{25}$ is preferably a group of the formula IV-1.

The explanations and expressions of preference made with regard to the novel stabilizer mixtures, in respect of the variable radicals and the terminal groups, are to be applied correspondingly to the novel compounds.

The examples which follow illustrate the invention in greater detail. All percentages are by weight, unless stated otherwise.

EXAMPLE A

Preparation of the Compound of the Formula

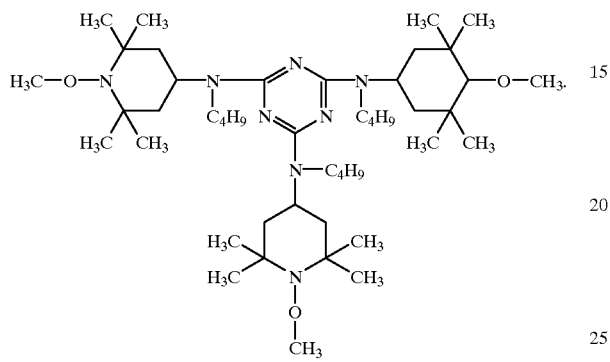

A solution of 23.6 g (0.098 mol) of 4-n-butylamino-1-methoxy-2,2,6,6-tetramethyl-piperidine in 25 ml of xylene is added dropwise to a solution of 4.09 (0.0217 mol) of cyanuric chloride in 50 ml of xylene and 6.2 g (0.098 mol) of pulverulent KOH. The reaction mixture is heated at reflux for 23 hours. The solids are then removed by filtration and the filtrate is concentrated under reduced pressure. The crude product obtained is purified by crystallization (ethanol) to give 14.3 g (82% of theory) of the product indicated above as a white powder. The melting point is 151–153° C.

Elemental analysis for $C_{45}H_{87}N_9O_3$; Calculated: C, 67.4; H, 10.9; N, 15.7; Found: C, 67.4; H, 11.3; N, 15.7.

EXAMPLE B

Preparation of the Compound of the Formula

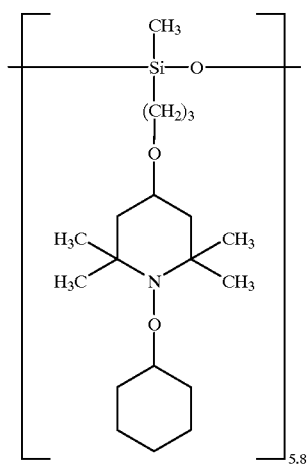

0.5 g of $MoO_3$ is adde to a solution of 24.0 g of the compound of the formula

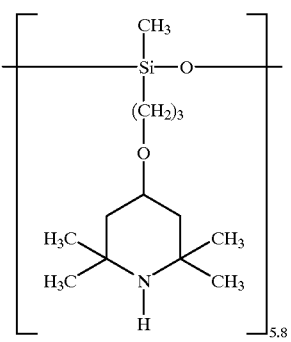

in 200 ml of cyclohexane. The solution is heated at reflux and 20 ml of ter-butyl hydroperoxide (90%) are added over the course of 15 minutes. After the reaction mixture has bee heated at reflux for 12 hours, the catalyst is removed by filtration and a further 0.5 g of $MoO_3$ is added to the filtrate, followed by 20 ml of 90% tert-butyl hydroperoxide. After heating at reflux for a further 12 hours, the red colour has disappeared. The reaction mixture is washed with 5% aqueous $Na_2SO_3$ solution until excess hydroperoxide is no longer present. The reaction solution is washed with water and saline solution, dried over $MgSO_4$ and evaporated. 15 g of the compound indicated above are obtained as a clear viscous resin without crystals. The NMR and MS data agree with the structure indicated.

EXAMPLE C

Preparation of the Compound of the Formula

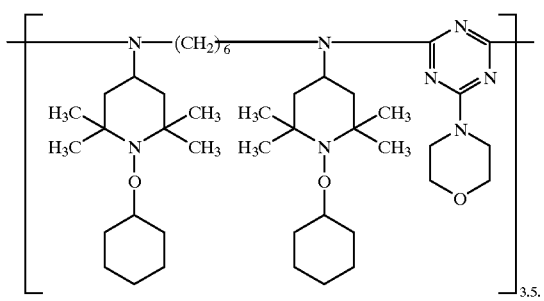

This is prepared in analogy to the process described in Example B, using 31.87 g of the compound of the formula

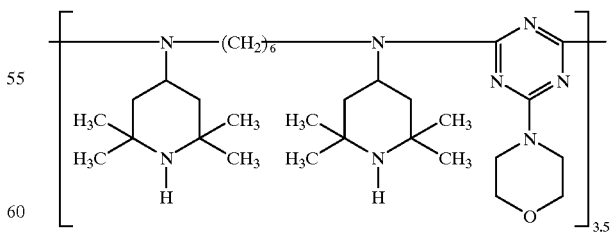

1.0 g of $MoO_3$ and 40 ml of 90% tert-butyl hydroperoxide in 600 ml of cyclohexane. 22.2 g of the compound indicated above are obtained as a white, vitreous solid. The melting point is 135° C. The NMR and MS data agree with the structure indicated.

EXAMPLE D

Preparation of the Compound of the Formula

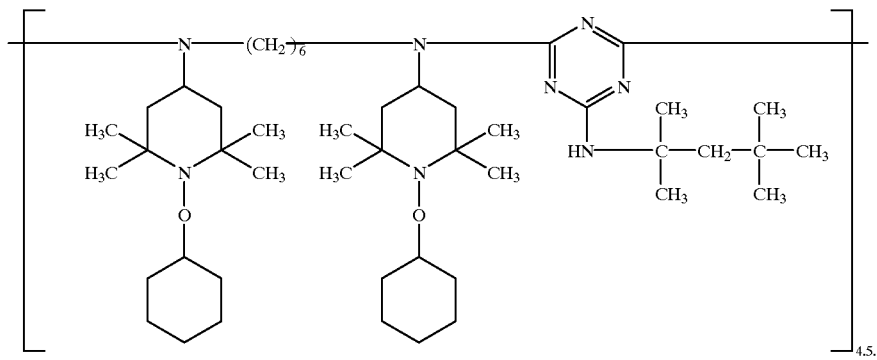

This is prepared in analogy to the process described in Example B, using 25.1 g of the compound of the formula

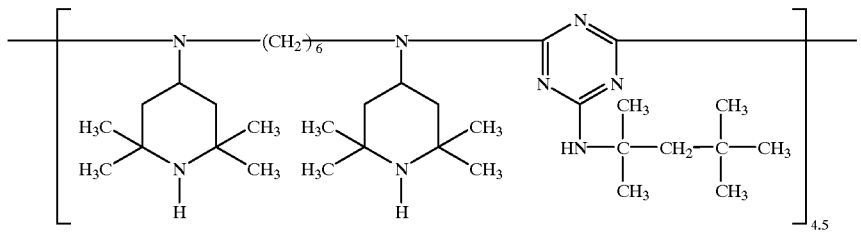

2.0 g of MoO$_3$ and 25 ml of 90% tert-butyl hydroperoxide in 500 ml of cyclohexane. 36.5 g of the compound indicated above are obtained as a pale yellow vitreous solid. The melting point is 105–125° C. The NMR and MS data agree with the structure indicated.

EXAMPLE E

Preparation is carried out in analogy to the process described in Example B, using 25.8 g of ®UVASORB HA 88 [a compound obtainable by reacting a product, obtained by reaction of a polyamine of the formula

H$_2$N—(CH$_2$)$_3$—NH—(CH$_2$)$_2$—NH—(CH$_2$)$_3$—NH$_2$ with cyanuric chloride, with a compound of the formula

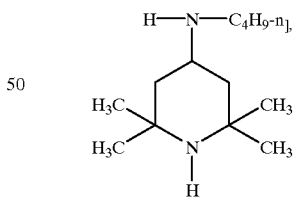

2.0 g of MoO$_3$ and 40 ml of 70% tert-butyl hydroperoxide in 500 ml of cyclohexane. 47.7 g of a corresponding compound are obtained which comprises 1-cyclohexyloxy-2,2,6,6-tetramethylpiperid-4-yl groups instead of 2,2,6,6-tetramethylpiperid-4-yl groups. The compound is a pale yellow resin with some white crystals. The melting point is 135–145° C. Sintering is at 112° C. The NMR and MS data agree with the structure indicated.

EXAMPLE F

Preparation of the Compound of the Formula

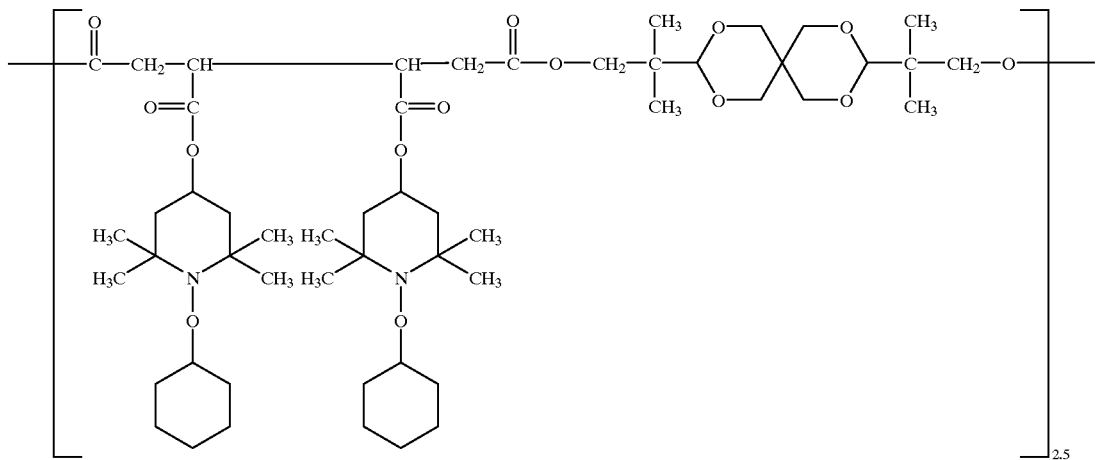

11.0 g (14.5 mmol based on the repetitive unit) of the compound of the formula

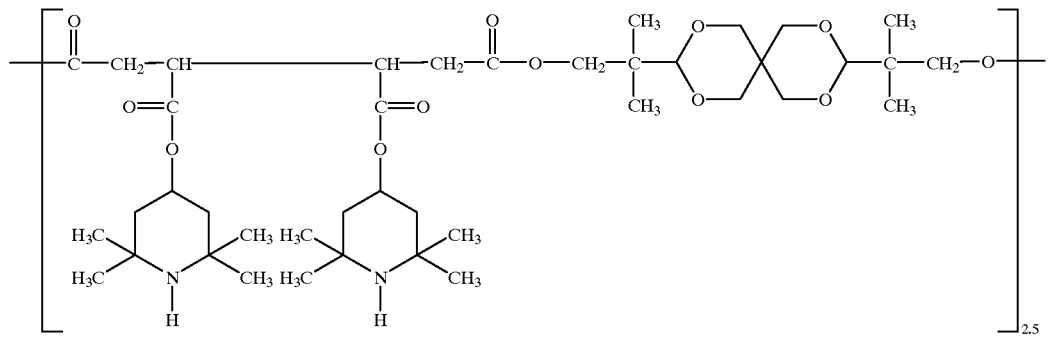

are dissolved in 200 ml of cyclohexane. 0.1 g of $MoO_3$ is added and the mixture is heated at reflux. 10 g (77.5 mmol) of a 70% (% weight/weight) aqueous tert-butyl hydroperoxide solution are added dropwise slowly at 80° C. the water/tert-butanol mixture which forms during the reaction is removed by azeotropic distillation. The mixture is then heated at reflux for 14 hours, cooled to 20–30° C., added to carbon powder and filtered. The solution is washed twice with 10% (% weight/weight) aqueous $Na_2SO_3$ and with water. The organic phase is dried over $Na_2SO_4$, filtered and evaporated at 80° C./24 mbar. The residue obtained is a white powder and has a melting point of 104–108° C. Analysis by NMR ($^1H$, $^{13}C$) agrees with the structure indicated above.

EXAMPLE G

Preparation of the Compound of the Formula

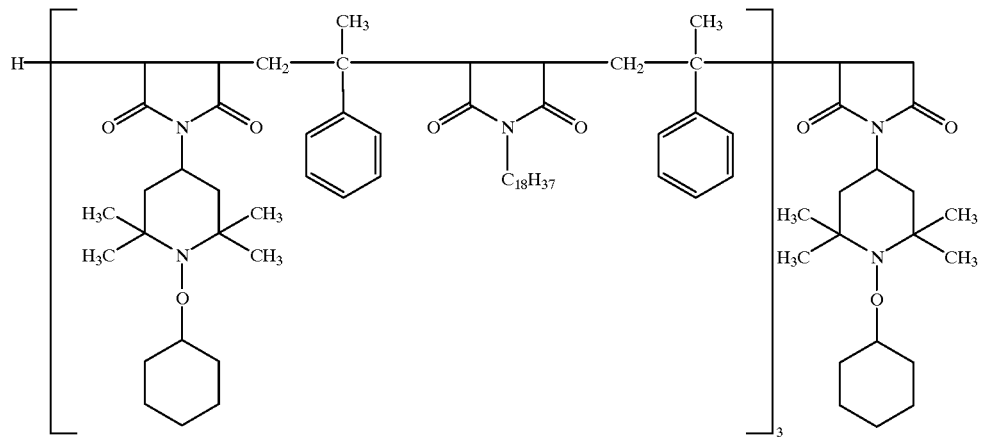

This is prepared in analogy to the process described in Example F. 11 g (10.3 mmol based on the repetitive unit) of the compound of the formula

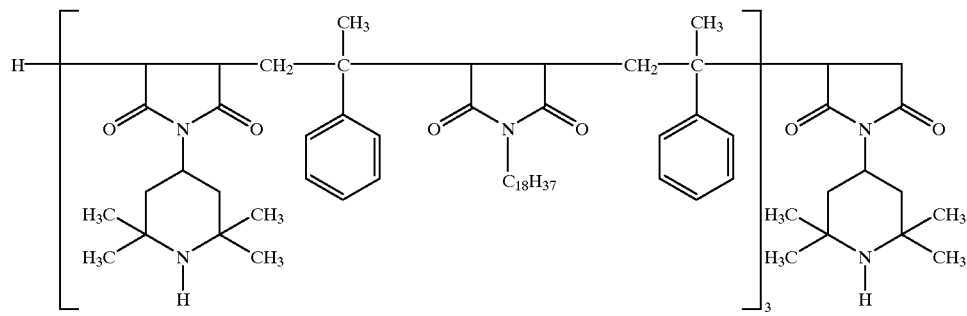

are reacted with 10 g of a 10% (% weight/weight) tert-butyl hydroperoxide solution in cyclohexane in the presence of 0.1 g of $MoO_3$. Following evaporation, a white solid with a melting point of 135–139° C. is obtained. Analysis by NMR ($^1$H, $^{13}$C) agrees with the structure indicated above.

EXAMPLE H

Preparation of the Compound of the Formula

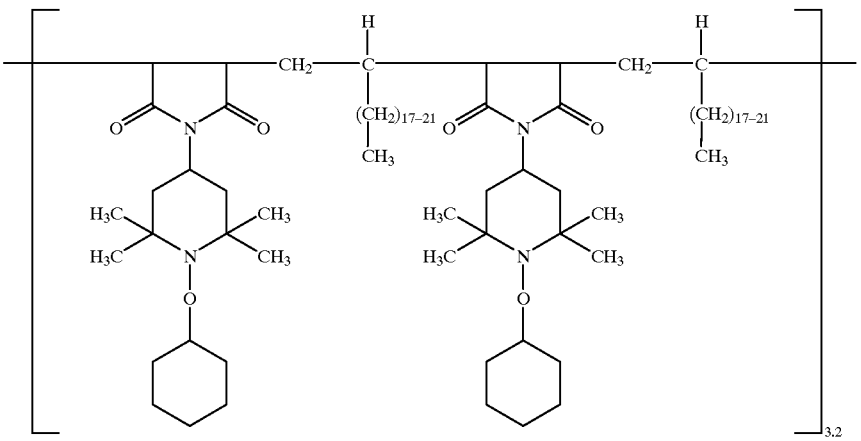

This is prepared in analogy to the process described in Example F. 19 g (30.8 mmol based on the repetitive unit) of the compound of the formula

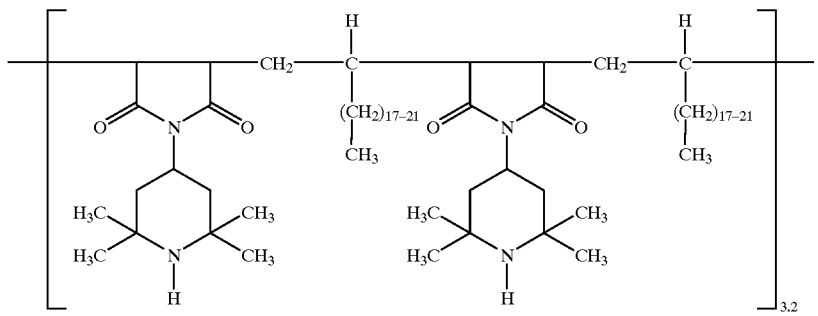

are reacted with 6.6 g of a 70% (% weight/weight) aqueous tert-butyl hydroperoxide solution in cyclohexane in the presence of 0.5 g of $MoO_3$. Following evaporation, a yellow solid with a melting point of 80–87° C. is obtained. Analysis by NMR ($^1$H, $^{13}$C) agrees with the structure indicated above.

EXAMPLE I

Preparation of the Compound of the Formula

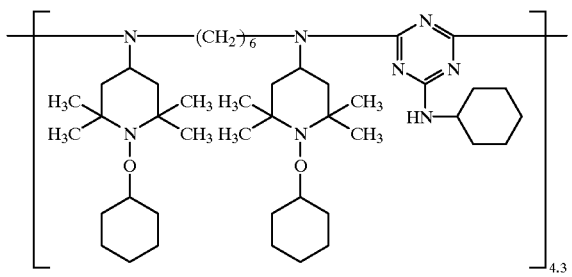

This is prepared in analogy to the process described in Example F. 30 g (39.2 mmol based on the repetitive unit) of the compound of the formula

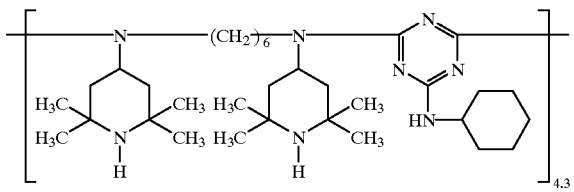

are reacted with 15.2 g of a 70% (% weight/weight) aqueous tert-butyl hydroperoxide solution in cyclohexane in the presence of 0.8 g of $MoO_3$. Following evaporation, a yellow solid with a melting point of 72–77° C. is obtained. Analysis by NMR ($^1$H, $^{13}$C) agrees with the structure indicated above.

THE LIGHT STABILIZERS USED IN EXAMPLES 1 TO 3

(The Mean Degree of Polymerization is Indicated in Each Case.)

Light stabilizer 1-a-1 (U.S. Pat. No 5,204,473, Example 58):

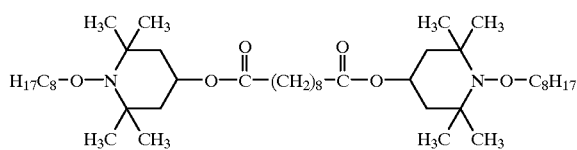

Light stabilizer 1-a-2 (U.S. Pat. No. 5,204,473, Example 4):

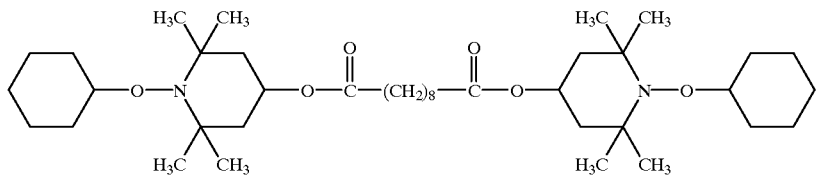

Light stabilizer 1-b-1 (U.S. Pat. No. 5,204,473, Example 62):
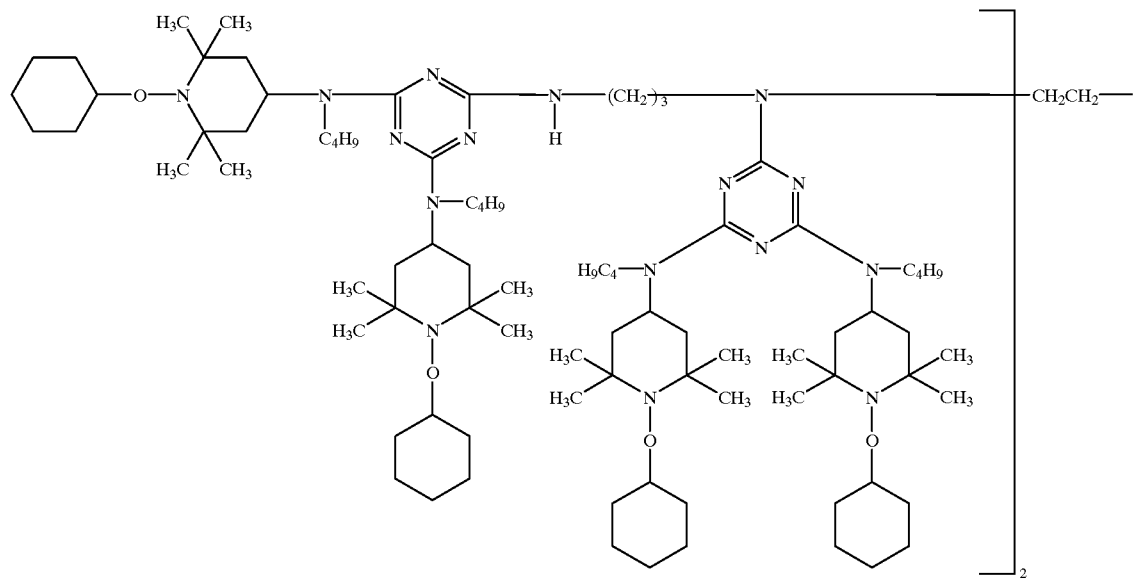
Light stabilizer 1-c-1 (Examlple A):
Light stabilizer 1-c-2 (U.S. Pat. No. 5,204,473, Example 63):
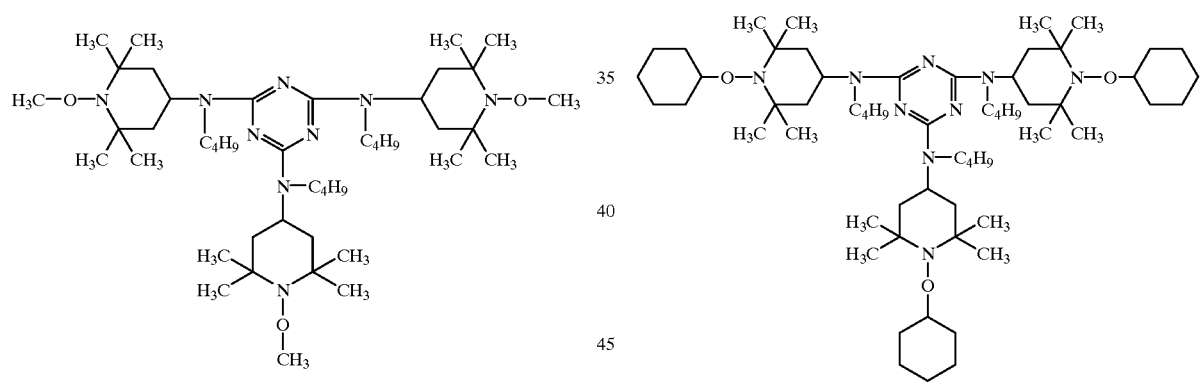
Light stabilizer 1-d-1 (Example D):
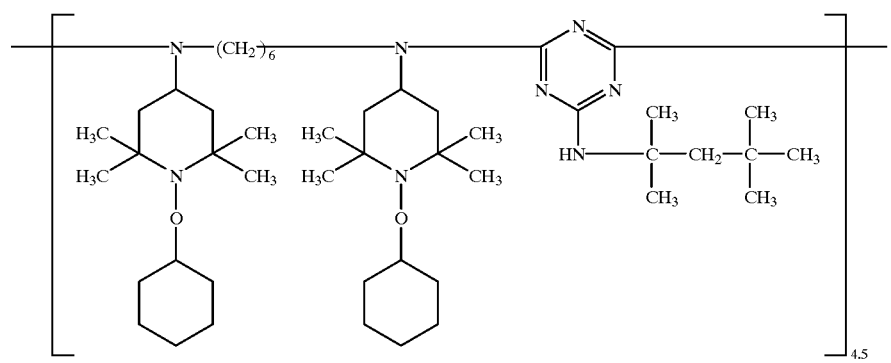

Light stabilizer 1-d-2 (Example C):
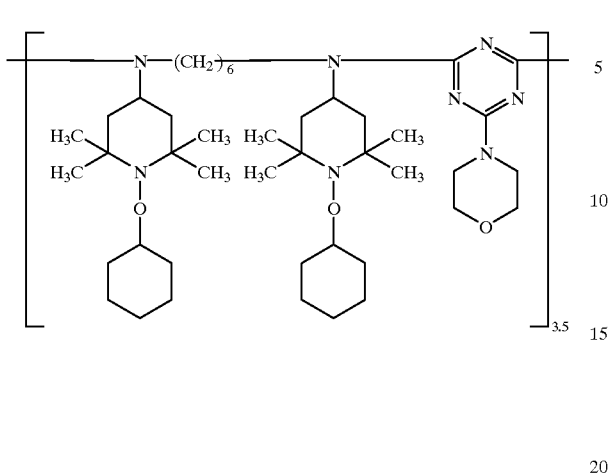
Light stabilizer 1-e-1 (Example B):
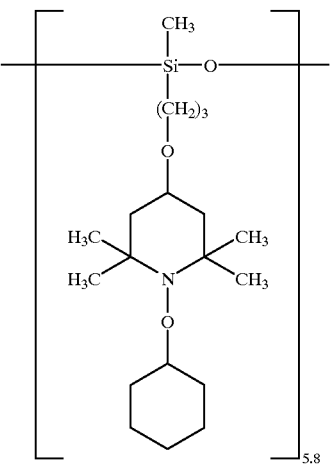
Light stabilizer 1-f-1 (Example E):
®UVASORB HA 88 comprising 1-cyclohexyloxy-2,2,6,6-tetramethylpiperid-4-yl groups instead of 2,2,6,6-tetramethylpiperid-4-yl groups.
Light stabilizer 1-d-3 (Example I):
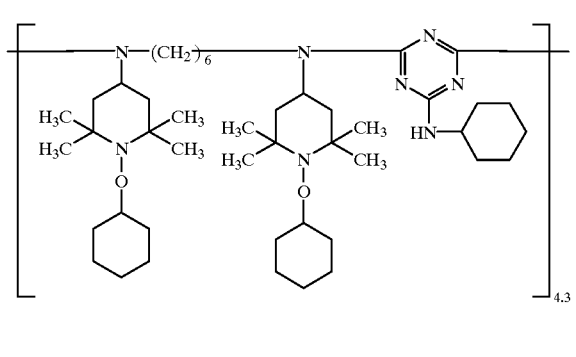
Light stabilizer 1-g-1 (Example H):
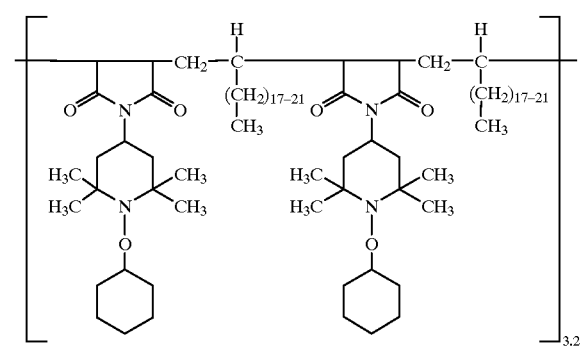
Light stabilizer 1-g-2 (Example G):
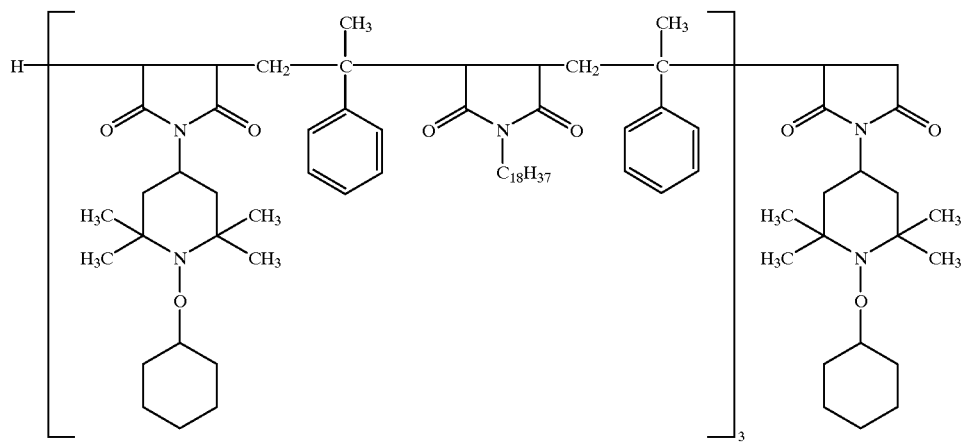

Light stabilizer 1-k-1 (Example F):
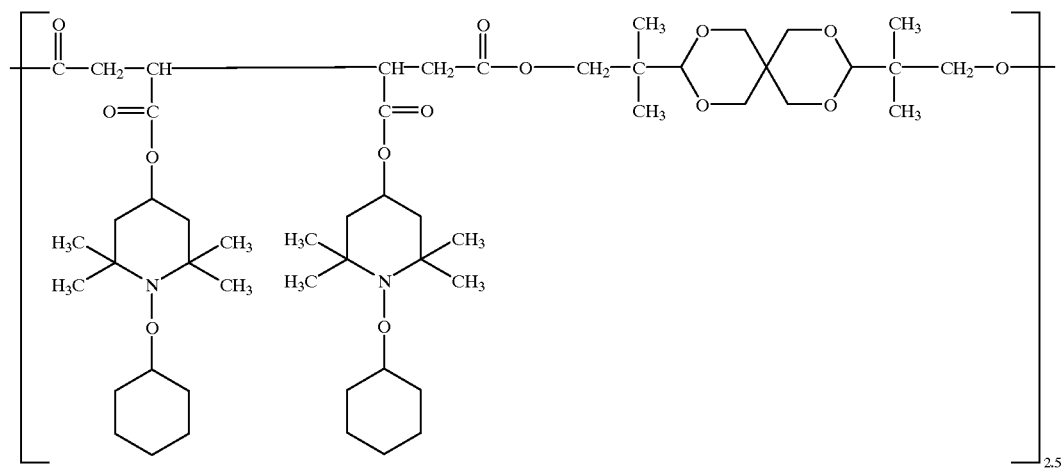
Light stabilizer 2-a-3:
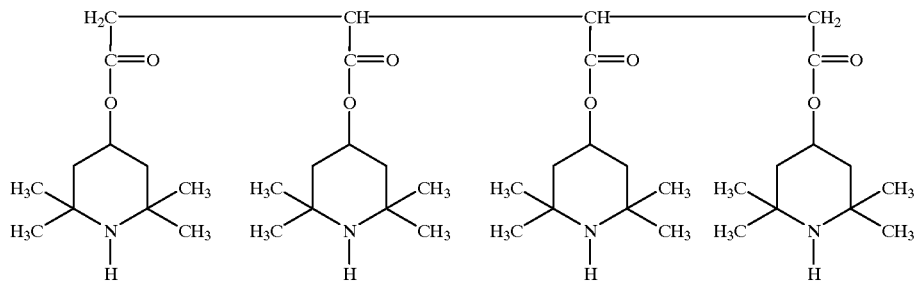
Light stabilizer 2-a-4:
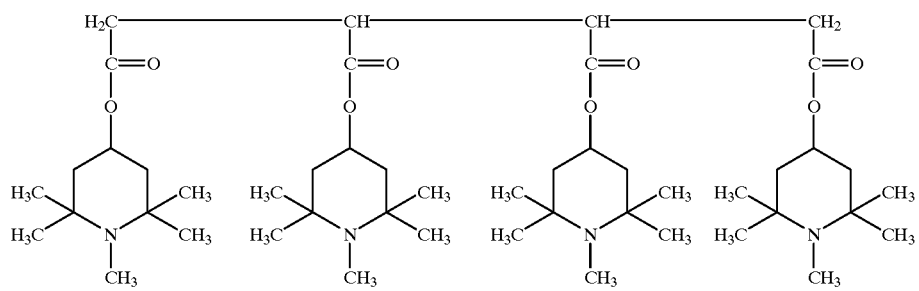

Light stabilizer 2-b-1:
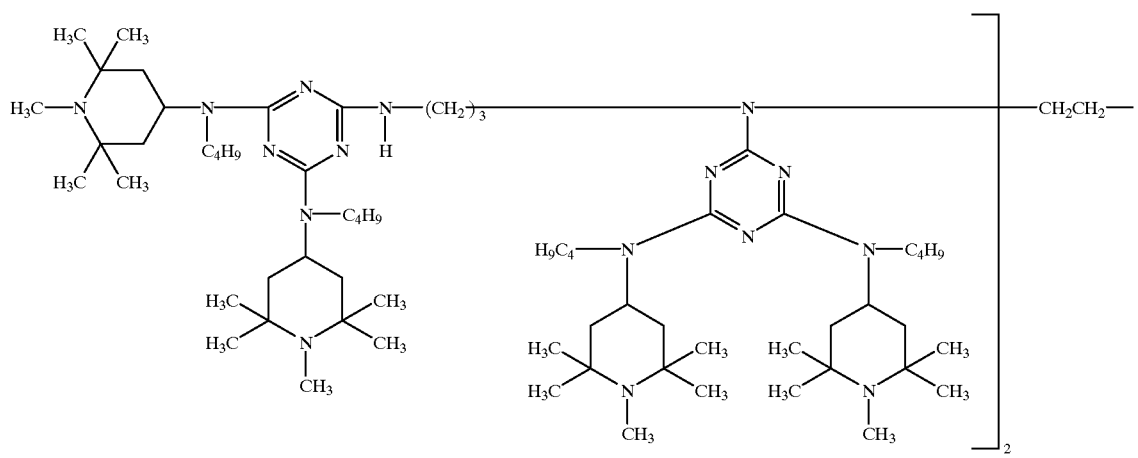
Light stabilizer 2-d-1:
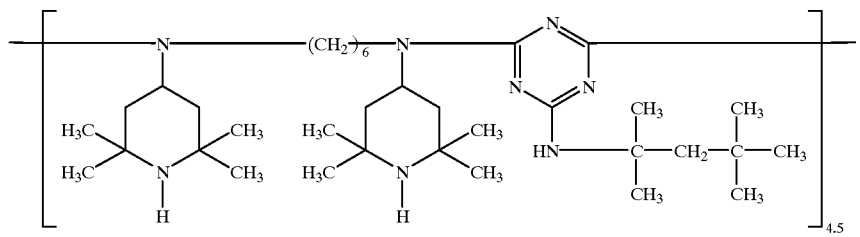
Light stabilizer 2-d-2:
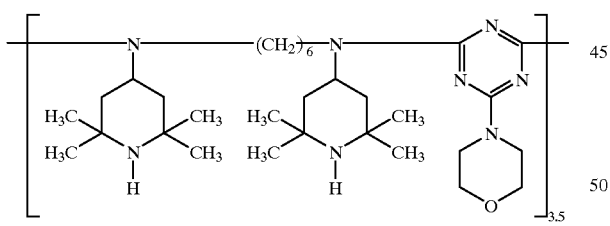
Light stabilizer 2-e-1:
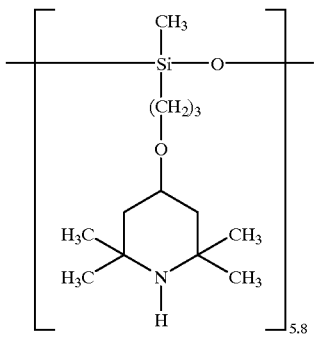
Light stabilizer 2-d-3:
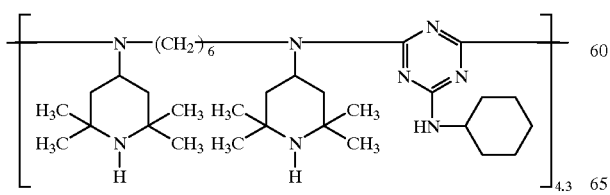
Light stabilizer 2-f-1:
Compound obtainable by reacting a product, obtained by reaction of a polyamine of the formula

with cyanuric chloride, with a compound of the formula
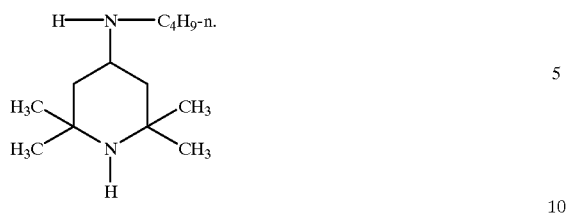
Light stabilizer 2-g-1:
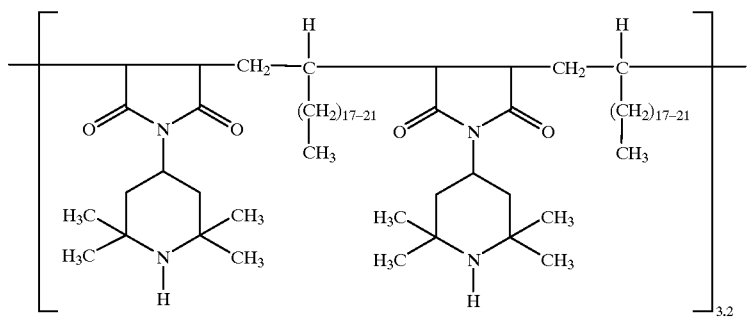
Light stabilizer 2-g-2:
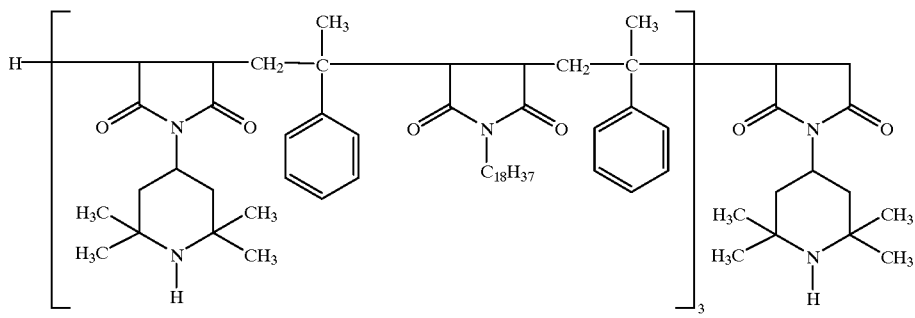
Light stabilizer 2-i-1:
Mixture of the compounds
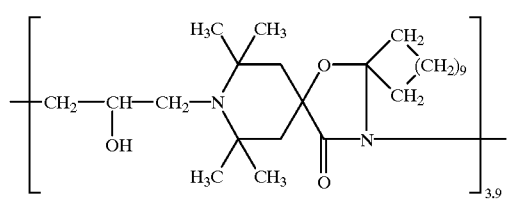
and
-continued
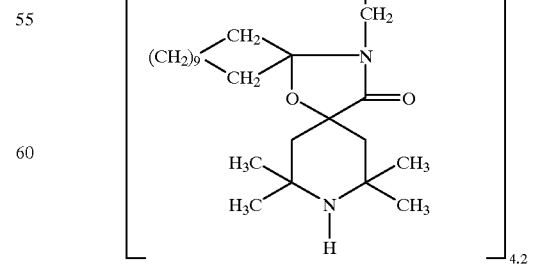
in a ratio of about 4:1.

Light stabilizer 2-k-1:

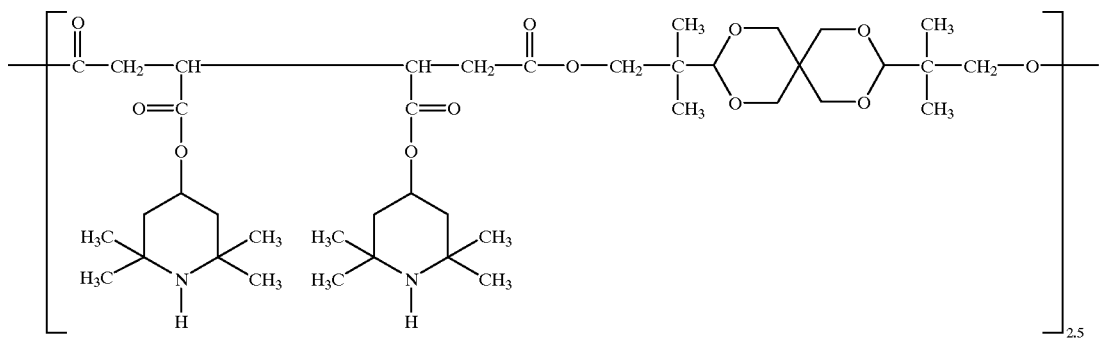

Light stabilizer 2-k-2:

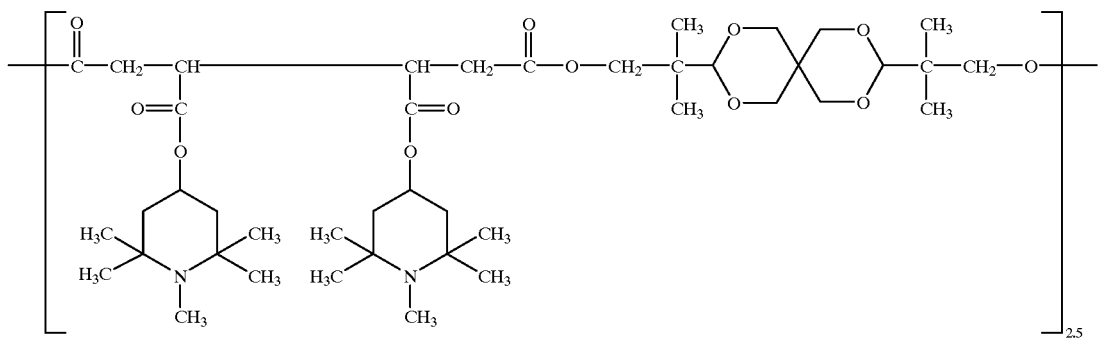

Light stabilizer 2-m-1:

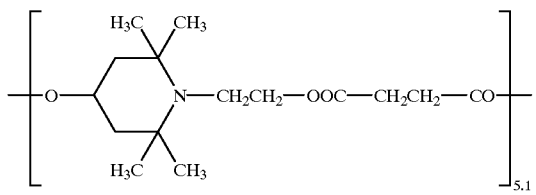

EXAMPLE 1

Light Stabilization in Low-density Polyethylene Films 100 parts of low-density (density=0.918 g/cm³) polyethylene powder are homogenized with 0.03 part of octadecyl β-(3,5-di-tert-butyl-4-hydroxyphenyl)propionate and with the proportion of light stabilizers indicated in Table 1 in a Brabender plastograph at 180° C. for 10 minutes. The composition thus obtained is removed from the compounder as rapidly as possible and compressed in a press to give a sheet with a thickness of 2–3 mm. A piece of the resultant green pressure moulding is cut out and pressed between two high-gloss hard aluminium foils for 6 minutes at 170° C. under 12 tonnes using a laboratory press to give a film with a thickness of 0.2 mm, which is immediately quenched in cold water. Sections each measuring 55×9 mm² are punched out of this film and stored under $SO_2$ gas in a desciccator for 24 hours. The films are then exposed in an SEPAP 12.24. These test specimens are removed from the exposure apparatus at regular intervals and tested for their carbonyl content in an FTIR spectrometer.

A measure for the protective action is the time ($T_{0.2}$ measured) needed to reach a carbonyl extinction of 0.2. The results are summarized in Table 1.

The synergistic effect is determined by a comparison of the calculated $T_{0.2}$ value with the measued $T_{0.2}$ value. The $T_{0.2}$ values are calculated on the basis of the additivity law (B. Ranby and J. F. Rabek, Photodegradation, Photooxidation and Photostabilization of Polymers, Principles and Applications, a Wiley-Interscience Publication, 1975, pages 418–422) according to the following equation:

$$T_{0.2\,calculated} = \frac{T_{0.2} - \text{Stabilizer 1} + T_{0.2} - \text{Stabilizer 2}}{2}$$

There is a synergistic effect for the mixture in question, when $T_{0.2\,measured} > T_{0.2\,calculated}$.

TABLE 1

Light stabilization in low-density polyethylene films.

| Light stabilizer | $T_{0.2}$ measured in hours | $T_{0.2}$ calculated in hours |
|---|---|---|
| none (control) | 55 | |
| 0.15% (1-b-1) | 1730 | |
| 0.15% (2-d-1) | 615 | |
| 0.075% (1-b-1) and 0.075% (2-d-1) | 1600 | 1173 |

EXAMPLE 2

Light Stabilization in Polypropylene Block Copolymer Films.

100 parts of polypropylene block copolymer powder are homogenized with 0.05 part of pentaerythrityl tetrakis[3-(3,5-di-tert-butyl-4-hydroxyphenyl)propionate], 0.10 part of tris(2,4-di-tert-butylphenyl) phosphite, 0.1 part of Ca stearate and with the light stabilizers indicated in Table 2 in a Brabender plastograph at 200° C. for 10 minutes. The composition thus obtained is removed from the compounder as rapidly as possible and compressed in a toggle press to give a sheet with a thickness of 2–3 mm. A piece of the resultant green press-moulding is cut out and pressed between two high-gloss hard aluminium foils for 6 minutes at 260° C. using a laboratory hydraulic press to give a film with a thickness of 0.5 mm, which is immediately cooled in a water-cooled press. Sections each measuring 60 mm×25 mm are then punched out of this 0.5 mm film and are exposed in a WEATHER-OMETER Ci 65 (black panel temperature 63±2° C., no irrigation). These test specimens are removed from the exposure apparatus at regular intervals and tested for their carbonyl content in an IR spectrometer. The increase in the carbonyl extinction on exposure is a measure of the photooxidative degradation of the polymer and is known from experience to be associated with a deterioration in the mechanical properties.

The time ($T_{0.2\ measured}$) needed to reach a carbonyl extinction of 0.2 is shown in Table 2.

The synergistic effect is determined by a comparison of the calculated $T_{0.2}$ value with the measured $T_{0.2}$ value as shown in Example 1.

TABLE 2

Light stabilization action in polypropylene block copolymer films.

| Light stabilizer | $T_{0.2\ measured}$ in hours | $T_{0.2\ calculated}$ in hours |
|---|---|---|
| None | 120 | |
| 0.1% of compound 2-m-1 | 1250 | |
| 0.1% of compound 2-d-1 | 870 | |
| 0.1% of compound 2-b-1 | 1480 | |
| 0.1% of compound 2-d-2 | 1290 | |
| 0.1% of compound 2-f-1 | 1150 | |
| 0.1% of compound 2-i-1 | 1040 | |
| 0.1% of compound 2-g-1 | 515 | |
| 0.1% of compound 2-g-2 | 340 | |
| 0.1% of compound 2-k-2 | 865 | |
| 0.1% of compound 2-k-1 | 675 | |
| 0.1% of compound 2-e-1 | 1730 | |
| 0.1% of compound 2-a-4 | 1370 | |
| 0.1% of compound 2-a-3 | 1320 | |
| 0.1% of compound 1-k-1 | 755 | |
| 0.1% of compound 1-g-2 | 300 | |
| 0.1% of compound 1-a-1 | 955 | |
| 0.1% of compound 1-b-1 | 680 | |
| 0.1% of compound 1-c-2 | 1210 | |
| 0.1% of compound 1-e-1 | 1300 | |
| 0.1% of compound 1-d-2 | 265 | |
| 0.1% of compound 1-d-1 | 440 | |
| 0.1% of compound 1-f-1 | 600 | |
| 0.05% of compound 1-e-1 and 0.05% of compound 2-m-1 | 1520 | 1275 |
| 0.05% of compound 1-e-1 and 0.05% of compound 2-d-1 | 1740 | 1085 |
| 0.05% of compound 1-e-1 and 0.05% of compound 2-b-1 | 1750 | 1390 |
| 0.05% of compound 1-e-1 and 0.05% of compound 2-d-2 | 1550 | 1295 |
| 0.05% of compound 1-e-1 and 0.05% of compound 2-f-1 | 1710 | 1225 |
| 0.05% of compound 1-e-1 and 0.05% of compound 2-i-1 | 1500 | 1170 |
| 0.05% of compound 1-e-1 and 0.05% of compound 2-g-1 | 1220 | 907 |
| 0.05% of compound 1-e-1 and 0.05% of compound 2-g-2 | 900 | 820 |
| 0.05% of compound 1-e-1 and 0.05% of compound 2-k-2 | 1330 | 1082 |
| 0.05% of compound 1-e-1 and 0.05% of compound 2-k-1 | 1330 | 987 |
| 0.05% of compound 1-e-1 and 0.05% of compound 2-e-1 | 1720 | 1515 |
| 0.05% of compound 1-e-1 and 0.05% of compound 2-a-4 | 1760 | 1335 |
| 0.05% of compound 1-e-1 and 0.05% of compound 2-a-3 | 1810 | 1310 |
| 0.05% of compound 1-d-1 and 0.05% of compound 2-m-1 | 1015 | 845 |
| 0.05% of compound 1-d-1 and 0.05% of compound 2-d-1 | 810 | 655 |
| 0.05% of compound 1-d-1 and 0.05% of compound 2-b-1 | 1095 | 960 |
| 0.05% of compound 1-d-1 and 0.05% of compound 2-d-2 | 960 | 865 |
| 0.05% of compound 1-d-1 and 0.05% of compound 2-f-1 | 875 | 795 |
| 0.05% of compound 1-d-1 and 0.05% of compound 2-i-1 | 915 | 740 |
| 0.05% of compound 1-d-1 and 0.05% of compound 2-g-1 | 625 | 477 |
| 0.05% of compound 1-d-1 and 0.05% of compound 2-g-2 | 467 | 390 |
| 0.05% of compound 1-d-1 and 0.05% of compound 2-k-2 | 730 | 652 |
| 0.05% of compound 1-d-1 and 0.05% of compound 2-k-1 | 635 | 557 |
| 0.05% of compound 1-d-1 and 0.05% of compound 2-e-1 | 1430 | 1085 |
| 0.05% of compound 1-d-1 and 0.05% of compound 2-a-4 | 1020 | 905 |
| 0.05% of compound 1-d-1 and 0.05% of compound 2-a-3 | 980 | 880 |
| 0.05% of compound 1-c-2 and 0.05% of compound 2-m-1 | 1430 | 1230 |
| 0.05% of compound 1-c-2 and 0.05% of compound 2-d-1 | 1320 | 1040 |
| 0.05% of compound 1-c-2 and 0.05% of compound 2-b-1 | 1550 | 1345 |
| 0.05% of compound 1-c-2 and 0.05% of compound 2-d-2 | 1410 | 1250 |
| 0.05% of compound 1-c-2 and 0.05% of compound 2-f-1 | 1460 | 1180 |
| 0.05% of compound 1-c-2 and 0.05% of compound 2-i-1 | 1300 | 1125 |
| 0.05% of compound 1-c-2 and 0.05% of compound 2-g-1 | 1095 | 862 |
| 0.05% of compound 1-c-2 and 0.05% of compound 2-g-2 | 820 | 775 |
| 0.05% of compound 1-c-2 and 0.05% of compound 2-k-2 | 1125 | 1037 |
| 0.05% of compound 1-c-2 and 0.05% of compound 2-k-1 | 1155 | 942 |
| 0.05% of compound 1-c-2 and 0.05% of compound 2-e-1 | 1900 | 1470 |
| 0.05% of compound 1-c-2 and 0.05% of compound 2-a-4 | 1400 | 1290 |
| 0.05% of compound 1-c-2 and 0.05% of compound 2-a-3 | 1430 | 1265 |
| 0.05% of compound 1-f-1 and 0.05% of compound 2-m-1 | 1220 | 925 |
| 0.05% of compound 1-f-1 and 0.05% of compound 2-d-1 | 985 | 735 |
| 0.05% of compound 1-f-1 and 0.05% of compound 2-b-1 | 1220 | 1040 |
| 0.05% of compound 1-f-1 and | 1020 | 945 |

TABLE 2-continued

Light stabilization action in polypropylene block copolymer films.

| Light stabilizer | $T_{0.2\ measured}$ in hours | $T_{0.2\ calculated}$ in hours |
|---|---|---|
| 0.05% of compound 2-d-2 | | |
| 0.05% of compound 1-f-1 and 0.05% of compound 2-f-1 | 1095 | 875 |
| 0.05% of compound 1-f-1 and 0.05% of compound 2-i-1 | 910 | 820 |
| 0.05% of compound 1-f-1 and 0.05% of compound 2-k-1 | 785 | 637 |
| 0.05% of compound 1-f-1 and 0.05% of compound 2-e-1 | 1630 | 1165 |
| 0.05% of compound 1-f-1 and 0.05% of compound 2-a-4 | 1085 | 985 |
| 0.05% of compound 1-f-1 and 0.05% of compound 2-a-3 | 1230 | 960 |
| 0.05% of compound 1-b-1 and 0.05% of compound 2-m-1 | 1400 | 965 |
| 0.05% of compound 1-b-1 and 0.05% of compound 2-d-1 | 905 | 775 |
| 0.05% of compound 1-b-1 and 0.05% of compound 2-d-2 | 1005 | 985 |
| 0.05% of compound 1-b-1 and 0.05% of compound 2-k-2 | 965 | 772 |
| 0.05% of compound 1-b-1 and 0.05% of compound 2-k-1 | 850 | 677 |
| 0.05% of compound 1-b-1 and 0.05% of compound 2-e-1 | 1760 | 1205 |
| 0.05% of compound 1-b-1 and 0.05% of compound 2-a-4 | 1370 | 1025 |
| 0.05% of compound 1-b-1 and 0.05% of compound 2-a-3 | 1440 | 1000 |
| 0.05% of compound 1-a-1 and 0.05% of compound 2-d-2 | 1300 | 1122 |
| 0.05% of compound 1-a-1 and 0.05% of compound 2-f-1 | 1160 | 1052 |
| 0.05% of compound 1-a-1 and 0.05% of compound 2-i-1 | 1180 | 997 |
| 0.05% of compound 1-a-1 and 0.05% of compound 2-g-1 | 860 | 735 |
| 0.05% of compound 1-a-1 and 0.05% of compound 2-k-1 | 870 | 815 |
| 0.05% of compound 1-a-1 and 0.05% of compound 2-e-1 | 1640 | 1342 |
| 0.05% of compound 1-a-1 and 0.05% of compound 2-a-4 | 1250 | 1162 |
| 0.05% of compound 1-d-2 and 0.05% of compound 2-k-2 | 600 | 565 |
| 0.05% of compound 1-d-2 and 0.05% of compound 2-k-1 | 517 | 470 |
| 0.05% of compound 1-d-2 and 0.05% of compound 2-e-1 | 1190 | 997 |
| 0.05% of compound 1-d-2 and 0.05% of compound 2-a-3 | 875 | 792 |
| 0.05% of compound 1-k-1 and 0.05% of compound 2-m-1 | 1125 | 1002 |
| 0.05% of compound 1-k-1 and 0.05% of compound 2-e-1 | 1590 | 1242 |
| 0.05% of compound 1-g-2 and 0.05% of compound 2-g-1 | 422 | 407 |

EXAMPLE 3

Light Stabilization in Low-density Polyethylene Films 100 parts of low-density (density=0.918 g/cm³) polyethylene powder are homogenized with 0.03 part of octadecyl 3-(3,5-di-tert-butyl-4-hydroxyphenyl)propionate and with the light stabilizers indicated in Table 3 in a Brabender plastograph at 180° C. for 10 minutes. The composition thus obtained is removed from the compounder as rapidly as possible and compressed in a press to give a sheet with a thickness of 2–3 mm. A piece of the resultant green press-moulding is cut out and pressed between two high-gloss hard aluminium foils for 6 minutes at 170° C. under using a laboratory hydraulic press to give a film with a thickness of 0.2 mm, which is immediately cooled in a water-cooled press. Sections each measuring 60 mm×25 mm are then punched out of this 0.2 mm film and exposed to fuming hydrochloric acid for 24 hours. This is regarded as a simulation of the effect of halogen containing compounds such as certain pesticides or flame retardants.

The samples are then exposed in a WEATHER-OMETER Ci 65 (black panel temperature 63±2° C., no irrigation). The test specimens are removed from the exposure apparatus at regular intervals and tested for their carbonyl content in an IR spectrometer. The increase in the carbonyl extinction on exposure is a measure of the photooxidative degradation of the polymer and is known from experience to be associated with a deterioration in the mechanical properties.

The time ($T_{0.2\ measured}$) needed to reach a carbonyl extinction of 0.2 is shown in Table 3.

The synergistic effect is determined by a comparison of the calculated $T_{0.2}$ value with the measured $T_{0.2}$ value as shown in Example 1.

TABLE 3

Light stabilization action in low-density polyethylene films.

| Light stabilizer | $T_{0.2\ measured}$ in hours | $T_{0.2\ calculated}$ in hours |
|---|---|---|
| None | 215 | |
| 0.1% of compound 1-b-1 | 2620 | |
| 0.1% of compound 1-a-1 | 1560 | |
| 0.1% of compound 1-c-2 | 4680 | |
| 0.1% of compound 1-c-1 | 6760 | |
| 0.1% of compound 2-m-1 | about 215 | |
| 0.1% of compound 2-d-1 | 2920 | |
| 0.1% of compound 2-b-1 | 2020 | |
| 0.1% of compound 2-d-2 | 3060 | |
| 0.1% of compound 2-f-1 | 2740 | |
| 0.1% of compound 2-i-1 | 3000 | |
| 0.1% of compound 2-g-1 | 1520 | |
| 0.1% of compound 2-g-2 | 740 | |
| 0.1% of compound 2-k-2 | 1840 | |
| 0.1% of compound 2-k-1 | 2000 | |
| 0.1% of compound 2-a-4 | 2400 | |
| 0.1% of compound 2-a-3 | 2440 | |
| 0.05% of compound 1-b-1 and 0.05% of compound 2-m-1 | 1620 | 1417 |
| 0.05% of compound 1-b-1 and 0.05% of compound 2-d-1 | 3220 | 2770 |
| 0.05% of compound 1-b-1 and 0.05% of compound 2-d-2 | 2920 | 2840 |
| 0.05% of compound 1-b-1 and 0.05% of compound 2-f-1 | 3200 | 2680 |
| 0.05% of compound 1-b-1 and 0.05% of compound 2-i-1 | 2900 | 2810 |
| 0.05% of compound 1-b-1 and 0.05% of compound 2-g-1 | 2400 | 2070 |
| 0.05% of compound 1-b-1 and 0.05% of compound 2-k-2 | 2400 | 2230 |
| 0.05% of compound 1-b-1 and 0.05% of compound 2-k-1 | 2640 | 1810 |
| 0.05% of compound 1-b-1 and 0.05% of compound 2-a-4 | 3300 | 2510 |
| 0.05% of compound 1-b-1 and 0.05% of compound 2-a-3 | 3000 | 2530 |
| 0.05% of compound 1-a-1 and 0.05% of compound 2-d-2 | 4160 | 2310 |
| 0.05% of compound 1-a-1 and 0.05% of compound 2-f-1 | 4560 | 2150 |
| 0.05% of compound 1-a-1 and 0.05% of compound 2-i-1 | 2940 | 2280 |
| 0.05% of compound 1-a-1 and 0.05% of compound 2-g-1 | 1970 | 1540 |
| 0.05% of compound 1-a-1 and 0.05% of compound 2-g-2 | 1360 | 1150 |
| 0.05% of compound 1-a-1 | 2820 | 1700 |

TABLE 3-continued

Light stabilization action in low-density polyethylene films.

| Light stabilizer | $T_{0.2\ measured}$ in hours | $T_{0.2\ calculated}$ in hours |
| --- | --- | --- |
| 0.05% of compound 2-k-2 | | |
| 0.05% of compound 1-a-1 and 0.05% of compound 2-k-1 | 2460 | 1780 |
| 0.05% of compound 1-a-1 and 0.05% of compound 2-a-4 | 3300 | 1980 |
| 0.05% of compound 1-a-1 and 0.05% of compound 2-a-3 | 3760 | 2000 |
| 0.05% of compound 1-c-2 and 0.05% of compound 2-d-1 | 4560 | 3800 |
| 0.05% of compound 1-c-2 and 0.05% of compound 2-b-1 | 4000 | 3350 |
| 0.05% of compound 1-c-1 and 0.05% of compound 2-m-1 | 4680 | 3487 |
| 0.05% of compound 1-c-1 and 0.05% of compound 2-b-1 | 5040 | 4390 |

What is claimed is:

1. A stabilizer Mixture comprising a first component I-a), I-b), I-c), I-d), I-e), I-f), I-g), I-h), I-i), I-j), I-k) or I-l) and a second component II-a), II-b), II-c), II-d), II-e), II-f), II-g), II-h), II-i), II-j), II-k), II-l) or II-m);

with the proviso that stabilizer mixtures comprising a first component I-b), I-c), I-d) or I-l) and a second component II-b), II-c), II-d) or II-l) are disclaimed, where component I-a) is at least one compound of the formula I-1

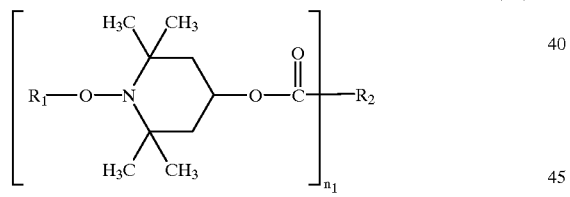

(I-1)

in which

R$_1$ is hydrogen, $C_1$–$C_{18}$alkyl, $C_5$–$C_{12}$cycloalkyl or $C_1$–$C_4$alkyl-substituted $C_5$–$C_{12}$cycloalkyl, $n_1$ is 1, 2 or 4, if $n_1$ is 1, R$_2$ is $C_1$–$C_{25}$alkyl, if $n_1$ is 2, R$_2$ is $C_1$–$C_{14}$alkylene and if $n_1$ is 4, R$_2$ is $C_4$–$C_{10}$alkanetetrayl, with the provisos that, (1) in a stabilizer mixture comprising component I-a) and component II-b) or II-m), if $n_1$=2, R$_1$ is other than $C_1$–$C_{18}$alkyl and (2) in a stabilizer mixture comprising component I-a) and component II-d), if $n_1$=2 and R$_1$=$C_1$–$C_{18}$alkyl, the group —N(A$_{14}$)A$_{15}$ is a 5- to 10-membered heterocyclic ring;

component I-b) is at least one compound of the formula II-1

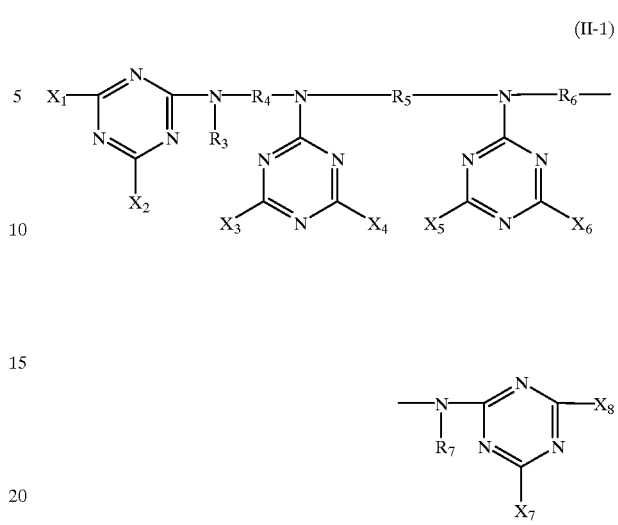

(II-1)

in which

R$_3$ and R$_7$ independently of one another are hydrogen or $C_1$–$C_{12}$alkyl, R$_4$, R$_5$ and R$_6$ independently of one another are $C_2$–$C_{10}$alkylene and X$_1$, X$_2$, X$_3$, X$_4$, X$_5$, X$_6$, X$_7$ and X$_8$ independently of one another are a group of the formula III-1

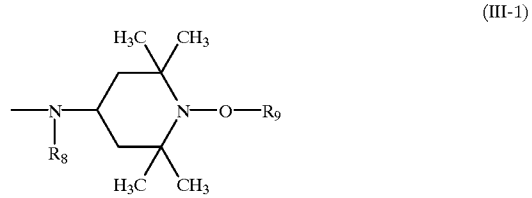

(III-1)

in which

R$_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or is a group of the formula IV-1

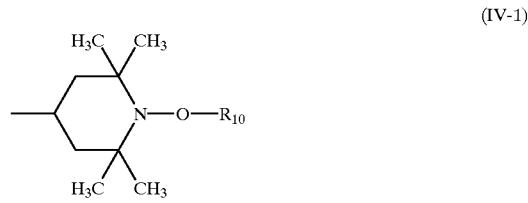

(IV-1)

and R$_9$ and R$_{10}$ independently of one another are hydrogen, $C_1$–$C_{18}$alkyl, $C_5$–$C_{12}$cycloalkyl or $C_1$–$C_4$alkyl-substuted $C_5$–$C_{12}$cycloalky;

component I-c) is at least one compound of the formula V-1

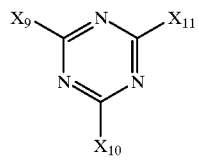
(V-1)

in which $X_9$, $X_{10}$ and $X_{11}$ independently of one another are a group of the formula III-1;

component I-d) is at least one compound of the formula VI-1

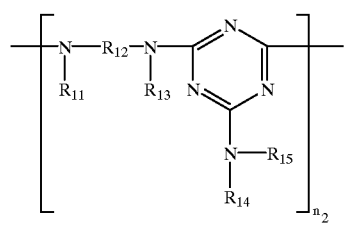
(VI-1)

in which $R_{11}$, $R_{13}$, $R_{14}$ and $R_{15}$ independently of one another are hydrogen, $C_1$–$C_{12}$alkyl, $C_5$–$C_{12}$cycloalkyl, $C_1$–$C_4$alkyl-substituted $C_5$–$C_{12}$cycloalkl, phenyl, —OH— and/or $C_1$–$C_{10}$alkyl-substituted phenyl, $C_7$–$C_9$phenylalky, $C_7$–$C_9$phenylalkyl which is substituted on the phenyl radical by —OH and/or $C_1$–$C_{10}$alkyl, or are a group of the formula IV-1, $R_{12}$ is $C_2$–$C_{18}$alkylene, $C_5$–$C_7$cycloalkylene or $C_1$–$C_4$alkylenedi($C_5$–$C_7$cycloalkylene), or the radicals $R_{11}$, $R_{12}$ and $R_{13}$, together with the nitrogen atoms to which they are attached, form a 5- to 10-membered heterocyclic ring, or $R_{14}$ and $R_{15}$, together with the nitrogen atom to which they are attached, form a 5- to 10-membered heterocyclic ring, $n_2$ is a number from 2 to 50 and at least one of the radicals $R_{11}$, $R_{13}$, $R_{14}$ and $R_{15}$ is a group of the formula IV-1;

component I-e) is at least one compound of the formula VII-1

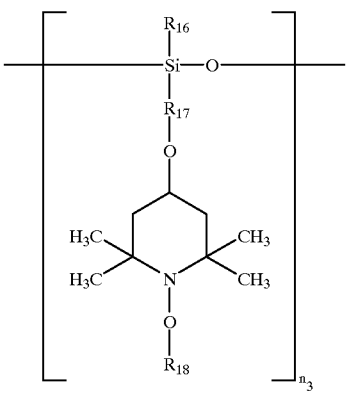
(VII-1)

in which $R_{16}$ is $C_1$–$C_{10}$ alkyl, $C_5$–$C_{12}$cycloalkyl, $C_1$–$C_4$alkyl-substituted $C_5$–$C_{12}$cycloalkyl, phenyl or $C_1$–$C_{10}$alkyl-substituted phenyl, $R_{17}$ is $C_3$–$C_{10}$alkylene, $R_{18}$ is as defined for $R_1$ and $n_3$ is a number from 1 to 50;

component I-f) is a product obtainable by
a) reacting a product, obtained by reaction of a polyamine of the fomula VIII-1-a with cyanuric chloride, with a compound of the formula VIII-1-b

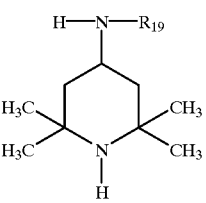
(VIII-1-b)

in which $n_4'$, $n_4''$ and $n_4'''$ in dependently of one another are a number from 2 to 12 and $R_{19}$ is hydrogen, $C_1$–$C_{12}$alkyl, $C_5$–$C_{12}$cycloalkyl, phenyl or $C_7$–$C_9$phenylalkyl, and b) further reactiog the 2,2,6,6-tetramethylpiperid-4-yl groups present in the molecule to give groups of the formula VIII-1-c

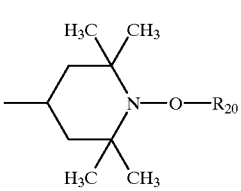
(VIII-1-c)

in which $R_{20}$ is as defined for $R_1$;

component I-g) is at least one compound of the formula IX-1

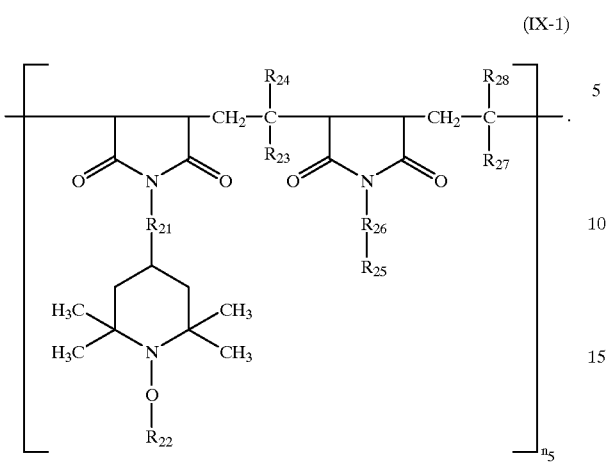

(IX-1)

in which $R_{21}$ and $R_{26}$ independently of one another are a direct bond or a group —N($Y_1$)—CO—$Y_2$—CO—N($Y_3$)—, $Y_1$ and $Y_3$ independently of one another are hydrogen, $C_1$–$C_8$alkyl, $C_5$–$C_{12}$cycloalkyl, phenyl, $C_7$–$C_9$phenylalkyl or a group of the formula IV-1, $Y_2$ is a dirtect bond or $C_1$–$C_4$alkylene, $R_{22}$ is as defined for $R_1$, $R_{23}$, $R_{24}$, $R_{27}$ and $R_{28}$ independently of one another are hydrogen, $C_1$–$C_{30}$alkyl, $C_5$–$C_{12}$cycloalkyl or phenyl, $R_{25}$ is hydrogen, $C_1$–$C_{30}$alkyl, $C_5$–$C_{12}$cycloalkyl, phenyl, $C_7$–$C_9$phenylalkyl or a group of the formula IV-1 and $n_5$ is a number from 1 to 50;

component I-h) is at least one compound of the formula X-1

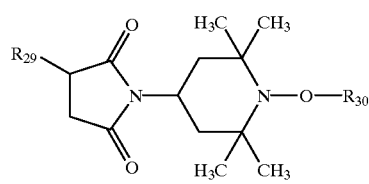

(X-1)

in which $R_{29}$ is $C_1$–$C_{14}$alkyl and $R_{30}$ is as defined for $R_1$;

component I-i) is at least one compound of the formula XI-1

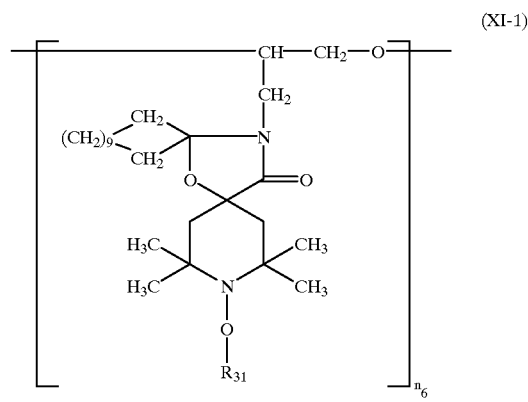

(XI-1)

in which $R_{31}$ is as defined for $R_1$ and $n_6$ is a number from 2 to 50;

component I-j) is at least one compound of the fonnula XII-1

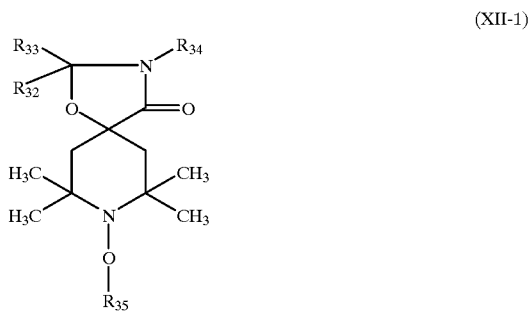

(XII-1)

in which $R_{32}$ and $R_{33}$ together are $C_2$–$C_{14}$alkyene, $R_{34}$ is hydrogen or a group —$Z_1$—COO—$Z_2$, $Z_1$ is $C_2$–$C_{14}$alkyene and $Z_2$ is $C_1$–$C_{24}$alkyl and $R_{35}$ is as defined for $R_1$;

component I-k) is at least one compound of the formula XIII-1

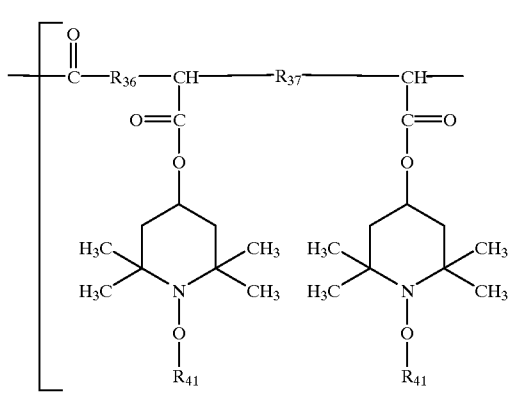

(XIII-1)

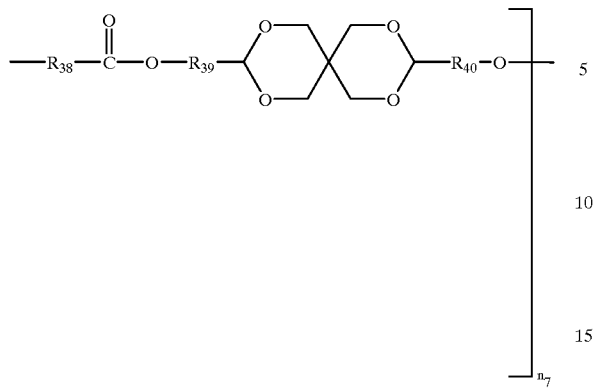

in which $R_{36}$, $R_{37}$, $R_{38}$, $R_{39}$ and $R_{40}$ independently of one another are a direct bond or $C_1$–$C_{10}$alkylene,
$R_{41}$ is as defined for $R_1$ and
$n_7$ is a number from 1 to 50;

component I-l ) is at least one compound of the formula XIV-1

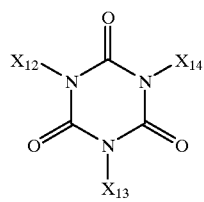

in which
$X_{12}$, $X_{13}$ and $X_{14}$ independently of one another are a group of the formula XV-1

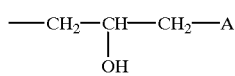

in which A is a group of the formula III-1;
component II-a) is at least one compound of the formula I-2

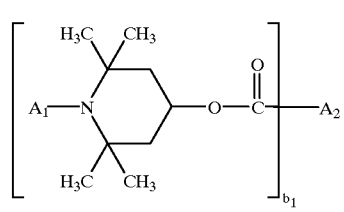

in which
$A_1$ is hydrogen, $C_1$–$C_8$alkyl, oxyl, —$CH_2CN$, $C_3$–$C_6$alkenyl, $C_7$–$C_9$phenylalkyl or $C_7$–$C_9$phenylalkyl which is substituted on the phenyl radical by $C_1$–$C_4$alkyl, $b_1$ is 1, 2 or 4,
if $b_1$ is 1, $A_2$ is $C_1$–$C_{25}$alkyl,
if $b_1$ is 2, $A_2$ is $C_1$–$C_{14}$alkylene and
if $b_1$ is 4, $A_2$ is $C_4$–$C_{10}$alkanetetrayl;

component II-b) is at least one compound of the formula II-2

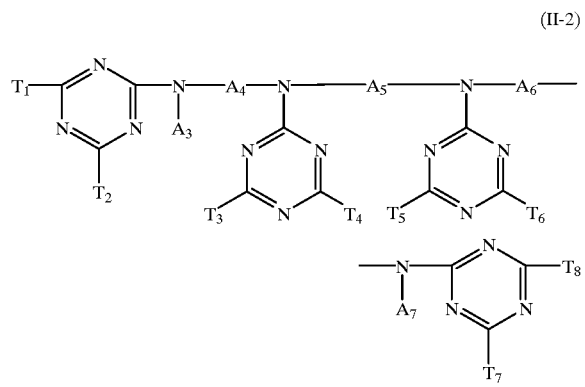

in which
$A_3$ and $A_7$ independently of one another are hydrogen or $C_1$–$C_{12}$alkyl,
$A_4$, $A_5$ and $A_6$ independently of one another are $C_2$–$C_{10}$alkylene and
$T_1$, $T_2$, $T_3$, $T_4$, $T_5$, $T_6$, $T_7$ and $T_8$ independently of one onother are a group of the formula III-2

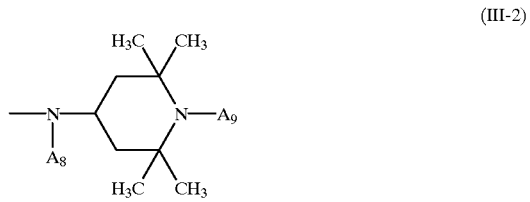

in which $A_8$ is hydrogen, $C_1$–$C_{12}$alkyl, $C_5$–$C_{12}$cycloalkyl, $C_1$–$C_4$alkyl-substituted $C_5$–$C_{12}$cycloalkyl, phenyl, —OH— and/or $C_1$–$C_{10}$alkyl-substituted phenyl, $C_7$–$C_9$phenylalkyl, $C_7$–$C_9$phenylalkyl which is substituted on the phenyl radical by —OH and/or $C_1$–$C_{10}$alkyl, or is a group of the faomula IV-2

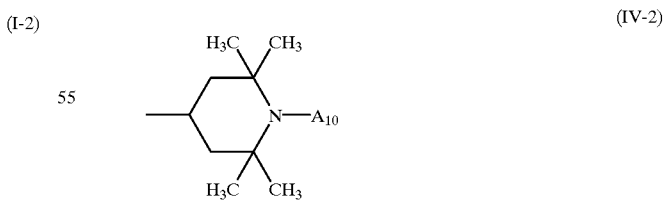

and $A_9$ and $A_{10}$ independently of one another are hydrogen, $C_1$–$C_8$alkyl, oxyl, —$CH_2CN$, $C_3$–$C_6$alkenyl, $C_7$–$C_9$phenylalkyl or $C_7$–$C_9$phenylalkyl which is substituted on the phenyl radical by $C_1$–$C_4$alkyl;

component II-c) is at least one compound of the formula V-2

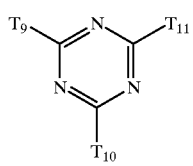
(V-2)

in which
T$_9$, T$_{10}$ and T$_{11}$ independently of one another are a group of the formula III-2;
component II-d) is at least one compound of the formula VI-2

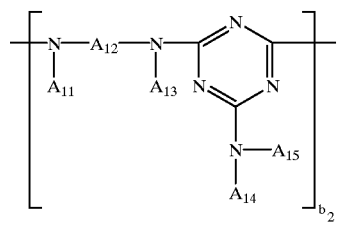
(VI-2)

in which
A$_{11}$, A$_{13}$, A$_{14}$ and A$_{15}$ independently of one another are hydrgen, C$_1$–C$_{12}$alkyl, C$_5$–C$_{12}$cycloalkyl, C$_1$–C$_4$alkyl-substituted C$_5$–C$_{12}$cycloalkyl, phenyl, —OH— and/or C$_1$–C$_{10}$alkyl-substituted phenyl, C$_7$–C$_9$phenylalkyl, C$_7$–C$_9$phenylalkyl which is substiuted on the phenyl radical by —OH and/or C$_1$–C$_{10}$alkyl, or a group of the formula IV-2,
A$_{12}$ is C$_2$–C$_{18}$alkylene, C$_{5-C7}$cycloalkylene or C$_1$–C$_4$alkylenedi(C$_5$–C$_7$cycloalkylene), or the radicals A$_{11}$, A$_{12}$ and A$_{13}$, together with the nitrogen atoms to which they are attached, form a 5- to to 10-membered heterocyclic ring, or
A$_{14}$, and A$_{15}$, together with de nitrogen atom to which they are attached, form a 5- to 10-membered heterocyclic ring,
b$_2$ is a number from 2 to 50 and
at least one of the radicals A$_{11}$, A$_{13}$, A$_{14}$ and A$_{15}$ is a group of the formula IV-2;
component II-e) is at least one compound of the fornula VII-2

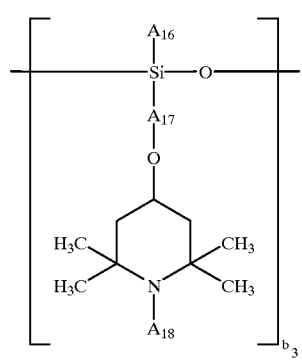
(VII-2)

in which
A$_{16}$ is C$_1$–C$_{10}$alkyl, C$_5$–C$_{12}$cycloalkyl, C$_1$–C$_4$alkyl-substituted C$_5$–C$_{12}$cycloalkyl, phenyl or C$_1$–C$_{10}$alkyl-substituted phenyl, A$_{17}$ is C$_3$–C$_{10}$alkylene,
A$_{18}$ is as defined for A$_1$ and
b$_3$ is a number from 1 to 50;
component II-f) is a product obtainable by reacting a product, obtained by reaction of a polyamine of the formula VIII-2-a with cyanuric chloride, with a compound of the formula VIII-2-b

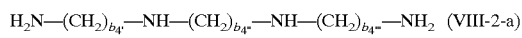
H$_2$N—(CH$_2$)$_{b_4'}$—NH—(CH$_2$)$_{b_4''}$—NH—(CH$_2$)$_{b_4'''}$—NH$_2$  (VIII-2-a)

(VIII-2-b)
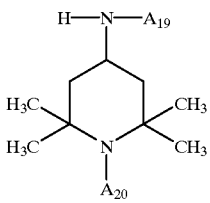

in which
b$_4'$, b$_4''$ and b$_4'''$ independently of one another are a number from 2 to 12,
A$_{19}$ is hydrogen, C$_1$–C$_{12}$alkyl, C$_5$–C$_{12}$cycloalkyl, phenyl or C$_7$–C$_9$phenylalkyl and
A$_{20}$ is as defined for A$_1$;
conmponent II-g) is at least one compound of the formula IX-2

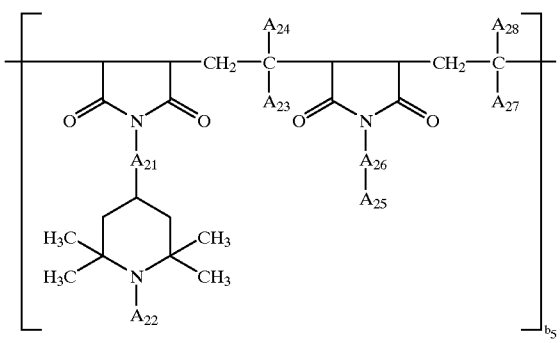
(IX-2)

in which
A$_{21}$ and A$_{26}$ independently of one anothe are a direct bond or a group —N(E$_1$)—CO—E$_2$—CO—N(E$_3$)—,
E$_1$ and E$_3$ independently of one another are hydrogen, C$_1$–C$_8$alkyl, C$_5$–C$_{12}$cycloalkyl, phenyl,
C$_7$–C$_9$phenylalkyl or a group of the formula IV-2,
E$_2$ is a direct bond or C$_1$–C$_4$alkylene,
A$_{22}$ is as defined for A$_1$,
A$_{23}$, A$_{24}$, A$_{27}$ and A$_{28}$ independently of one another are hydrogen, C$_1$–C$_{30}$alkyl, C$_5$–C$_{12}$cycloalkyl or phenyl,
A$_{25}$ is hydrogen, C$_1$–C$_{30}$alkyl, C$_5$–C$_{12}$cycloalkyl, phenyl, C$_7$–C$_9$phenylalkyl or a group of the formula IV-2 and
b$_5$ is a number from 1 to 50;
component II-h) is at least one compound of the formula X-2

(X-2)

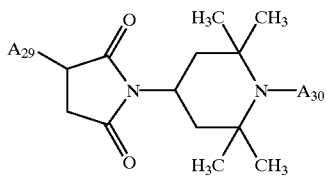

in which $A_{29}$ is $C_1$–$C_{24}$alkyl and $A_{30}$ is as defined for $A_1$;

component II-i) is at least one compound of the formula XI-2

(XI-2)

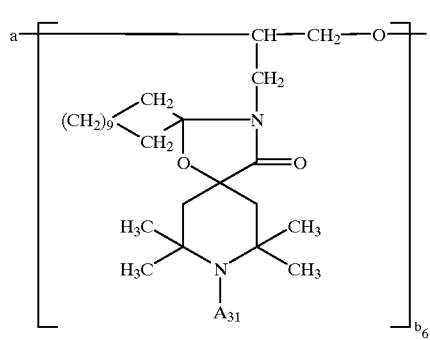

in which $A_{31}$ is as defined for $A_1$ and $b_6$ is a number fom 2 to 50;

component II-j) is at least one compound of the formula XII-2

(XII-2)

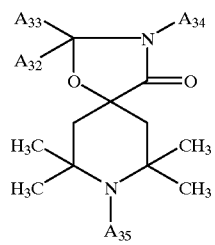

in which $A_{32}$ and $A_{33}$ together form $C_2$–$C_4$alkyene, $A_{34}$ is hydrogen or a group —$G_1$—COO—$G_2$, $G_1$ is $C_2$–$C_{14}$alkylene and $G_2$ is $C_1$–$C_{24}$alkyl and $A_{35}$ is as defined for $A_1$;

component II-k) is at least one compound of the formula XIII-2

(XIII-2)

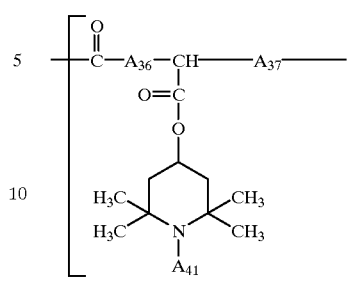

(XIV)

in which $A_{36}$, $A_{37}$, $A_{38}$, $A_{39}$ and $A_{40}$ independently of one another are a direct bond or $C_1$–$C_{10}$alkylene, $A_{41}$ is as defined for $A_1$ and $b_7$ is a number frorn 1 to 50;

component II-l) is at least one compound of the formula XV-2

(XIV-2)

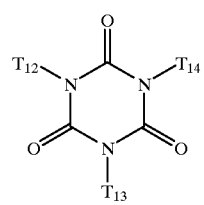

in which $T_{12}$, $T_{13}$ and $T_{14}$ independently of one another are a group of the formula XV-2

(XV-2)

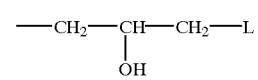

in which L is a group of the formula III-2;

component II-m) is at least one compound of the formula XVI-2

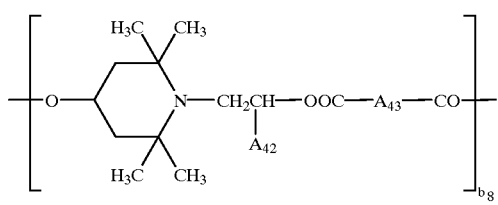

(XVI-2)

in which $A_{42}$ is hydrogen or methyl,
$A_{43}$ is a direct bond or $C_1$–$C_{10}$alklene and
$b_8$ is a number from 2 to 50.

2. A stabilizer mixture according to claim 1, in which $R_1$, $R_9$, $R_{10}$, $R_{18}$, $R_{20}$, $R_{22}$, $R_{30}$, $R_{31}$ $R_{35}$ and $R_{41}$ independently of one another are $C_1$–$C_{12}$alkyl, $C_5$–$C_8$cycloalkyl or methyl-substituted $C_5$–$C_8$cycloalkyl.

3. A stabilizer mixture according to claim 1, in which $R_1$, $R_9$, $R_{10}$, $R_{18}$, $R_{20}$, $R_{22}$, $R_{30}$, $R_{31}$, $R_{35}$ and $R_{41}$ independently of one another are methyl, octyl or cyclohexyl.

4. A stabilizer mixture according to claim 1, in which $A_1$, $A_9$, $A_{10}$, $A_{18}$, $A_{20}$, $A_{22}$, $A_{30}$, $A_{31}$, $A_{35}$ and $A_{41}$ independently of one another are hydrogen or methyl.

5. A stabilizer mixture according to claim 1, comprising a component I-a), I-b), I-c), I-d), I-e), I-f), I-g), I-h), I-i), I-j), I-k) or I-l) and a component II-a), II-b), II-d), II-e), II-f), II-g), II-i), II-k) or II-m).

6. A stabilizer mixture according to claim 1,
in which $n_1$ is 1, 2 or 4,
if $n_1$ is 1, $R_2$ is $C_{10}$–$C_{20}$alkyl,
if $n_1$ is 2, $R_2$ is $C_6$–$C_{10}$alkylene and
if $n_1$ is 4, $R_2$ is butanetetrayl;

$R_3$ and $R_7$ independently of one another are hydrogen or $C_1$–$C_4$alkyl, $R_4$, $R_5$ and $R_6$ independently of one another are $C_2$–$C_6$alkylene, $R_8$ is hydrogen, $C_1$–$C_6$alkyl, $C_5$–$C_8$cycloalkyl, methyl-substituted $C_5$–$C_8$cycloalkyl, phenyl, $C_7$–$C_9$phenylalkyl or a group of the formula IV-1;

$R_{11}$, $R_{13}$, $R_{14}$ and $R_{15}$ independently of one another are hydrogen, $C_1$–$C_8$alkyl, $C_5$–$C_8$cycloalkyl, methyl-substituted $C_5$–$C_8$cycloalkyl, phenyl, $C_7$–$C_9$phenylalkyl or a group of the formula IV-1, or the radicals $R_{14}$ and $R_{15}$, together with the nitrogen atom to which they are attached, form a 6-membered heterocyclic ring, $R_{12}$ is $C_2$–$C_{10}$alkylene and
$n_2$ is a number from 2 to 25;
$R_{16}$ is $C_1$–$C_4$alkyl, $C_5$–$C_8$cycloalkyl or phenyl,
$R_{17}$ is $C_3$–$C_6$alkylene and
$n_3$ is a number from 1 to 25;
$n_4'$, $n_4''$ and $n_4'''$ independently of one another are a number from 2 to 4 and
$R_{19}$ is $C_1$–$C_4$alkyl;
$R_{21}$ and $R_{26}$ independently of one another are a direct bond or a group —N($Y_1$)—CO—$Y_2$—CO—N($Y_3$)—,
$Y_1$ and $Y_3$ independently of one another are hydrogen or $C_1$–$C_4$alkyl,
$Y_2$ is a direct bond,
$R_{23}$ and $R_{27}$ are $C_1$–$C_{25}$alkyl or phenyl,
$R_{24}$ and $R_{28}$ are hydrogen or $C_1$–$C_4$alkyl,
$R_{25}$ is $C_1$–$C_{25}$alkyl or a group of the formula IV-1 and
$n_5$ is a number from 1 to 25;
$R_{29}$ is $C_8$–$C_{15}$alkyl;
$n_6$ is a number from 2 to 25;
$R_{32}$ and $R_{33}$ together form $C_8$–$C_{14}$alkylene,
$R_{34}$ is hydrogen or a group —$Z_1$—COO—$Z_2$,
$Z_1$ is $C_2$–$C_6$alkylene and
$Z_2$ is $C_8$–$C_{15}$alkyl;
$R_{36}$, $R_{38}$, $R_{39}$ and $R_{40}$ independently of one another are $C_1$–$C_4$alkylene,
$R_{37}$ is a direct bond and
$n_7$ is a number from 1 to 25.

7. A stabilizer mixture according to claim 1, in which component I-a) is at least one compound of the formula I-1-a-1, I-1-a-2 or I-1-a-3

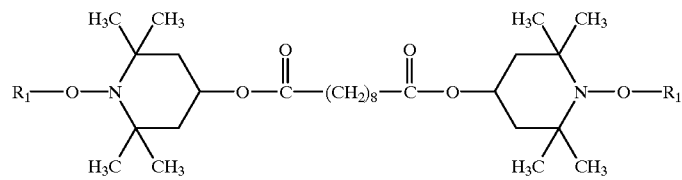

(I-1-a-1)

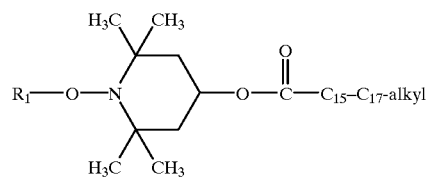

(I-1-a-2)

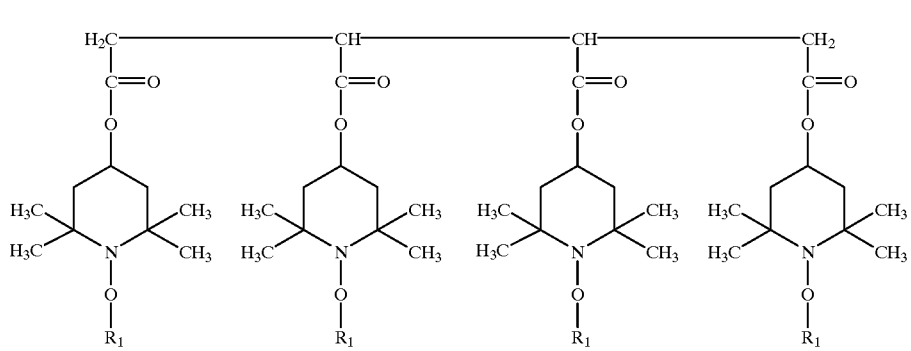
in which $R_1$ is methyl, octyl or cyclohexyl;
component I-b) is at least one compound of the formula II-1-b
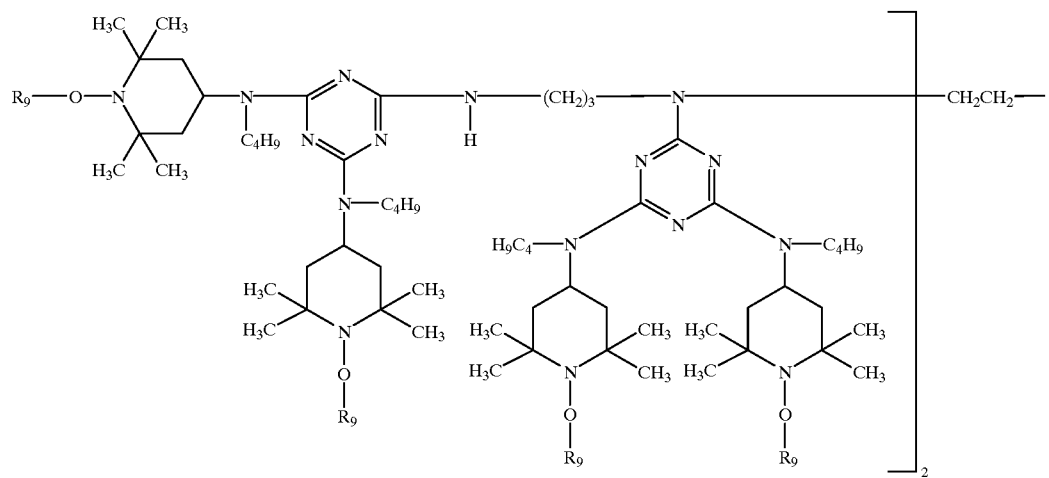
in which $R_9$ is as defined for $R_1$;
component I-c) is at least one compound of the formula V-1-c
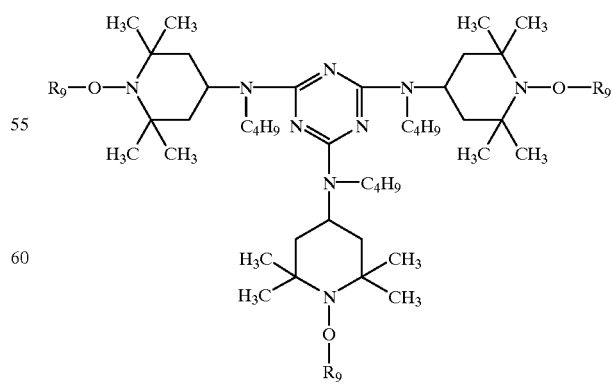

in which $R_9$ is as defined above;
component I-d) is at least one compound of the formula VI-1-d-1, VI-1-d-2 or VI-1-d-3

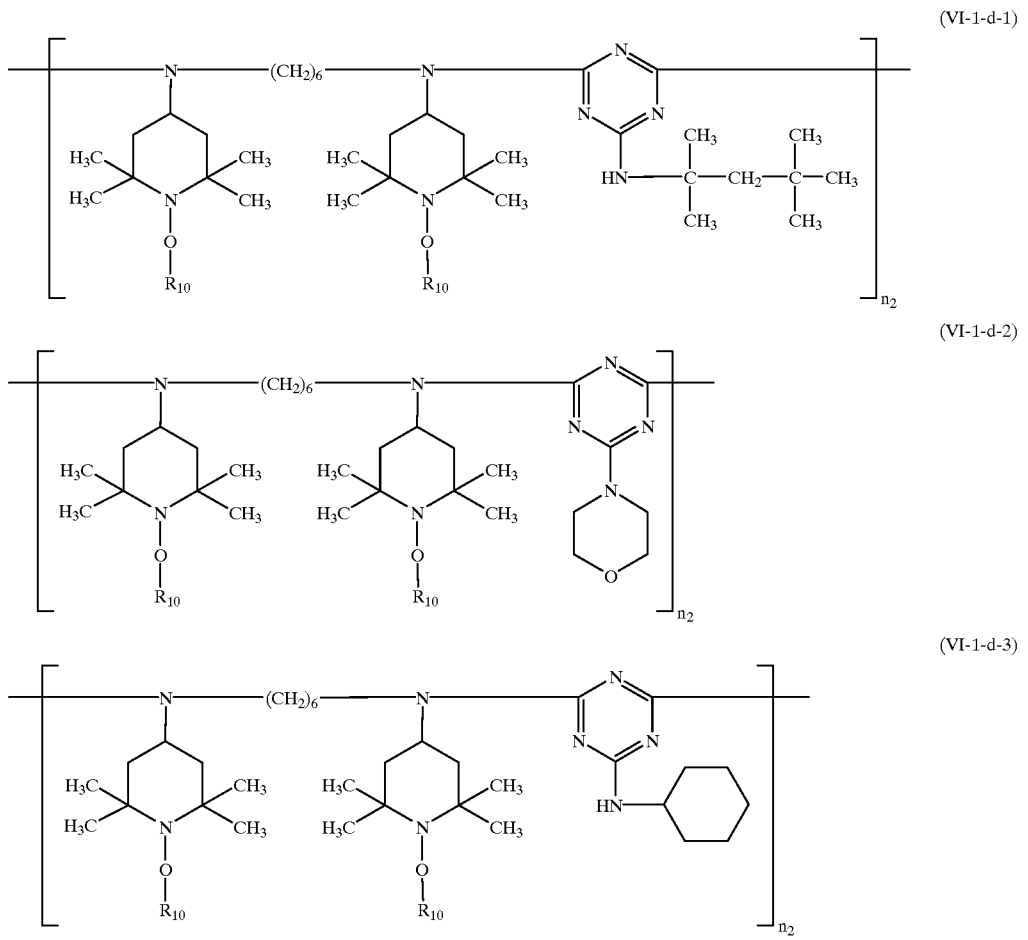

in which $R_{10}$ is as defined for $R_1$ and $n_2$ is a number from 2 to 25;

component I-e) is at least one compound of the formula VII-1-e

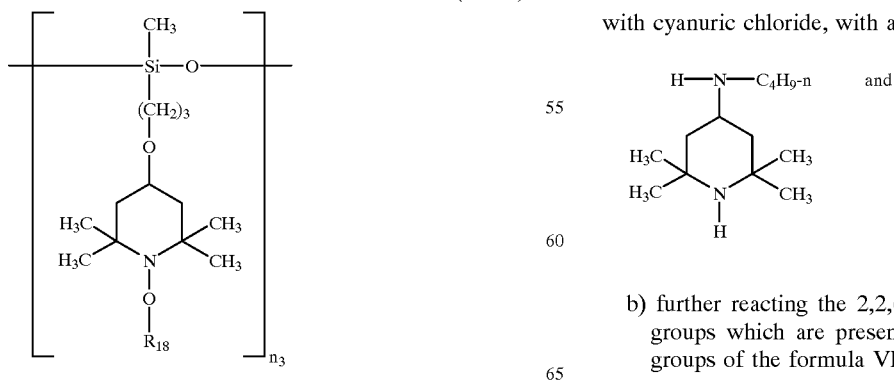

in which $R_{18}$ is as defined for $R_1$ and $n_3$ is a number from 1 to 25;

component I-f) is a product obtainable by a) reacting a product, obtained by reaction of a polyamine of the formula

with cyanuric chloride, with a compound of the formula and b) further reacting the 2,2,6,6-tetramethylpiperid-4-yl groups which are present in the molecule to give groups of the formula VIII-1-c;

component 1-g) is at least one compound of the formula IX-1-g-1, IX-1-g-2 or IX-1-g-3

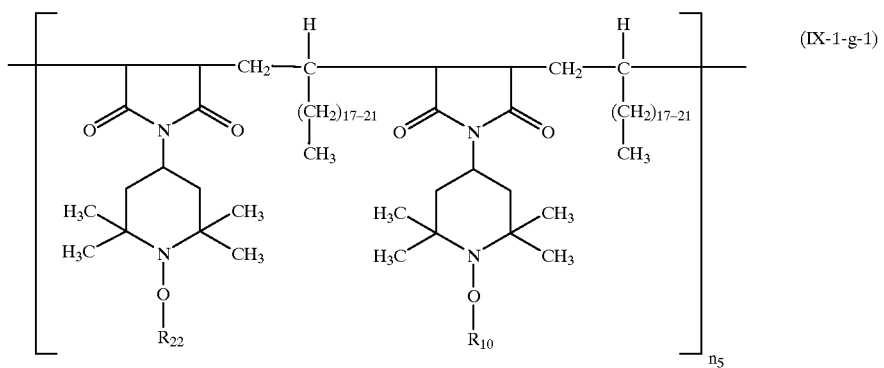
(IX-1-g-1)
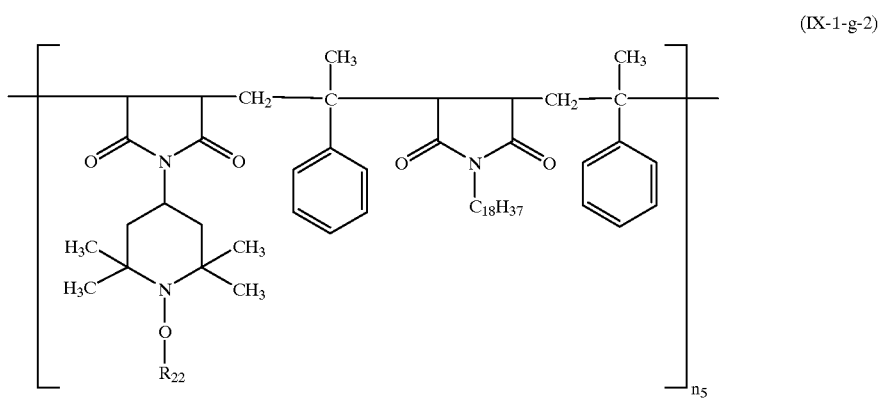
(IX-1-g-2)
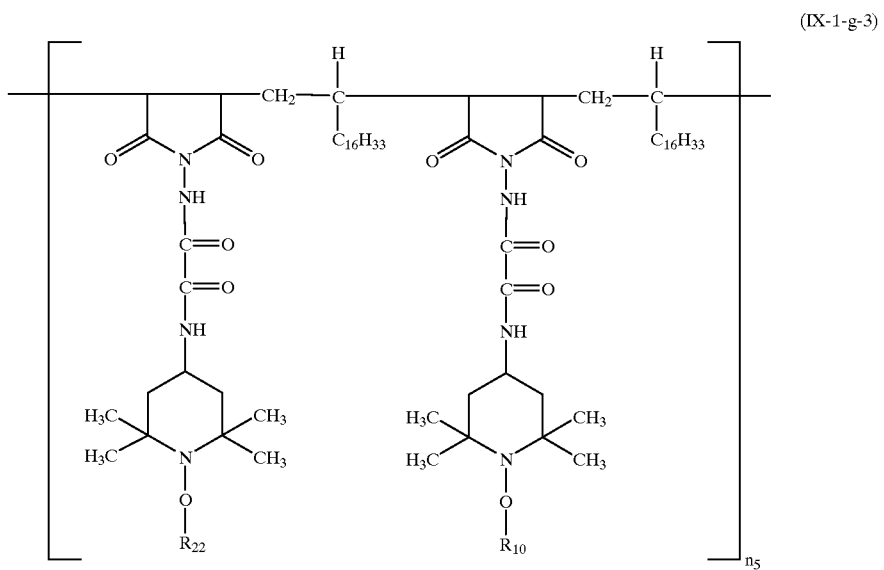
(IX-1-g-3)

in which $R_{10}$ and $R_{22}$ are as defined for $R_1$ and $n_5$ is a number from 1 to 25;

component 1-h) is at least one compound of the formula X-1-h

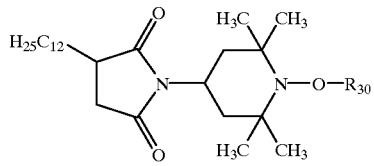

(X-1-h)

in which $R_{30}$ is as defined for $R_1$;

component I-i) is at least one compound of the formula (XI-1) in which $R_{31}$ is as defined for $R_1$ and $n_6$ is a number from 2 to 25;

component I-j) is at least one compound of the formula XI-1-j-1 or XII-1-j-2

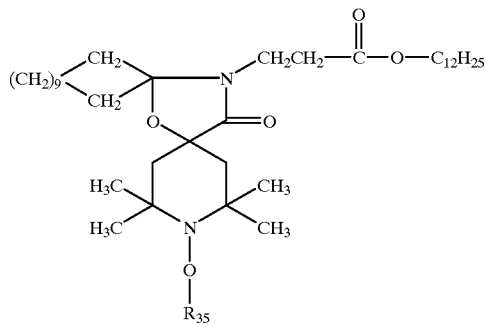

(XII-1-j-2)

in which $R_{35}$ is as defined for $R_1$;

component I-k) is at least one compound of the formula XIII-1-k

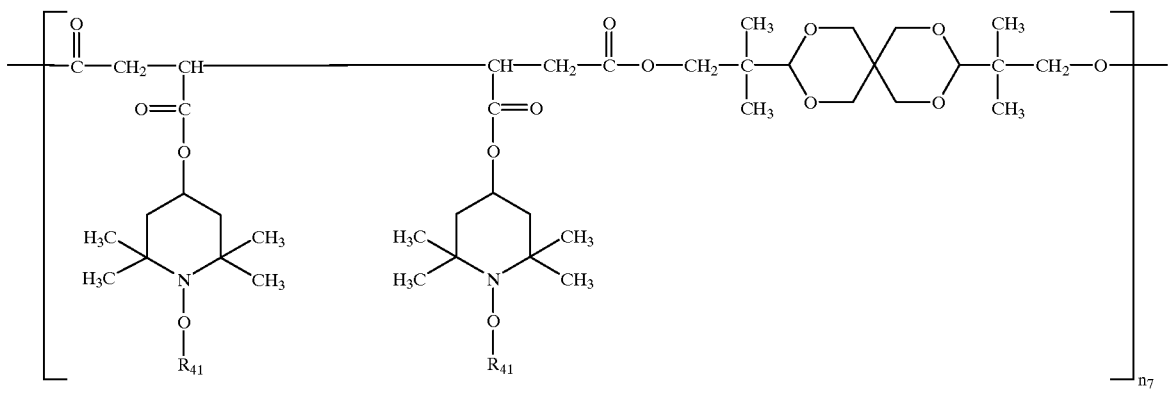

(XIII-1-k)

in which $R_{41}$ is as defined for $R_1$ and $n_7$ is a number from 1 to 25;

component I-l) is at least one compound of the formula XIV-1-1

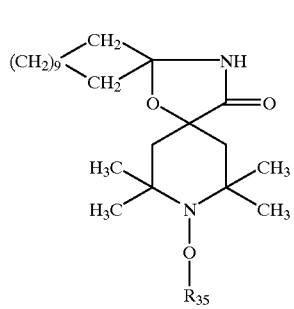

(XII-1-j-1)

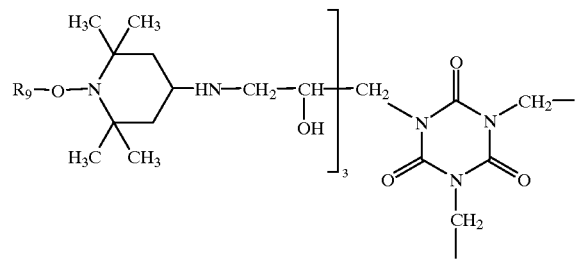

(XIV-1-1)

in which $R_9$ is as defined for $R_1$.

8. A composition comprising an organic material sensitive to oxidative, thermal or light-induced degradation and a stabilizer mixture according to claim 1.

9. A composition according to claim 8, in which the organic material is a polyolefin.

10. A composition according to claim 8 in which the organic material is polyethylene, polypropylene or a copolymer of polyethylene or polypropylene.

* * * * *